United States Patent
Edwards et al.

(10) Patent No.: US 10,688,244 B2
(45) Date of Patent: Jun. 23, 2020

(54) MEDICAMENT DELIVERY DEVICE AND METHODS FOR DELIVERING DRUGS TO INFANTS AND CHILDREN

(71) Applicant: kaleo, Inc., Richmond, VA (US)

(72) Inventors: Eric S. Edwards, Moseley, VA (US); Evan T. Edwards, Charlottesville, VA (US); Glen L. Kelley, Glen Allen, VA (US); Paul F. Meyers, Fishers, IN (US)

(73) Assignee: kaleo, Inc., Richmond, VA (US)

( * ) Notice: Subject to any disclaimer, the term of this patent is extended or adjusted under 35 U.S.C. 154(b) by 0 days.

(21) Appl. No.: 16/071,203

(22) PCT Filed: Dec. 21, 2017

(86) PCT No.: PCT/US2017/067873
§ 371 (c)(1),
(2) Date: Jul. 19, 2018

(87) PCT Pub. No.: WO2018/119218
PCT Pub. Date: Jun. 28, 2018

(65) Prior Publication Data
US 2019/0358399 A1 Nov. 28, 2019

Related U.S. Application Data

(60) Provisional application No. 62/438,584, filed on Dec. 23, 2016.

(51) Int. Cl.
*A61M 5/20* (2006.01)
*A61M 5/32* (2006.01)
(Continued)

(52) U.S. Cl.
CPC ......... *A61M 5/2033* (2013.01); *A61K 31/137* (2013.01); *A61M 5/2066* (2013.01);
(Continued)

(58) Field of Classification Search
CPC .... A61M 5/2033; A61M 5/2066; A61M 5/24; A61M 5/3202; A61M 5/31533;
(Continued)

(56) References Cited

U.S. PATENT DOCUMENTS 2,409,656 A 10/1946 Austin
2,960,087 A 11/1960 Uytenbogaart
(Continued)

FOREIGN PATENT DOCUMENTS

DE 2019296 11/1971
EP 1287840 A1 3/2003
(Continued)

OTHER PUBLICATIONS

RXList, How to Administer EpiPen Jr., <www.rxlist.com/epipen-drug/indications-dosage.htm>, "Dosage and Administration", last reviewed. (Year: 2016).*
(Continued)

*Primary Examiner* — Brandy S Lee
*Assistant Examiner* — Nidah M Hussain
(74) *Attorney, Agent, or Firm* — ReavesColey PLLC

(57) ABSTRACT

A method of delivering epinephrine includes placing a distal end surface of a medical injector into contact with a target location of a patient. The medical injector includes a housing, an energy storage member, and a medicament container containing a dose of epinephrine effective for administration to the patient experiencing anaphylaxis and having a weight of less than 15 kg. The medicament container is coupled to a needle. The medical injector is actuated such that the energy storage member produces a force to move the needle from a first needle position to a second needle position. A distal tip of the needle extends from the distal end surface by a distance of between 7 millimeters and 8 millimeters when the needle is in the second needle position. A portion of the (Continued)

force is exerted to expel the dose of epinephrine when the needle is in the second position.

23 Claims, 55 Drawing Sheets

(51) Int. Cl.
    *A61K 31/137*     (2006.01)
    *A61M 5/24*     (2006.01)
    *A61M 5/142*     (2006.01)
    *A61M 5/315*     (2006.01)
    *A61M 5/28*     (2006.01)

(52) U.S. Cl.
    CPC ............ *A61M 5/24* (2013.01); *A61M 5/3202* (2013.01); *A61M 5/2046* (2013.01); *A61M 5/285* (2013.01); *A61M 5/31533* (2013.01); *A61M 2005/14288* (2013.01); *A61M 2005/206* (2013.01); *A61M 2005/2013* (2013.01); *A61M 2005/2026* (2013.01); *A61M 2005/2474* (2013.01); *A61M 2005/31588* (2013.01); *A61M 2205/3306* (2013.01); *A61M 2205/3317* (2013.01); *A61M 2205/3561* (2013.01); *A61M 2205/581* (2013.01); *A61M 2205/584* (2013.01)

(58) Field of Classification Search
    CPC .. A61M 2005/2013; A61M 2005/2026; A61M 2005/206; A61M 2005/2474; A61M 2205/581; A61M 2205/584; A61K 31/137
    USPC .......................................................... 604/131
    See application file for complete search history.

(56) References Cited

U.S. PATENT DOCUMENTS

| | | |
|---|---|---|
| 3,055,362 A | 9/1962 | Uytenbogaart |
| 3,115,133 A | 12/1963 | Morando |
| 3,426,448 A | 2/1969 | Sarnoff |
| 3,565,070 A | 2/1971 | Hanson et al. |
| 3,583,373 A | 2/1971 | Paulson |
| 3,688,765 A | 9/1972 | Gasaway |
| 3,768,472 A | 10/1973 | Hodosh et al. |
| 3,795,061 A | 3/1974 | Sarnoff et al. |
| 3,797,489 A | 3/1974 | Sarnoff |
| 3,941,130 A | 3/1976 | Tibbs |
| 3,945,379 A | 3/1976 | Pritz et al. |
| 4,031,889 A | 6/1977 | Pike |
| 4,086,062 A | 4/1978 | Hach |
| 4,108,177 A | 8/1978 | Pistor |
| 4,124,024 A | 11/1978 | Schwebel et al. |
| 4,226,235 A | 10/1980 | Sarnoff et al. |
| 4,227,528 A | 10/1980 | Wardlaw |
| 4,258,713 A | 3/1981 | Wardlaw |
| 4,360,019 A | 11/1982 | Portner et al. |
| 4,378,015 A | 3/1983 | Wardlaw |
| 4,394,863 A | 7/1983 | Bartner |
| 4,424,057 A | 1/1984 | House |
| 4,441,629 A | 4/1984 | Mackal |
| 4,484,910 A | 11/1984 | Sarnoff |
| 4,573,976 A | 3/1986 | Sampson et al. |
| 4,596,556 A | 6/1986 | Morrow et al. |
| 4,610,666 A | 9/1986 | Pizzino |
| 4,617,557 A | 10/1986 | Gordon |
| 4,624,660 A | 11/1986 | Mijers et al. |
| 4,640,686 A | 2/1987 | Dalling et al. |
| 4,643,721 A | 2/1987 | Brunet |
| 4,664,653 A | 5/1987 | Sagstetter et al. |
| 4,666,430 A | 5/1987 | Brown et al. |
| 4,673,657 A | 6/1987 | Christian |
| 4,689,042 A | 8/1987 | Sarnoff et al. |
| 4,693,708 A | 9/1987 | Wanderer et al. |
| 4,755,169 A | 7/1988 | Sarnoff et al. |
| 4,759,527 A | 7/1988 | Brown et al. |
| 4,781,697 A | 11/1988 | Slaughter |
| 4,782,841 A | 11/1988 | Lopez |
| 4,784,652 A | 11/1988 | Wikström |
| 4,795,433 A | 1/1989 | Sarnoff |
| 4,820,286 A | 4/1989 | van der Wal |
| 4,822,340 A | 4/1989 | Kamstra |
| 4,826,489 A | 5/1989 | Haber |
| 4,853,521 A | 8/1989 | Claeys et al. |
| 4,874,382 A | 10/1989 | Lindemann et al. |
| 4,894,054 A | 1/1990 | Miskinyar |
| 4,906,235 A | 3/1990 | Roberts |
| 4,915,695 A | 4/1990 | Koobs |
| 4,941,880 A | 7/1990 | Burns |
| 4,959,056 A | 9/1990 | Dombrowski et al. |
| 4,968,302 A | 11/1990 | Schluter et al. |
| 4,983,164 A | 1/1991 | Hook et al. |
| 5,000,736 A | 3/1991 | Kaufhold, Jr. et al. |
| 5,024,656 A | 6/1991 | Gasaway et al. |
| 5,037,306 A | 8/1991 | van Schoonhoven |
| 5,038,023 A | 8/1991 | Saliga |
| 5,041,088 A | 8/1991 | Ritson et al. |
| 5,042,977 A | 8/1991 | Bechtold et al. |
| 5,062,603 A | 11/1991 | Smith et al. |
| 5,064,413 A | 11/1991 | McKinnon et al. |
| 5,071,353 A | 12/1991 | van der Wal |
| 5,085,642 A | 2/1992 | Sarnoff et al. |
| 5,092,842 A | 3/1992 | Bechtold et al. |
| 5,092,843 A | 3/1992 | Monroe et al. |
| 5,104,380 A | 4/1992 | Holman et al. |
| 5,125,898 A | 6/1992 | Kaufhold, Jr. et al. |
| 5,147,311 A | 9/1992 | Pickhard |
| 5,167,641 A | 12/1992 | Schmitz |
| 5,199,949 A | 4/1993 | Haber et al. |
| 5,224,936 A | 7/1993 | Gallagher |
| 5,240,146 A | 8/1993 | Smedley et al. |
| 5,244,465 A | 9/1993 | Michel |
| 5,271,527 A | 12/1993 | Haber et al. |
| 5,281,198 A | 1/1994 | Haber et al. |
| 5,286,258 A | 2/1994 | Haber et al. |
| 5,295,965 A | 3/1994 | Wilmot |
| 5,298,023 A | 3/1994 | Haber et al. |
| 5,312,326 A | 5/1994 | Myers et al. |
| 5,314,412 A | 5/1994 | Rex |
| 5,335,672 A | 8/1994 | Bennett |
| 5,343,519 A | 8/1994 | Feldman |
| 5,344,407 A | 9/1994 | Ryan |
| 5,354,284 A | 10/1994 | Haber et al. |
| 5,356,376 A | 10/1994 | Milijasevic et al. |
| 5,358,489 A | 10/1994 | Wyrick |
| 5,363,842 A | 11/1994 | Mishelevich et al. |
| 5,380,281 A | 1/1995 | Tomellini et al. |
| 5,383,851 A | 1/1995 | McKinnon, Jr. et al. |
| 5,383,864 A | 1/1995 | van den Heuvel |
| 5,395,345 A | 3/1995 | Gross |
| 5,399,163 A | 3/1995 | Peterson et al. |
| 5,417,660 A | 5/1995 | Martin |
| 5,451,210 A | 9/1995 | Kramer et al. |
| 5,466,217 A | 11/1995 | Myers et al. |
| 5,478,316 A | 12/1995 | Bitdinger et al. |
| 5,514,097 A | 5/1996 | Knauer |
| 5,514,135 A | 5/1996 | Earle |
| 5,527,287 A | 6/1996 | Miskinyar |
| 5,540,664 A | 7/1996 | Wyrick |
| 5,558,679 A | 9/1996 | Tuttle |
| 5,567,160 A | 10/1996 | Massino |
| 5,568,555 A | 10/1996 | Shamir |
| 5,569,192 A | 10/1996 | van der Wal |
| 5,584,815 A | 12/1996 | Pawelka et al. |
| 5,615,771 A | 4/1997 | Hollister |
| 5,616,132 A | 4/1997 | Newman |
| 5,645,534 A | 7/1997 | Chanoch |
| 5,658,259 A | 8/1997 | Pearson et al. |
| 5,681,291 A | 10/1997 | Galli |
| 5,681,292 A | 10/1997 | Tober et al. |
| 5,695,476 A | 12/1997 | Harris |
| 5,716,338 A | 2/1998 | Hjertman et al. |
| 5,728,074 A | 3/1998 | Castellano et al. |

(56) References Cited

U.S. PATENT DOCUMENTS

| | | |
|---|---|---|
| 5,734,109 A | 3/1998 | Thanscheidt |
| 5,772,635 A | 6/1998 | Dastur et al. |
| 5,779,677 A | 7/1998 | Frezza |
| 5,792,190 A | 8/1998 | Olson et al. |
| 5,800,397 A | 9/1998 | Wilson et al. |
| 5,805,423 A | 9/1998 | Wever et al. |
| 5,809,997 A | 9/1998 | Wolf |
| 5,813,570 A | 9/1998 | Fuchs et al. |
| 5,814,020 A | 9/1998 | Gross |
| 5,823,346 A | 10/1998 | Weiner |
| 5,832,488 A | 11/1998 | Eberhardt |
| 5,837,546 A | 11/1998 | Allen et al. |
| RE35,986 E | 12/1998 | Ritson et al. |
| 5,846,089 A | 12/1998 | Weiss et al. |
| 5,848,990 A | 12/1998 | Cirelli et al. |
| 5,852,590 A | 12/1998 | de la Huerga |
| 5,853,292 A | 12/1998 | Eggert et al. |
| 5,858,001 A | 1/1999 | Tsals et al. |
| 5,860,957 A | 1/1999 | Jacobsen et al. |
| 5,865,795 A | 2/1999 | Schiff et al. |
| 5,868,711 A | 2/1999 | Kramer et al. |
| 5,868,713 A | 2/1999 | Klippenstein |
| 5,868,721 A | 2/1999 | Marinacci |
| D407,487 S | 3/1999 | Greubel et al. |
| 5,876,380 A | 3/1999 | Manganini et al. |
| 5,925,021 A | 7/1999 | Castellano et al. |
| 5,928,195 A | 7/1999 | Malamud |
| 5,941,857 A | 8/1999 | Nguyen et al. |
| 5,964,739 A | 10/1999 | Champ |
| 5,971,953 A | 10/1999 | Bachynsky |
| 6,015,438 A | 1/2000 | Shaw |
| 6,030,363 A | 2/2000 | Kriesel |
| 6,039,713 A | 3/2000 | Botich et al. |
| 6,045,534 A | 4/2000 | Jacobsen et al. |
| 6,050,977 A | 4/2000 | Adams |
| 6,056,728 A | 5/2000 | von Schuckmann |
| 6,062,901 A | 5/2000 | Liu et al. |
| 6,063,053 A | 5/2000 | Castellano et al. |
| 6,074,213 A | 6/2000 | Hon |
| 6,077,106 A | 6/2000 | Mish |
| 6,083,199 A | 7/2000 | Thorley et al. |
| 6,084,526 A | 7/2000 | Blotky et al. |
| 6,086,562 A | 7/2000 | Jacobsen et al. |
| 6,096,002 A | 8/2000 | Landau |
| 6,099,503 A | 8/2000 | Stradella |
| 6,099,504 A | 8/2000 | Gross et al. |
| 6,102,896 A | 8/2000 | Roser |
| 6,119,684 A | 9/2000 | Nöhl et al. |
| 6,120,786 A | 9/2000 | Cheikh |
| 6,123,685 A | 9/2000 | Reynolds |
| 6,149,626 A | 11/2000 | Rachynsky et al. |
| 6,158,613 A | 12/2000 | Novosel et al. |
| 6,161,281 A | 12/2000 | Dando et al. |
| 6,165,155 A | 12/2000 | Jacobsen et al. |
| 6,179,812 B1 | 1/2001 | Botich et al. |
| 6,193,695 B1 | 2/2001 | Rippstein, Jr. |
| 6,202,642 B1 | 3/2001 | McKinnon et al. |
| 6,210,359 B1 | 4/2001 | Patel et al. |
| 6,210,369 B1 | 4/2001 | Wilmot et al. |
| 6,219,587 B1 | 4/2001 | Ahlin et al. |
| 6,221,045 B1 | 4/2001 | Duchon et al. |
| 6,221,055 B1 | 4/2001 | Shaw et al. |
| 6,223,936 B1 | 5/2001 | Jeanbourquin |
| 6,245,046 B1 | 6/2001 | Sibbitt |
| 6,258,063 B1 | 7/2001 | Haar et al. |
| 6,258,068 B1 | 7/2001 | Kirchhofer et al. |
| 6,259,654 B1 | 7/2001 | de la Huerga |
| 6,264,629 B1 | 7/2001 | Landau |
| 6,270,479 B1 | 8/2001 | Bergens et al. |
| 6,280,421 B1 | 8/2001 | Kirchhofer et al. |
| 6,312,412 B1 | 11/2001 | Saied et al. |
| 6,317,630 B1 | 11/2001 | Gross et al. |
| 6,321,942 B1 | 11/2001 | Krampen et al. |
| 6,334,070 B1 | 12/2001 | Nova et al. |
| 6,364,866 B1 | 4/2002 | Furr et al. |
| 6,371,939 B2 | 4/2002 | Bergens et al. |
| 6,383,168 B1 | 5/2002 | Landau et al. |
| 6,387,078 B1 | 5/2002 | Gillespie, III |
| 6,405,912 B2 | 6/2002 | Giannou |
| 6,406,455 B1 | 6/2002 | Willis et al. |
| 6,411,567 B1 | 6/2002 | Niemiec et al. |
| 6,413,236 B1 | 7/2002 | Van Dyke |
| 6,425,499 B1 | 7/2002 | Guiffray |
| 6,425,897 B2 | 7/2002 | Overes et al. |
| 6,427,684 B2 | 8/2002 | Ritsche et al. |
| 6,428,517 B1 | 8/2002 | Hochman et al. |
| 6,428,528 B2 | 8/2002 | Sadowski |
| 6,454,746 B1 | 9/2002 | Bydlon et al. |
| 6,475,181 B1 | 11/2002 | Potter et al. |
| 6,478,771 B1 | 11/2002 | Lavi et al. |
| 6,482,186 B1 | 11/2002 | Douglas et al. |
| 6,494,863 B1 | 12/2002 | Shaw et al. |
| 6,500,150 B1 | 12/2002 | Gross et al. |
| 6,514,230 B1 | 2/2003 | Munk et al. |
| 6,529,446 B1 | 3/2003 | de la Huerga |
| 6,530,900 B1 | 3/2003 | Daily et al. |
| 6,530,904 B1 | 3/2003 | Edwards et al. |
| 6,535,714 B2 | 3/2003 | Melker et al. |
| 6,540,675 B2 | 4/2003 | Aceti et al. |
| 6,544,234 B1 | 4/2003 | Gabriel |
| 6,551,276 B1 | 4/2003 | Mann et al. |
| 6,551,298 B1 | 4/2003 | Zhang |
| 6,554,798 B1 | 4/2003 | Mann et al. |
| 6,558,320 B1 | 5/2003 | Causey, III et al. |
| 6,569,123 B2 | 5/2003 | Alchas |
| 6,572,584 B1 | 6/2003 | Shaw et al. |
| 6,574,166 B2 | 6/2003 | Niemiec |
| 6,575,939 B1 | 6/2003 | Brunel |
| RE38,189 E | 7/2003 | Walker et al. |
| 6,585,685 B2 | 7/2003 | Staylor et al. |
| 6,585,698 B1 | 7/2003 | Packman et al. |
| 6,589,158 B2 | 7/2003 | Winkler |
| 6,595,956 B1 | 7/2003 | Gross et al. |
| 6,597,794 B2 | 7/2003 | Cole et al. |
| 6,599,272 B1 | 7/2003 | Hjertman et al. |
| 6,613,010 B2 | 9/2003 | Castellano |
| 6,616,627 B2 | 9/2003 | Willis et al. |
| 6,633,796 B1 | 10/2003 | Pool et al. |
| 6,641,566 B2 | 11/2003 | Douglas et al. |
| 6,645,171 B1 | 11/2003 | Robinson et al. |
| 6,645,181 B1 | 11/2003 | Lavi et al. |
| 6,648,850 B2 | 11/2003 | Landau |
| 6,656,163 B1 | 12/2003 | Marshall et al. |
| 6,673,035 B1 | 1/2004 | Rice et al. |
| 6,676,630 B2 | 1/2004 | Landau et al. |
| 6,689,093 B2 | 2/2004 | Landau |
| 6,692,469 B1 | 2/2004 | Weekes et al. |
| 6,702,778 B2 | 3/2004 | Hill et al. |
| 6,706,019 B1 | 3/2004 | Parker et al. |
| 6,707,763 B2 | 3/2004 | Osberg et al. |
| 6,708,050 B2 | 3/2004 | Carim |
| 6,708,846 B1 | 3/2004 | Fuchs et al. |
| 6,722,916 B2 | 4/2004 | Buccinna et al. |
| 6,723,077 B2 | 4/2004 | Pickup et al. |
| 6,726,657 B1 | 4/2004 | Dedig et al. |
| 6,726,661 B2 | 4/2004 | Munk et al. |
| 6,736,796 B2 | 5/2004 | Shekalim |
| 6,743,203 B1 | 6/2004 | Pickhard |
| 6,743,635 B2 | 6/2004 | Neel et al. |
| 6,749,437 B2 | 6/2004 | Chan |
| 6,752,781 B2 | 6/2004 | Landau et al. |
| 6,764,469 B2 | 7/2004 | Broselow |
| 6,767,336 B1 | 7/2004 | Kaplan |
| 6,770,052 B2 | 8/2004 | Hill et al. |
| 6,770,056 B2 | 8/2004 | Price et al. |
| 6,783,509 B1 | 8/2004 | Landau et al. |
| 6,786,875 B2 | 9/2004 | Barker et al. |
| 6,793,646 B1 | 9/2004 | Giambattista et al. |
| 6,803,856 B1 | 10/2004 | Murphy et al. |
| 6,805,686 B1 | 10/2004 | Fathallah et al. |
| 6,808,514 B2 | 10/2004 | Schneider et al. |
| 6,809,653 B1 | 10/2004 | Mann et al. |
| 6,817,986 B2 | 11/2004 | Slate et al. |
| 6,830,560 B1 | 12/2004 | Gross et al. |

(56) References Cited

U.S. PATENT DOCUMENTS

| | | |
|---|---|---|
| 6,839,304 B2 | 1/2005 | Niemiec et al. |
| 6,872,200 B2 | 3/2005 | Mann et al. |
| 6,875,195 B2 | 4/2005 | Choi |
| 6,883,222 B2 | 4/2005 | Landau |
| 6,893,420 B2 | 5/2005 | Arnisolle |
| 6,923,764 B2 | 8/2005 | Aceti et al. |
| 6,936,029 B2 | 8/2005 | Mann et al. |
| 6,936,032 B1 | 8/2005 | Bush, Jr. et al. |
| 6,937,150 B2 | 8/2005 | Medema et al. |
| 6,942,646 B2 | 9/2005 | Langley et al. |
| 6,946,299 B2 | 9/2005 | Neel et al. |
| 6,948,492 B2 | 9/2005 | Wermeling et al. |
| 6,949,082 B2 | 9/2005 | Langley et al. |
| 6,952,604 B2 | 10/2005 | DeNuzzio et al. |
| 6,953,445 B2 | 10/2005 | Wilmot et al. |
| 6,953,693 B2 | 10/2005 | Neel et al. |
| 6,958,691 B1 | 10/2005 | Anderson et al. |
| 6,959,247 B2 | 10/2005 | Neel et al. |
| 6,961,285 B2 | 11/2005 | Niemiec et al. |
| 6,964,650 B2 | 11/2005 | Alexandre et al. |
| 6,969,259 B2 | 11/2005 | Pastrick et al. |
| 6,979,316 B1 | 12/2005 | Rubin et al. |
| 6,979,326 B2 | 12/2005 | Mann et al. |
| 6,985,870 B2 | 1/2006 | Martucci et al. |
| 6,997,911 B2 | 2/2006 | Klitmose |
| 7,014,470 B2 | 3/2006 | Vann |
| 7,074,211 B1 | 7/2006 | Heiniger et al. |
| 7,104,972 B2 | 9/2006 | Moller et al. |
| 7,113,101 B2 | 9/2006 | Peterson et al. |
| 7,116,233 B2 | 10/2006 | Zhurin |
| 7,118,553 B2 | 10/2006 | Scherer |
| 7,126,879 B2 | 10/2006 | Snyder |
| 7,158,011 B2 | 1/2007 | Brue |
| 7,237,549 B2 | 7/2007 | Stradella |
| 7,241,278 B2 | 7/2007 | Moller |
| 7,329,241 B2 | 2/2008 | Horvath et al. |
| 7,357,790 B2 | 4/2008 | Hommann et al. |
| 7,416,540 B2 | 8/2008 | Edwards et al. |
| 7,465,294 B1 | 12/2008 | Vladimirsky |
| 7,500,963 B2 | 3/2009 | Westbye et al. |
| 7,500,967 B2 | 3/2009 | Thorley et al. |
| 7,503,907 B1 | 3/2009 | Lesch, Jr. |
| 7,544,188 B2 | 6/2009 | Edwards et al. |
| 7,611,491 B2 | 11/2009 | Pickhard |
| 7,637,891 B2 | 12/2009 | Wall |
| 7,648,482 B2 | 1/2010 | Edwards et al. |
| 7,648,483 B2 | 1/2010 | Edwards et al. |
| 7,654,983 B2 | 2/2010 | De La Serna et al. |
| 7,674,246 B2 | 3/2010 | Gillespie et al. |
| 7,686,788 B2 | 3/2010 | Freyman et al. |
| 7,731,686 B2 | 6/2010 | Edwards et al. |
| 7,731,690 B2 | 6/2010 | Edwards et al. |
| 7,749,194 B2 | 7/2010 | Edwards et al. |
| 7,758,550 B2 | 7/2010 | Bollenbach et al. |
| 7,771,397 B1 | 8/2010 | Olson |
| 7,806,866 B2 | 10/2010 | Hommann et al. |
| 7,850,662 B2 | 12/2010 | Veasey et al. |
| 7,901,377 B1 | 3/2011 | Harrison et al. |
| 7,918,823 B2 | 4/2011 | Edwards et al. |
| 7,918,832 B2 | 4/2011 | Veasey et al. |
| 7,931,614 B2 | 4/2011 | Gonnelli et al. |
| 7,938,802 B2 | 5/2011 | Bicknell et al. |
| 7,947,017 B2 | 5/2011 | Edwards et al. |
| 8,016,788 B2 | 9/2011 | Edwards et al. |
| 8,021,335 B2 | 9/2011 | Lesch, Jr. |
| 8,105,281 B2 | 1/2012 | Edwards |
| 8,105,293 B2 | 1/2012 | Pickhard |
| 8,123,719 B2 | 2/2012 | Edwards et al. |
| 8,162,886 B2 | 4/2012 | Sadowski et al. |
| 8,172,082 B2 | 5/2012 | Edwards et al. |
| 8,206,360 B2 | 6/2012 | Edwards et al. |
| 8,231,573 B2 | 7/2012 | Edwards et al. |
| 8,251,947 B2 | 8/2012 | Kramer et al. |
| 8,276,583 B2 | 10/2012 | Farieta et al. |
| 8,313,466 B2 | 11/2012 | Edwards et al. |
| 8,343,130 B2 | 1/2013 | Green |
| 8,348,096 B2 | 1/2013 | Greiner-Perth |
| 8,361,029 B2 | 1/2013 | Edwards et al. |
| 8,409,141 B2 | 4/2013 | Johansen et al. |
| 8,425,462 B2 | 4/2013 | Edwards et al. |
| 8,567,390 B2 | 10/2013 | Stadelhofer |
| 8,608,698 B2 | 12/2013 | Edwards et al. |
| 8,613,720 B2 | 12/2013 | Bendek et al. |
| 8,632,504 B2 | 1/2014 | Young |
| 8,647,306 B2 | 2/2014 | Schwirtz et al. |
| 8,684,968 B2 | 4/2014 | Genosar |
| 8,690,827 B2 | 4/2014 | Edwards et al. |
| 8,728,042 B2 | 5/2014 | Pickhard |
| 8,734,392 B2 | 5/2014 | Stadelhofer |
| 8,734,394 B2 | 5/2014 | Adams et al. |
| 8,747,357 B2 | 6/2014 | Stamp et al. |
| 8,900,197 B2 | 12/2014 | Crow |
| 8,920,367 B2 | 12/2014 | Edwards et al. |
| 8,920,377 B2 | 12/2014 | Edwards et al. |
| 8,939,959 B2 | 1/2015 | Baney et al. |
| 8,945,048 B2 | 2/2015 | Thorley et al. |
| 8,961,455 B2 | 2/2015 | Holmqvist et al. |
| 8,992,477 B2 | 3/2015 | Raday et al. |
| 9,022,980 B2 | 5/2015 | Edwards et al. |
| 9,056,170 B2 | 6/2015 | Edwards et al. |
| 9,084,849 B2 | 7/2015 | Edwards et al. |
| 9,149,579 B2 | 10/2015 | Edwards et al. |
| 9,173,999 B2 | 11/2015 | Edwards |
| 9,289,563 B2 | 3/2016 | Pickhard et al. |
| 9,345,831 B2 | 5/2016 | Raday et al. |
| 9,586,010 B2 | 3/2017 | Mesa et al. |
| 10,105,499 B2 | 10/2018 | Schwirtz et al. |
| 10,398,838 B2 | 9/2019 | Tremblay et al. |
| 2001/0005781 A1 | 6/2001 | Bergens et al. |
| 2001/0037087 A1 | 11/2001 | Knauer |
| 2002/0055711 A1 | 5/2002 | Lavi et al. |
| 2002/0076679 A1 | 6/2002 | Aman |
| 2002/0095120 A1 | 7/2002 | Larsen et al. |
| 2002/0096543 A1 | 7/2002 | Juselius |
| 2002/0189612 A1 | 12/2002 | Rand |
| 2003/0015191 A1 | 1/2003 | Armstrong et al. |
| 2003/0028145 A1 | 2/2003 | Duchon et al. |
| 2003/0040717 A1 | 2/2003 | Saulenas et al. |
| 2003/0105430 A1 | 6/2003 | Lavi et al. |
| 2003/0106824 A1 | 6/2003 | Wilmot et al. |
| 2003/0120222 A1 | 6/2003 | Vaillancourt |
| 2003/0132128 A1 | 7/2003 | Mazur |
| 2003/0233070 A1 | 12/2003 | De La Serna et al. |
| 2004/0019326 A1 | 1/2004 | Gilbert et al. |
| 2004/0024361 A1 | 2/2004 | Fago et al. |
| 2004/0024367 A1 | 2/2004 | Gilbert |
| 2004/0039336 A1 | 2/2004 | Amark et al. |
| 2004/0039337 A1 | 2/2004 | Letzing |
| 2004/0039368 A1 | 2/2004 | Reilly et al. |
| 2004/0054327 A1 | 3/2004 | Gillespie, III |
| 2004/0073169 A1 | 4/2004 | Amisar et al. |
| 2004/0092874 A1 | 5/2004 | Mazidji et al. |
| 2004/0092875 A1 | 5/2004 | Kochamba |
| 2004/0094146 A1 | 5/2004 | Schiewe et al. |
| 2004/0116854 A1 | 6/2004 | Abulhaj et al. |
| 2004/0138611 A1 | 7/2004 | Griffiths et al. |
| 2004/0143298 A1 | 7/2004 | Nova et al. |
| 2004/0159364 A1 | 8/2004 | Landau et al. |
| 2004/0210199 A1 | 10/2004 | Atterbury et al. |
| 2004/0220524 A1 | 11/2004 | Sadowski et al. |
| 2004/0249358 A1 | 12/2004 | McWethy et al. |
| 2004/0267204 A1 | 12/2004 | Brustowicz |
| 2005/0027255 A1 | 2/2005 | Lavi et al. |
| 2005/0033234 A1 | 2/2005 | Sadowski et al. |
| 2005/0033386 A1 | 2/2005 | Osborn et al. |
| 2005/0049561 A1 | 3/2005 | Hommann et al. |
| 2005/0062603 A1 | 3/2005 | Fuerst et al. |
| 2005/0090781 A1 | 4/2005 | Baba et al. |
| 2005/0090782 A1 | 4/2005 | Marshall et al. |
| 2005/0101912 A1 | 5/2005 | Faust et al. |
| 2005/0134433 A1 | 6/2005 | Sweeney, II |
| 2005/0148931 A1 | 7/2005 | Juhasz |
| 2005/0148945 A1 | 7/2005 | Chen |
| 2005/0159705 A1 | 7/2005 | Crawford et al. |

(56) References Cited

U.S. PATENT DOCUMENTS

| | | |
|---|---|---|
| 2005/0165360 A1 | 7/2005 | Stamp |
| 2005/0171477 A1* | 8/2005 | Rubin .................. A61M 5/326 604/156 |
| 2005/0182358 A1 | 8/2005 | Veit et al. |
| 2005/0183982 A1 | 8/2005 | Giewercer |
| 2005/0192530 A1 | 9/2005 | Castellano |
| 2005/0197654 A1 | 9/2005 | Edman et al. |
| 2005/0203466 A1 | 9/2005 | Hommann et al. |
| 2005/0222539 A1 | 10/2005 | Gonzales et al. |
| 2005/0261742 A1 | 11/2005 | Nova et al. |
| 2005/0267403 A1 | 12/2005 | Landau et al. |
| 2005/0273059 A1 | 12/2005 | Mernoe et al. |
| 2005/0277891 A1 | 12/2005 | Sibbitt |
| 2006/0030819 A1 | 2/2006 | Young et al. |
| 2006/0053036 A1 | 3/2006 | Coffman et al. |
| 2006/0058848 A1 | 3/2006 | Piraino et al. |
| 2006/0069350 A1 | 3/2006 | Buenger et al. |
| 2006/0074519 A1 | 4/2006 | Barker et al. |
| 2006/0084908 A1 | 4/2006 | Bonney et al. |
| 2006/0111666 A1 | 5/2006 | Hommann et al. |
| 2006/0111671 A1 | 5/2006 | Klippenstein |
| 2006/0129089 A1 | 6/2006 | Stamp |
| 2006/0129090 A1 | 6/2006 | Moberg et al. |
| 2006/0173408 A1 | 8/2006 | Wyrick |
| 2006/0184133 A1 | 8/2006 | Pessin |
| 2006/0189938 A1 | 8/2006 | Hommann et al. |
| 2006/0200077 A1 | 9/2006 | Righi et al. |
| 2006/0204939 A1 | 9/2006 | Bardsley et al. |
| 2006/0223027 A1 | 10/2006 | Smith et al. |
| 2006/0235354 A1 | 10/2006 | Kaal et al. |
| 2006/0247579 A1 | 11/2006 | Friedman |
| 2006/0265186 A1 | 11/2006 | Holland et al. |
| 2007/0008113 A1 | 1/2007 | Spoonhower et al. |
| 2007/0056585 A1 | 3/2007 | Davies et al. |
| 2007/0074722 A1 | 4/2007 | Giroux et al. |
| 2007/0100288 A1 | 5/2007 | Bozeman et al. |
| 2007/0129686 A1 | 6/2007 | Daily et al. |
| 2007/0135767 A1 | 6/2007 | Gillespie et al. |
| 2007/0173772 A1 | 7/2007 | Liversidge |
| 2007/0184847 A1 | 8/2007 | Hansen et al. |
| 2007/0202163 A1 | 8/2007 | Rawas-Qalaji et al. |
| 2007/0203247 A1* | 8/2007 | Phillips ................ A61K 31/137 514/649 |
| 2007/0210147 A1 | 9/2007 | Morrone et al. |
| 2007/0213598 A1 | 9/2007 | Howard et al. |
| 2007/0265568 A1 | 11/2007 | Tsals et al. |
| 2008/0147006 A1 | 6/2008 | Brunnberg et al. |
| 2008/0154200 A1 | 6/2008 | Lesch |
| 2008/0171995 A1 | 7/2008 | Vitullo et al. |
| 2008/0188798 A1 | 8/2008 | Weber |
| 2008/0208114 A1 | 8/2008 | Landau et al. |
| 2008/0228143 A1 | 9/2008 | Stamp |
| 2008/0255513 A1 | 10/2008 | Kaal et al. |
| 2008/0262443 A1 | 10/2008 | Hommann et al. |
| 2008/0269347 A1 | 10/2008 | Bruss et al. |
| 2009/0005735 A1 | 1/2009 | Wikner et al. |
| 2009/0093759 A1 | 4/2009 | Judd et al. |
| 2009/0192486 A1 | 7/2009 | Wilmot et al. |
| 2009/0221962 A1 | 9/2009 | Kaal et al. |
| 2009/0240200 A1 | 9/2009 | Heneveld et al. |
| 2009/0318361 A1 | 12/2009 | Noera et al. |
| 2010/0010454 A1 | 1/2010 | Marshall et al. |
| 2010/0049125 A1 | 2/2010 | James et al. |
| 2010/0137808 A1 | 6/2010 | Wilmot et al. |
| 2010/0152659 A1 | 6/2010 | Streit et al. |
| 2010/0160894 A1 | 6/2010 | Julian et al. |
| 2010/0185148 A1 | 7/2010 | Gillespie, III et al. |
| 2010/0185178 A1 | 7/2010 | Sharp et al. |
| 2010/0212663 A1 | 8/2010 | Vedrine et al. |
| 2010/0280460 A1 | 11/2010 | Markussen |
| 2010/0286612 A1 | 11/2010 | Cirillo |
| 2011/0060274 A1 | 3/2011 | Kuhn |
| 2011/0077589 A1 | 3/2011 | Karlsson et al. |
| 2011/0092954 A1 | 4/2011 | Jennings |
| 2011/0098655 A1 | 4/2011 | Jennings et al. |
| 2011/0104206 A1* | 5/2011 | Nanduri ................ A61K 47/38 424/239.1 |
| 2011/0201999 A1 | 8/2011 | Cronenberg |
| 2011/0202011 A1 | 8/2011 | Wozencroft |
| 2011/0213314 A1 | 9/2011 | Guillermo |
| 2011/0245761 A1 | 10/2011 | Jennings et al. |
| 2011/0270020 A1 | 11/2011 | Genosar |
| 2011/0295215 A1 | 12/2011 | Nielsen et al. |
| 2012/0046613 A1 | 2/2012 | Plumptre |
| 2012/0056019 A1 | 3/2012 | Renz et al. |
| 2012/0101446 A1 | 4/2012 | Heald |
| 2012/0101475 A1* | 4/2012 | Wilmot ................ A61M 5/2033 604/506 |
| 2012/0107783 A1 | 5/2012 | Julian et al. |
| 2012/0116319 A1 | 5/2012 | Grunhut |
| 2012/0125951 A1 | 5/2012 | Leak et al. |
| 2012/0130318 A1 | 5/2012 | Young |
| 2012/0143144 A1 | 6/2012 | Young |
| 2012/0172804 A1 | 7/2012 | Plumptre |
| 2012/0172817 A1 | 7/2012 | Bruggemann et al. |
| 2012/0191049 A1 | 7/2012 | Harms et al. |
| 2012/0209200 A1 | 8/2012 | Jones et al. |
| 2012/0233834 A1 | 9/2012 | Szechinski et al. |
| 2012/0238960 A1 | 9/2012 | Smith et al. |
| 2012/0253288 A1 | 10/2012 | Dasbach et al. |
| 2012/0259285 A1 | 10/2012 | Schabbach et al. |
| 2012/0271243 A1 | 10/2012 | Plumptre et al. |
| 2012/0283648 A1 | 11/2012 | Veasey et al. |
| 2012/0283651 A1 | 11/2012 | Veasey et al. |
| 2012/0283662 A1 | 11/2012 | MacDonald et al. |
| 2012/0289906 A1 | 11/2012 | Jones et al. |
| 2012/0289929 A1 | 11/2012 | Boyd et al. |
| 2012/0310168 A1 | 12/2012 | Plumptre et al. |
| 2012/0310206 A1 | 12/2012 | Kouyoumjian et al. |
| 2012/0323186 A1 | 12/2012 | Karlsen et al. |
| 2012/0325865 A1 | 12/2012 | Forstreuter et al. |
| 2012/0330244 A1 | 12/2012 | Helmer et al. |
| 2013/0060231 A1 | 3/2013 | Adlon et al. |
| 2013/0060232 A1 | 3/2013 | Adlon et al. |
| 2013/0079718 A1 | 3/2013 | Shang et al. |
| 2013/0096512 A1 | 4/2013 | Ekman et al. |
| 2013/0110050 A1 | 5/2013 | Boyd et al. |
| 2013/0131602 A1 | 5/2013 | Kemp et al. |
| 2013/0138049 A1 | 5/2013 | Kemp et al. |
| 2013/0150800 A1 | 6/2013 | Kemp et al. |
| 2013/0172822 A1 | 7/2013 | Ekman et al. |
| 2013/0204199 A1 | 8/2013 | Hourmand et al. |
| 2013/0218074 A1 | 8/2013 | Holmqvist et al. |
| 2013/0226084 A1 | 8/2013 | Samandi et al. |
| 2013/0236872 A1 | 9/2013 | Laurusonis et al. |
| 2013/0245562 A1 | 9/2013 | Kouyoumjian et al. |
| 2013/0266919 A1 | 10/2013 | Baker et al. |
| 2013/0274662 A1 | 10/2013 | Hourmand et al. |
| 2013/0274707 A1 | 10/2013 | Wilmot et al. |
| 2013/0296796 A1 | 11/2013 | Hourmand et al. |
| 2013/0317427 A1 | 11/2013 | Brereton et al. |
| 2013/0317477 A1 | 11/2013 | Edwards et al. |
| 2013/0317480 A1 | 11/2013 | Reber et al. |
| 2014/0025014 A1 | 1/2014 | Radmer et al. |
| 2014/0031760 A1 | 1/2014 | Mercer et al. |
| 2014/0046259 A1 | 2/2014 | Reber et al. |
| 2014/0081234 A1 | 3/2014 | Eggert et al. |
| 2014/0103075 A1 | 4/2014 | Bennison et al. |
| 2014/0114250 A1 | 4/2014 | DeSalvo et al. |
| 2014/0128840 A1 | 5/2014 | Rao et al. |
| 2014/0135705 A1 | 5/2014 | Hourmand et al. |
| 2014/0257185 A1 | 9/2014 | Bechmann et al. |
| 2014/0257241 A1 | 9/2014 | Sutkin et al. |
| 2015/0005356 A1 | 1/2015 | Fleming |
| 2015/0011973 A1* | 1/2015 | Edwards ............. A61M 5/2033 604/506 |
| 2015/0051538 A1 | 2/2015 | Hata et al. |
| 2015/0165129 A1 | 6/2015 | Row et al. |
| 2015/0174325 A1 | 6/2015 | Young et al. |
| 2015/0238695 A1 | 8/2015 | Edwards et al. |
| 2015/0283323 A1 | 10/2015 | Young et al. |
| 2016/0015895 A1* | 1/2016 | Blondino ............ A61M 5/2033 604/506 |
| 2016/0015907 A1 | 1/2016 | Edwards et al. |

(56) References Cited

U.S. PATENT DOCUMENTS

| | | |
|---|---|---|
| 2016/0022909 A1 | 1/2016 | Edwards et al. |
| 2016/0045670 A1 | 2/2016 | Edwards et al. |
| 2016/0074584 A1 | 3/2016 | Carmel et al. |
| 2016/0114110 A1 | 4/2016 | Kerns |
| 2016/0121056 A1 | 5/2016 | Edwards et al. |
| 2016/0157816 A1 | 6/2016 | Denny |
| 2016/0184521 A1 | 6/2016 | Edwards et al. |
| 2016/0193412 A1 | 7/2016 | Cereda et al. |
| 2016/0250414 A1 | 9/2016 | Edwards et al. |
| 2016/0296716 A1 | 10/2016 | Cabiri et al. |
| 2016/0354556 A1 | 12/2016 | Zucker et al. |
| 2017/0246393 A1 | 8/2017 | Genosar |
| 2017/0290982 A1 | 10/2017 | Edwards et al. |
| 2018/0158374 A1* | 6/2018 | Zamierowski ....... G09B 23/303 |
| 2018/0296760 A1 | 10/2018 | Csenar et al. |
| 2018/0304017 A1 | 10/2018 | Edwards et al. |
| 2018/0304018 A1* | 10/2018 | Blondino ................ A61M 5/28 |
| 2019/0009025 A1 | 1/2019 | Chakrabarti et al. |
| 2019/0009027 A1 | 1/2019 | Edwards et al. |
| 2019/0151548 A1 | 5/2019 | Edwards et al. |
| 2019/0175837 A1 | 6/2019 | Edwards et al. |
| 2019/0275253 A1 | 9/2019 | Edwards et al. |
| 2019/0282763 A1 | 9/2019 | Edwards et al. |
| 2019/0328971 A1 | 10/2019 | Edwards et al. |
| 2019/0381245 A1 | 12/2019 | Edwards et al. |
| 2020/0001010 A1 | 1/2020 | Anderson et al. |

FOREIGN PATENT DOCUMENTS

| | | |
|---|---|---|
| EP | 1462134 A1 | 9/2004 |
| EP | 1518575 A1 | 3/2005 |
| EP | 1712178 A2 | 10/2006 |
| FR | 1514210 | 2/1968 |
| FR | 2506161 | 11/1982 |
| FR | 2509615 | 1/1983 |
| FR | 2700959 | 2/1993 |
| GB | 2490807 | 11/2012 |
| JP | 7-37194 | 11/1995 |
| WO | WO 91/04760 | 4/1991 |
| WO | WO 93/02720 | 2/1993 |
| WO | WO 95/13838 | 5/1995 |
| WO | WO 95/26009 | 9/1995 |
| WO | WO 95/35126 | 12/1995 |
| WO | WO 98/52632 | 11/1998 |
| WO | WO 99/10031 | 3/1999 |
| WO | WO 2001/024690 | 4/2001 |
| WO | WO 2001/026020 | 4/2001 |
| WO | WO 2001/041849 | 6/2001 |
| WO | WO 2001/088828 | 11/2001 |
| WO | WO 2001/093926 | 12/2001 |
| WO | WO 2002/083205 | 10/2002 |
| WO | WO 2002/083212 | 10/2002 |
| WO | WO 2003/011378 | 2/2003 |
| WO | WO 2003/013632 | 2/2003 |
| WO | WO 2003/095001 | 11/2003 |
| WO | WO 2003/097133 | 11/2003 |
| WO | WO 2004/047890 | 6/2004 |
| WO | WO 2004/047891 | 6/2004 |
| WO | WO 2004/047892 | 6/2004 |
| WO | WO 2004/047893 | 6/2004 |
| WO | WO 2004/054644 | 7/2004 |
| WO | WO 2005/050526 | 6/2005 |
| WO | WO 2005/070481 | 8/2005 |
| WO | WO 2005/077441 | 8/2005 |
| WO | WO 2006/109778 | 10/2006 |
| WO | WO 2006/125692 | 11/2006 |
| WO | WO 2007/083115 | 7/2007 |
| WO | WO 2008/005315 | 1/2008 |
| WO | WO 2008/148864 | 12/2008 |
| WO | WO 2010/033806 | 3/2010 |
| WO | WO 2012/164402 A2 | 12/2012 |
| WO | WO 2013/044172 | 3/2013 |
| WO | WO 2016/154427 A2 | 9/2016 |
| WO | WO 2017/033193 A2 | 3/2017 |
| WO | WO 2017/034618 A1 | 3/2017 |
| WO | WO 2017/210011 | 12/2017 |
| WO | WO 2018/078121 | 5/2018 |

OTHER PUBLICATIONS

"Insect Stings Auto-injector Pouches and Carry Cases," The Insect Stings On-Line Shop, [online] [retrieved on Jan. 24, 2007] Retrieved from the Internet <URL: http://www.insectstings.co.uk/acatalog/Auto Injector Pouches.html>, 3 pages.

"Anaphylaxis Canada Product Catalogue," Anaphylaxis Canada > Living with Anaphylaxis > Tools and Resources [online] [retrieved on Jan. 24, 2007] Retrieved from the Internet <URL: http://anaphylaxis.org/content/livingwith/product catalogue.asp >, 9 pages.

Ruppar, D., "Implant Technologies Expected to Remain a Niche but Effective Method of Drug Delivery," Drug Delivery Technology, Feb. 2007, vol. 7, No. 2 [online] [retrieved on Jun. 1, 2007] Retrieved from the Internet <URL: http://www.drugdeliverytech-.

O'Hagan, D. et al., "Novel approaches to pediatric vaccine delivery," Advanced Drug Delivery Reviews, 58:29-51 (2006).

Meridian Medical Technologies, Inc., "Pralidoxime Chloride Trainer," 2006. [retrieved on Feb. 16, 2007] Retrieved from the Internet <URL: http://www.meridianmeds.com/auto-injectors/2pamcl_trainer.html/>, 1 pages.

Gosbee, L. L., "Nuts! I Can't Figure Out How to Use My Life-Saving Epinephrine Auto-Injector," Joint Commision Journal on Quality and Safety, 30(4):220-223 (Apr. 2004).

Amgen, "Using Aranesp prefilled SureClick autoinjector is a simple 3-step process," 2006. [retrieved on Feb. 16, 2007] Retrieved from the Internet <URL: http://www.aranesp.com/patient/cia/sureclick/using_three_steps.jsp/>, 4 pages.

BD Accuspray™ Nasal Spray System, 2004, Retrieved from the Internet <URL: http://www.bd.com/press/pdfs/flu/bd_accuspray.pdf>, 1 page.

Simons, F. E. R. et al., "Epinephrine absorption in adults: intramuscular versus subcutaneous injection," J Allergy Clin Immunol, 108(5), 871-873 (2001).

Kim, Harold et al., "Inadequacy of current pediatric epinephrine autoinjector needle length for use in infants and toddlers,"Ann. Alergy Asthma Immunology vol. 118, pp. 719-725 (Jun. 2017).

Kim, Laura et al., "Children under 15 kg with food allergies may be at risk of having epinephrine auto-injectors administered into bone," Allergy, Asthma and Clinical Immunology, vol. 10:40, 6 pages (2014).

Robinson, Martha Wortham, "Guide to I.M. injections in newborns," Nursing made incredibly easy! <http://www.nursingmadeincrediblyeasy.com> pp. 14-17 (Sep./Oct. 2010).

"How to Administer IM (Intramuscular) Injections," Minnesota Department of Health, 2 pages (Jun. 2001).

Kas, C. "How to Administer an EpiPen Jr. to a toddler," [online] Apr. 19, 2015 [retrieved on Feb. 9, 2018] Retrieved from the Internet <https://www.youtube.com/watch?v=81acpicUrec>.

AUVI-Q® (epinephrine) Injection, USP. Drug Description [online]. RxList, 2016 [retrieved on Feb. 13, 2018]. Retrieved from the Internet. <https://www.rxlist.com/auvi-q-drug.htm>.

Sicherer, SH et al. Self-Injectable Epinephrine for First-Aid Management of Anaphylaxis. Pediatrics, vol. 119, Issue 3, Mar. 2007, pp. 638-646 [online], retrieved on Feb. 7, 2018. Retrieved from the internet. <http://pediatrics.aapublications.org/content/119/3/638> <DOI: 10.1542/peds.2006-3689>.

Office Action for Canadian Patent Application No. 2,586,525, dated Aug. 17, 2010.

Examination Report for British Patent Application No. GB 0708523.6, dated Dec. 8, 2008.

Office Action for JP2007-543005, dated Feb. 1, 2010.

Examination Report for British Patent Application No. GB 0822532.8, dated Jan. 21, 2009.

Examination Report for British Patent Application No. GB 0822532.8, dated May 21, 2009.

Office Action for U.S. Appl. No. 11/562,061, dated Feb. 3, 2009.

Office Action for U.S. Appl. No. 11/566,422, dated Jul. 6, 2010.

Office Action for U.S. Appl. No. 11/566,422, dated Dec. 3, 2010.

(56) References Cited

OTHER PUBLICATIONS

Office Action for Japanese Patent Application No. 2009-537380, dated Jun. 15, 2012.
Office Action for U.S. Appl. No. 11/758,393, dated May 13, 2009.
Search Report and Written Opinion for International Patent Application No. PCT/US07/84891 dated Sep. 15, 2008, 7 pages.
Office Action for U.S. Appl. No. 12/138,987, dated Oct. 5, 2009.
Office Action for U.S. Appl. No. 13/090,392, dated Feb. 29, 2012.
International Search Report and Written Opinion for International Patent Application No. PCT/US06/03415, dated Jul. 13, 2006, 10 pages.
Office Action for Canadian Patent Application No. 2,762,072, dated Mar. 14, 2016.
Third Party Observations filed in European Patent Application No. 07864490.3, dated Aug. 22, 2016.
Office Action for U.S. Appl. No. 14/731,048, dated Oct. 19, 2016.
Office Action for U.S. Appl. No. 15/696,287, dated Nov. 16, 2017.
International Search Report and Written Opinion for International Application No. PCT/US2017/067873, dated Apr. 25, 2018.
Office Action for U.S. Appl. No. 16/162,552, dated Sep. 17, 2019.

* cited by examiner

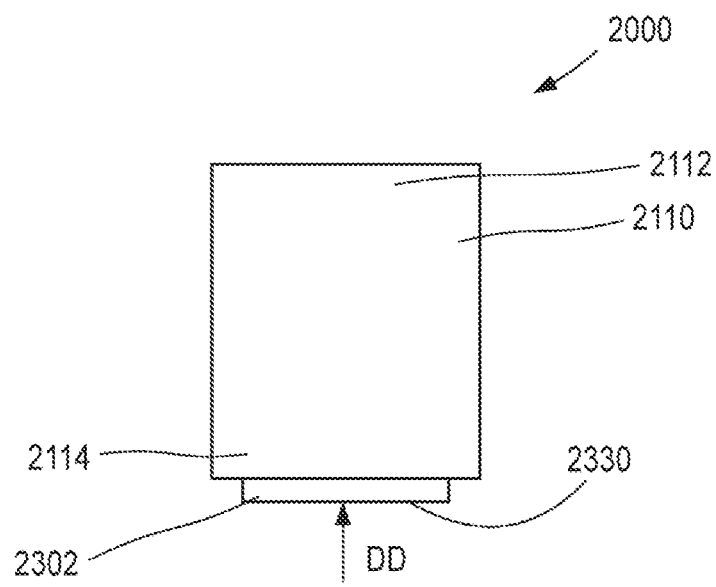
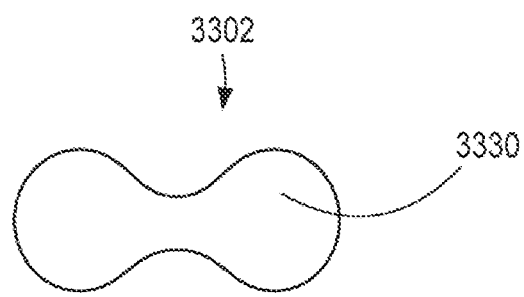
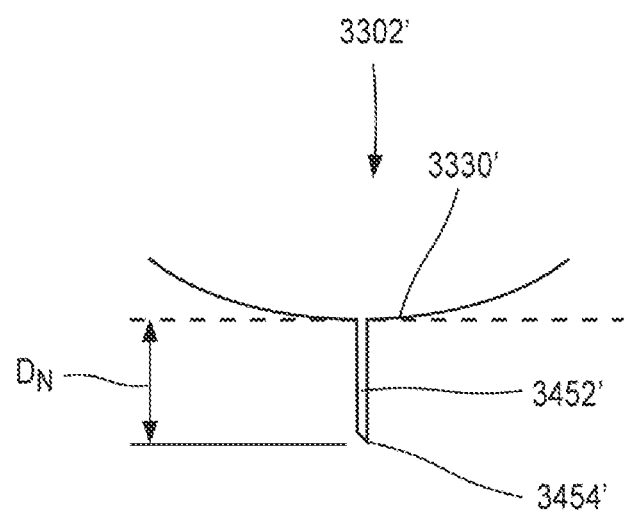

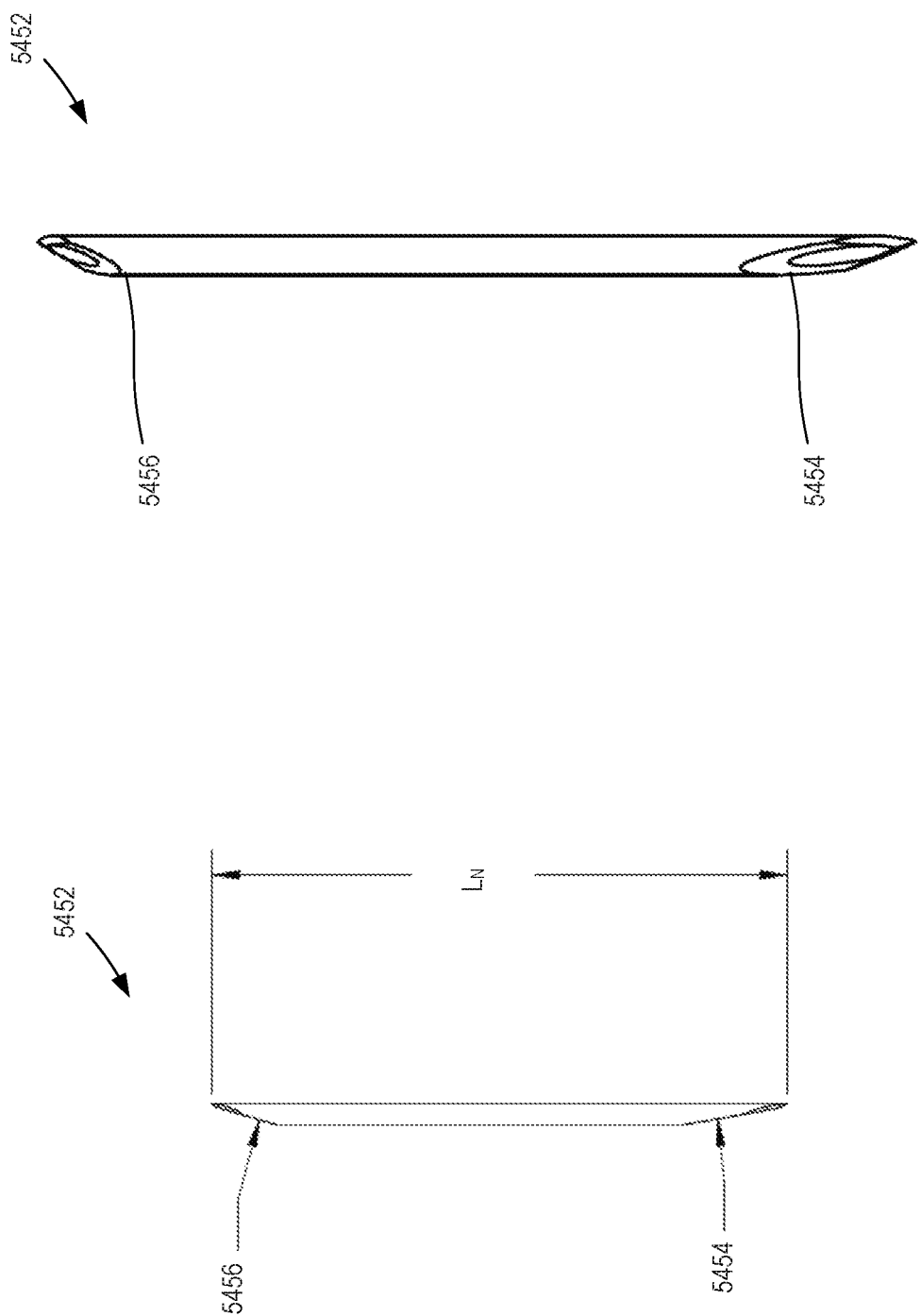

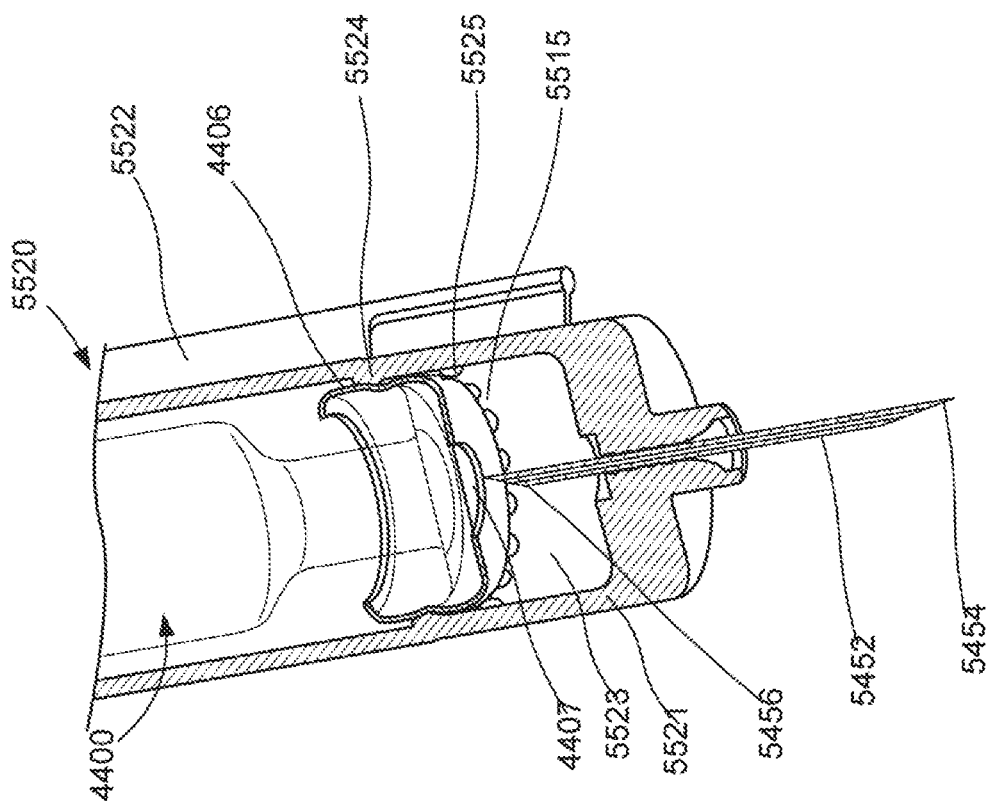
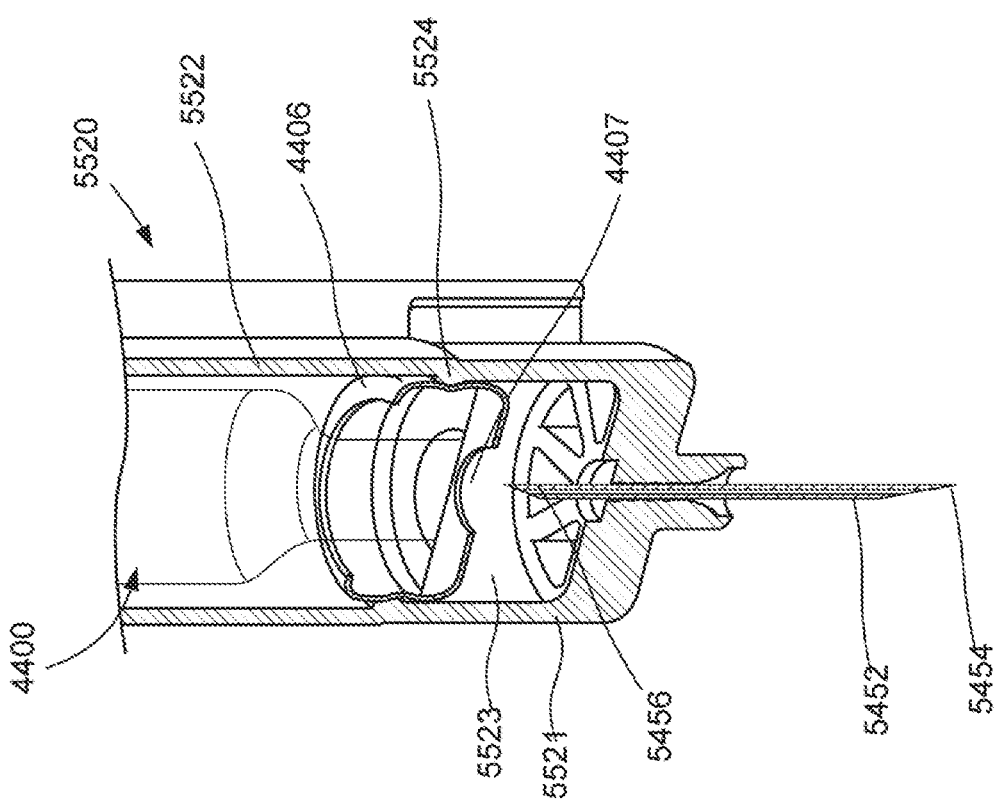

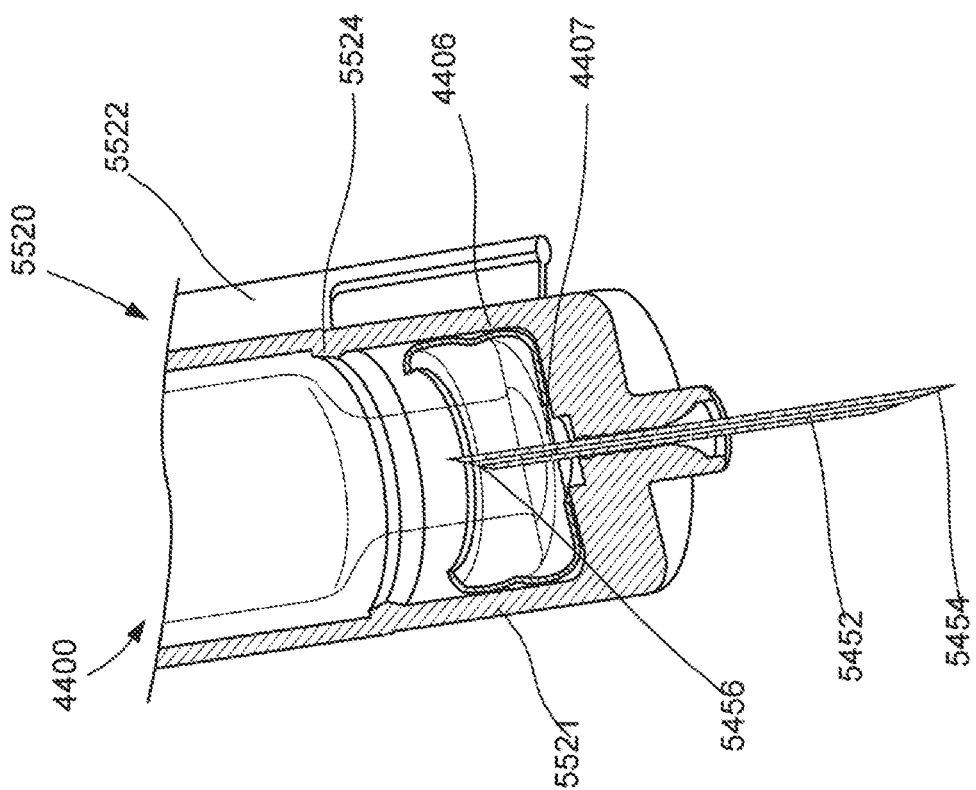
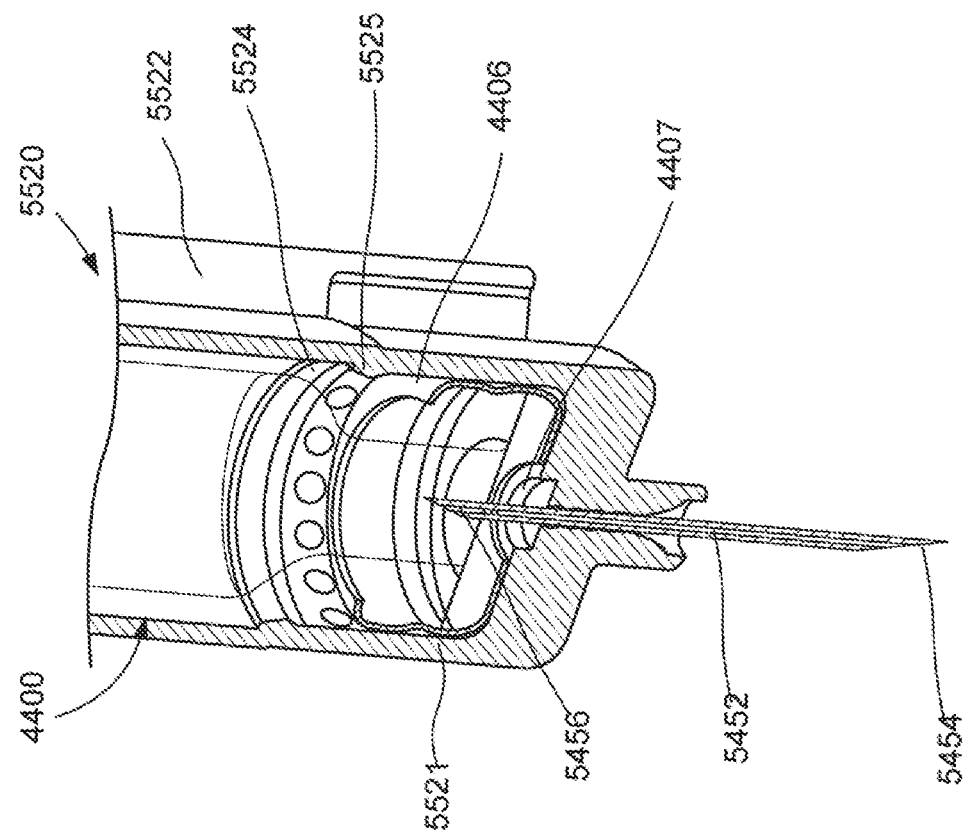

MEDICAMENT DELIVERY DEVICE AND METHODS FOR DELIVERING DRUGS TO INFANTS AND CHILDREN

CROSS-REFERENCE TO RELATED APPLICATIONS

This application is a U.S. national stage filing under 35 U.S.C. § 371 of International Application No. PCT/US17/67873, entitled "MEDICAMENT DELIVERY DEVICE AND METHODS FOR DELIVERING DRUGS TO INFANTS AND CHILDREN," filed Dec. 21, 2017, which claims benefit of priority to U.S. Provisional Application Ser. No. 62/438,584, entitled "Medicament Delivery Device and Methods for Delivering Drugs to Infants and Children," filed Dec. 23, 2016, the entire disclosure of each of which is incorporated herein by reference in its entirety.

BACKGROUND

The embodiments described herein relate generally to medical devices and pharmaceutical compositions, and more particularly to a medicament delivery device for delivery of drugs to infants and children.

Exposure to certain substances, such as, for example, peanuts, shellfish, bee venom, certain drugs, toxins, and the like, can cause allergic reactions in some individuals. Such allergic reactions can, at times, lead to anaphylactic shock, which can cause a sharp drop in blood pressure, hives, and/or severe airway constriction. Accordingly, responding rapidly to mitigate the effects from such exposures can prevent injury and/or death. For example, in certain situations, an injection of epinephrine (i.e., adrenaline) can provide substantial and/or complete relief from the allergic reaction. In other situations, for example, an injection of an antidote to a toxin can greatly reduce and/or eliminate the harm potentially caused by the exposure. Because emergency medical facilities may not be available when an individual is suffering from an allergic reaction, some individuals carry a medicament delivery device, such as, for example, an auto-injector, to rapidly self-administer (or to have a care giver administer) a medicament in response to an allergic reaction. Moreover, even within a medical facility (e.g., a hospital, doctor's office, clinic, or the like) automatic delivery devices can be advantageous. Specifically, such devices include a predetermined dosage that is appropriate for the patient, and provide a method for repeatably and reliably delivering the dose. Accordingly, there are many known devices for automatically delivering epinephrine.

Some known devices for automatically delivering epinephrine, such as the Epipen®, include a needle that is automatically inserted into the body and through which the dose is injected into the patient. Such known devices target intramuscular delivery of the epinephrine (e.g., delivery into the thigh muscle). In fact, some studies have shown that subcutaneous delivery of epinephrine can reduce the efficacy of the dose. Moreover, some studies have shown that intravenous delivery of epinephrine can not only reduce the efficacy, but also can result in cardiovascular complications (e.g., a rapid rise in blood pressure and increased heart rate). In addition to concerns with subcutaneous and intravenous delivery, intraosseous delivery of epinephrine is also undesirable.

Known auto-injectors include devices tailored for both adult use and pediatric use. In particular, known adult-use auto-injectors typically include a dose of 0.3 mg epinephrine, and are used for patients weighing greater than 30 kg. The exposed needle length for such known adult-use auto-injectors ranges from about 16 mm to greater than 20 mm. Known pediatric auto-injectors typically include a dose of 0.15 mg epinephrine, and are used for patients weighing between about 15 kg and 30 kg. Such known pediatric-use auto-injectors typically have a shorter exposed needle length to accommodate the smaller size of the patient—often between 12.7 mm and 16 mm. Currently, however, there are no known devices for automatically injecting epinephrine into infants and small children weighing less than 15 kg.

Because there are no products available for use with this patient population, in certain instances a pediatric-use auto-injector may be used with a child weighing less than 15 kg. Such use, however, can present complications due to the possibility of overdosing the patient. Further complicating this concern is the fact that the dose accuracy for a device intended to deliver 0.3 mL (or 0.15 mL for a pediatric version) may not be adequate for a patient weighing less than 15 kg. More particularly, the volumetric tolerance for a device configured to deliver 0.3 mL with an accuracy of ±15 percent is ±0.045 ml. This volumetric tolerance may not be sufficient for patient weighing less than 15 kg.

Another concern with using an auto-injector intended for patients weighing more than 15 kg is the possibility that the dose will be delivered to an improper location within the body. In particular, because the distance between the skin and the muscle layer (referred to herein as the skin-to-muscle distance) and between the skin and the bone (e.g., the femur, referred to herein as the skin-to-bone distance) is different for patients weighing less than 15 kg than it is for larger patients, the use of a device intended for larger patients may result in intraosseous delivery in an unacceptable number of patients. If the exposed needle length is made too short, however, then undesirable subcutaneous delivery may also occur in an unacceptable number of patients.

Thus, a need exists for improved methods and devices for delivering drugs, and in particular, epinephrine, to infants and children weighing less than 15 kg. Additionally, a need exists for an epinephrine auto-injector having improved accuracy.

SUMMARY

Medicament delivery devices and methods for administration of epinephrine are described herein. In some embodiments, a method of delivering epinephrine includes placing a distal end surface of a medical injector into contact with a target location of a patient. The medical injector includes a housing, an energy storage member and a medicament container containing a dose of epinephrine effective for administration to the patient experiencing anaphylaxis and having a weight of less than 15 kg. The medicament container is coupled to a needle. The medical injector is actuated after the placing such that the energy storage member produces a force to move the needle from a first needle position to a second needle position. A distal tip of the needle extends from the distal end surface by a distance of between 7 millimeters and 8 millimeters when the needle is in the second needle position. A portion of the force is exerted to expel the dose of epinephrine from the medicament container when the needle is in the second position.

In some embodiments, an apparatus includes a housing, a contact surface, a medicament container, an energy storage member, and an actuator. The contact surface is coupled to the housing, and is configured to contact a target location of a patient. The medicament container is at least partially disposed within the housing, and contains a dose of epinephrine effective for administration to the patient experiencing anaphylaxis and having a weight of less than 15 kg. The medicament container coupled to a needle. The energy storage member is within the housing, and produces a force to move the needle from a first needle position to a second needle position. A distal tip of the needle extending from the contact surface by a distance of between about 6.35 millimeters and 9 millimeters when the needle is in the second needle position. The actuator is configured to actuate the energy storage member to release the force.

BRIEF DESCRIPTION OF THE DRAWINGS

FIG. 5 is a schematic illustration of a medicament delivery device, according to an embodiment.

FIG. 6 is a schematic illustration of a bottom view of a contact surface of a medicament delivery device according to an embodiment.

FIG. 7 is a schematic illustration of a side view of a contact surface of a medicament delivery device according to an embodiment.

FIGS. 51 and 52 are a side view and a perspective view, respectively, of a needle according to an embodiment.

FIGS. 57-58 are perspective cross-sectional views of the carrier assembly shown in FIG. 54 and a medicament container in a first configuration.

FIGS. 59-60 are perspective cross-sectional views of the carrier assembly shown in FIG. 54 and a medicament container in a second configuration.

DETAILED DESCRIPTION

Figure 1:
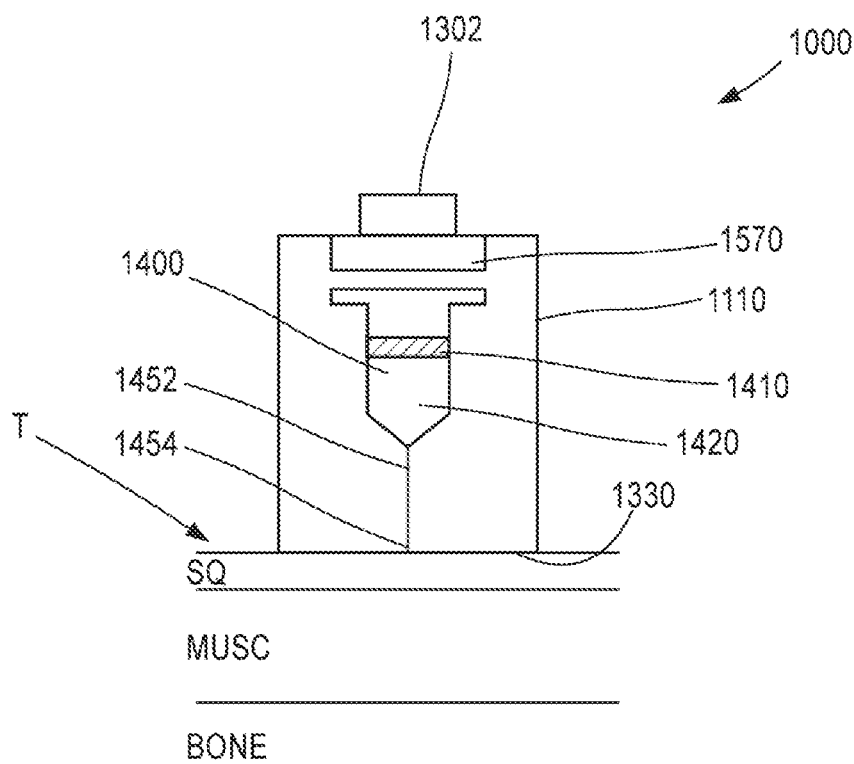
FIGS. 1-4 are schematic illustrations of a medicament delivery device according to an embodiment, in a first configuration, second configuration, third configuration, and fourth configuration, respectively.

Medicament delivery devices and methods for administration of epinephrine are described herein. In some embodiments, a method of delivering epinephrine includes placing a distal end surface of a medical injector into contact with a target location of a patient. The medical injector includes a housing, an energy storage member and a medicament container containing a dose of epinephrine effective for administration to the patient experiencing anaphylaxis and having a weight of less than 15 kg. The medicament container is coupled to a needle. The medical injector is actuated after the placing such that the energy storage member produces a force to move the needle from a first needle position to a second needle position. A distal tip of the needle extends from the distal end surface by a distance of between 7 millimeters and 8 millimeters when the needle is in the second needle position. A portion of the force is exerted to expel the dose of epinephrine from the medicament container when the needle is in the second position.

In some embodiments, an apparatus includes a housing, a contact surface, a medicament container, an energy storage member, and an actuator. The contact surface is coupled to the housing, and is configured to contact a target location of a patient. The medicament container is at least partially disposed within the housing, and contains a dose of epinephrine effective for administration to the patient experiencing anaphylaxis and having a weight of less than 15 kg. The medicament container coupled to a needle. The energy storage member is within the housing, and produces a force to move the needle from a first needle position to a second needle position. A distal tip of the needle extending from the contact surface by a distance of between about 6.35 millimeters and 9 millimeters when the needle is in the second needle position. The actuator is configured to actuate the energy storage member to release the force.

In some embodiments, an apparatus includes a housing, a medicament container, a carrier and an energy storage member. The medicament container is at least partially disposed within the housing, and contains a dose of a medicament. The carrier has a distal end portion coupled to a needle. The distal end portion includes a side wall defining a coupling volume within which a distal end portion of the medicament container is movably coupled. The medicament container is fluidically isolated from a proximal tip of the needle when distal end portion of the medicament container is in a first container position within the coupling volume. The medicament container is fluidically coupled to the proximal tip of the needle when the distal end portion of the medicament container is in a second container position within the coupling volume. The side wall defining a bleed passageway placing the coupling volume in fluid communication with a volume outside of the carrier. The energy storage member is within the housing, and is configured to produce a force to move the medicament container from the first container position to the second container position. A portion of the force is also exerted to move a plunger within the medicament container to expel the dose of the medicament when the medicament container is in the second container position.

In some embodiments, the medicament delivery device can include an electronic circuit system coupled to the housing. The electronic circuit system is configured to produce an output when the electronic circuit system is actuated. The output can be, for example, an audible or visual output related to the epinephrine composition (e.g., an indication of the expiration date, the symptoms requirement treatment with epinephrine or the like), the use of the medicament delivery device, and/or post-administration procedures (e.g., a prompt to call 911, instructions for the disposal of the device or the like).

In some embodiments, a kit includes a package containing an auto-injector and a simulated auto-injector (also referred to as a trainer). The auto-injector is configured to deliver an amount of epinephrine effective for administration to a patient experiencing anaphylaxis and having a weight of less than 15 kg. The simulated auto-injector (or trainer) can be devoid of a medicament and/or those components that cause the medicament to be delivered (e.g., a needle, a nozzle or the like). In this manner, the simulated auto-injector can be used to train a user in the use of the actual medicament delivery device without exposing the user to a needle and/or a medicament.

In some embodiments, an infant-dose medical injector need not include an energy storage member contained therein that produces a force to either insert the needle, deliver the medicament through the needle, or both. For example, in some embodiments, a device can be configured for manual insertion (i.e., insertion of the needle caused by an insertion force directly produced by the user) and automatic injection (i.e., injection caused by a force produced by an energy storage member). In other embodiments, a device can be configured for automatic insertion (i.e., insertion of the needle caused by an insertion force produced by an energy storage member) and manual injection (i.e., injection caused by a force directly produced by the user). In yet other embodiments, an infant-dose medical injector can be devoid of an energy storage member that produces either a needle insertion force or an injection force. In such embodiments, the medical injector can include a housing that advantageously blocks light from the medicament, thereby limiting the degradation of the medicament and improving the long-term stability. Moreover, the medical injector can include mechanisms (e.g., end stop surfaces, release mechanisms, or the like) that produce a delivered dose tolerance of ±15 percent of a nominal dose volume. Such tolerance can be of heightened importance for low dose and/or low volume therapeutic regimens, such as for example, for an infant-dose of epinephrine. By maintaining the tolerance, even at dosage volumes of as low as 0.1 mL, the medical injectors and devices described herein can provide an emergency treatment solution that is appropriate for a patient population weighing less than 15 kg (e.g., between 7.5 kg and 15 kg), that can be stored for long periods of time, and that can be administered via an untrained user without the need to measure, monitor, or otherwise limit the dose volume.

In some embodiments, a medical injector includes a housing, a safety member, an actuator, and a dose limiter. The housing has a contact surface that is configured to contact a target location of a patient. A medicament container that contains a dose of epinephrine effective for administration to the patient experiencing anaphylaxis and having a weight of between 7.5 kg and 15 kg, is at least partially disposed within the housing. The medicament container is coupled to a needle, and a distal tip of the needle extends from the contact surface by a distance of between about 6.35 millimeters and about 9 millimeters. The safety member is removably coupled to a distal end portion of the housing, and surrounds a portion of the needle when the safety member is coupled to the distal end portion of the housing. The safety member is configured to remove a needle sheath from about the distal tip of the needle when the safety member is removed from the distal end portion of the housing. The actuator is coupled to the housing, and is configured to move from a first actuation position to a second actuation position to move a plunger within the medicament container to deliver the dose of epinephrine from the medicament container. The dose limiter is configured to limit distal movement of the plunger such that a volume of the dose delivered is within ±15 percent of a nominal dose volume.

In some embodiments, the medicament container is a prefilled syringe assembly including a syringe body and an elastomeric member disposed within the syringe body. The needle can be staked to a distal end portion of the syringe body. By including the dose of epinephrine within a prefilled syringe assembly, the medical injector can employ the cost-effective fill-finish solution provided by prefilled syringes, while also providing the structure for limiting light impingement on the epinephrine, providing a robust needle guard, and ensuring that the delivered dose is within the desired tolerance of the nominal dose for the target patient population.

In some embodiments, any of the medical injectors or devices described herein can include a case that is configured to be removably coupled about the housing. The case covers a status window defined by the housing when the medical injector is within the case. The dose of epinephrine is viewable through the status window after the housing is removed from the case.

In some embodiments, a method of delivering epinephrine includes removing a safety member from a distal end portion of a housing of a medical injector. The medical injector includes a medicament container containing a dose of epinephrine effective for administration to a patient experiencing anaphylaxis and having a weight of between 7.5 kg and 15 kg. The medicament container is coupled to a needle, and removal of the safety member causes a needle sheath to be removed from about a distal tip of the needle. The housing is moved distally to insert the distal tip of needle into a target location of the patient by a distance of between 7 millimeters and 8 millimeters. In some embodiments, the housing can be moved until a contact surface of the housing contacts a surface of the target location (e.g., the patient's skin, clothing, or the like). The medical injector is actuated, after being moved, to cause a force to move an end portion of a plunger distally within the medicament container to deliver the dose of epinephrine from the medicament container. The medical injector includes a stop surface to limit distal movement of the plunger such that a volume of the dose delivered is within ±15 percent of a nominal dose volume.

As used in this specification and the appended claims, the words "proximal" and "distal" refer to direction closer to and away from, respectively, an operator of the medical device. Thus, for example, the end of the medicament delivery device contacting the patient's body would be the distal end of the medicament delivery device, while the end opposite the distal end would be the proximal end of the medicament delivery device.

The term "about" when used in connection with a referenced numeric indication means the referenced numeric indication plus or minus up to 10 percent of that referenced numeric indication. For example, "about 100" means from 90 to 110.

The term "substantially" when used in connection with, for example, a geometric relationship, a numerical value, and/or a range is intended to convey that the geometric relationship (or the structures described thereby), the number, and/or the range so defined is nominally the recited geometric relationship, number, and/or range. For example, two structures described herein as being "substantially parallel" is intended to convey that, although a parallel geometric relationship is desirable, some non-parallelism can occur in a "substantially parallel" arrangement. By way of another example, a structure defining a volume that is "substantially 0.50 milliliters (mL)" is intended to convey that, while the recited volume is desirable, some tolerances can occur when the volume is "substantially" the recited volume (e.g., 0.50 mL). Such tolerances can result from manufacturing tolerances, measurement tolerances, and/or other practical considerations (such as, for example, minute imperfections, age of a structure so defined, a pressure or a force exerted within a system, and/or the like). As described above, a suitable tolerance can be, for example, of ±10% of the stated geometric construction, numerical value, and/or range. Furthermore, although a numerical value modified by the term "substantially" can allow for and/or otherwise encompass a tolerance of the stated numerical value, it is not intended to exclude the exact numerical value stated.

As used herein, the term "set" can refer to multiple features or a singular feature with multiple parts. For example, when referring to set of walls, the set of walls can be considered as one wall with multiple portions, or the set of walls can be considered as multiple, distinct walls. Thus, a monolithically-constructed item can include a set of walls. Such a set of walls can include, for example, multiple portions that are either continuous or discontinuous from each other. A set of walls can also be fabricated from multiple items that are produced separately and are later joined together (e.g., via a weld, an adhesive, or any suitable method).

The term "fluid-tight" is understood to encompass hermetic sealing (i.e., a seal that is gas-impervious) as well as a seal that is only liquid-impervious. The term "substantially" when used in connection with "fluid-tight," "gas-impervious," and/or "liquid-impervious" is intended to convey that, while total fluid imperviousness is desirable, some minimal leakage due to manufacturing tolerances, or other practical considerations (such as, for example, the pressure applied to the seal and/or within the fluid), can occur even in a "substantially fluid-tight" seal. Thus, a "substantially fluid-tight" seal includes a seal that prevents the passage of a fluid (including gases, liquids and/or slurries) therethrough when the seal is maintained at pressures of less than about 5 psig. Any residual fluid layer that may be present on a portion of a wall of a container after component defining a "substantially-fluid tight" seal are moved past the portion of the wall are not considered as leakage.

The epinephrine compositions described herein can be included in any suitable medicament delivery device. For example, in some embodiments, a drug product configured for administration by an untrained user (such a person accompanying the patient) can include any of the epinephrine compositions described herein. Such drug products can include, for example, an auto-injector having a needle length sufficient to produce an intramuscular injection while having a very low likelihood of striking the bone.

One example of such a medicament delivery device is provided in FIG. 1, which is a schematic illustration of a medicament delivery device (or drug product) 1000 according to an embodiment. The medicament delivery device 1000 includes a housing 1110, a contact surface 1330, a medicament container 1400, an energy storage member 1570, and an actuator 1302. The contact surface 1330 can be a portion of the housing 1110 or a structure separately coupled to the housing 1110, and is a surface that contacts a target location T of a patient during the delivery of any of the epinephrine compositions (or other drugs) disclosed herein. In some embodiments, the contact surface 1330 can have any suitable size and/or shape to maintain contact with the target location T during a delivery event. Specifically, the contact surface 1330 can have any shape as described herein, including a circular shape, a substantially rectangular shape, an oval shape, or the like. In some embodiments, the contact surface 1330 can be movably coupled to the housing 1110 (e.g., the contact surface 1330 can be spring-loaded to move when a threshold force has been applied the target location T). In other embodiments, the contact surface 1330 can be fixedly coupled to the housing 1110.

The medicament container 1400 is at least partially disposed within the housing 1110, and contains (i.e., is filled or partially filled with) an epinephrine composition 1420. The medicament container 1400 can be any container suitable for storing the epinephrine composition 1420. In some embodiments, the medicament container 1400 can be, for example, a prefilled syringe, a prefilled cartridge, a vial, an ampule or the like. In other embodiments, the medicament container 1400 can be a container having a flexible wall, such as, for example, a bladder. As shown, the proximal end portion of the medicament container 1400 contains an elastomeric member 1410 to seal the proximal end portion of the medicament container 1400. The elastomeric member 1410 can be disposed within the medicament container 1400 during the fill process, and can form a substantially fluid-tight seal to prevent leakage of the epinephrine composition 1420 from the medicament container 1400. Moreover, the elastomeric member 1410 is operatively coupled to the energy storage member 1570 such that, in use a force produced by the energy storage member 1570 acts upon the elastomeric member 1410 to deliver the epinephrine composition 1420 from the medicament container 1400.

The elastomeric member 1410 is formulated to be compatible with the epinephrine composition 1420. Similarly stated, the elastomeric member 1410 is formulated to minimize any reduction in the efficacy of the epinephrine composition 1420 that may result from contact (either direct or indirect) between the elastomeric member 1410 and the epinephrine composition 1420. For example, in some embodiments, the elastomeric member 1410 can be formulated to minimize any leaching or out-gassing of compositions that may have an undesired effect on the epinephrine composition 1420. In other embodiments, the elastomeric member 1410 can be formulated to maintain its chemical stability, flexibility and/or sealing properties when in contact (either direct or indirect) with epinephrine over a long period of time (e.g., for up to six months, one year, two years, five years or longer). In some embodiments, the elastomeric member 1410 can include or be composed of bromo-butyl rubber.

The epinephrine composition 1420 can be any of the epinephrine compositions described herein. In particular, medicament container 1400 can contain a dose of epinephrine 1420 effective for administration to a patient experiencing anaphylaxis and having a weight of less than about 15 kg (33 pounds), i.e., an infant-dose auto-injector. Such an infant-dose drug product is configured to deliver 0.1 mL of solution that contains 0.1 mg of epinephrine, 0.78 mg of sodium chloride, 0.15 mg of sodium bisulfite, and hydrochloric acid to adjust the pH. In other embodiments, however, medicament container 1400 can contain a dose of epinephrine 1420 effective for administration to a patient experiencing anaphylaxis and having any weight (i.e., an adult-dose device or a pediatric-dose device, as described herein). In yet other embodiments, the medicament container 1400 can include any suitable drug of the types described herein.

Figure 3:
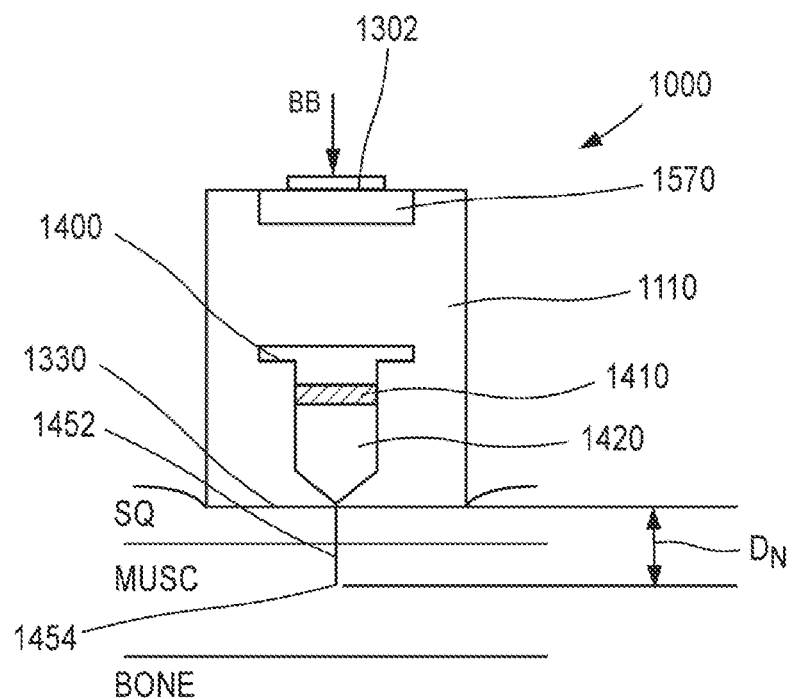

As shown, the distal end portion of the medicament container 1400 is coupled to a needle 1452. The needle 1452 includes a distal tip 1454 from which the epinephrine (or any suitable drug contained within the medicament container 1400) flows. Referring to FIG. 3, the needle 1452 is configured such that the distal tip 1454 extends from the contact surface 1330 by distance $D_N$ sufficient such that the distal tip 1454 is in the muscle layer (identified as MUSC) of the target location. Specifically, in some embodiments, the distance $D_N$ (or effective needle length) is such that the distal tip 1454 will be inserted within the thigh muscle for a patient weighing less than 15 kg (e.g., between 7.5 kg and 15 kg), and will have a low likelihood of striking the thigh bone (identified as BONE). In this manner, the distance $D_N$ is sufficient to produce an intramuscular delivery of the epinephrine 1420 while also limiting the likelihood of either an intraosseous delivery or a subcutaneous delivery. For example, in some embodiments, the distance $D_N$ is between about 6.35 mm and about 9 mm. In other embodiments, the distance $D_N$ is between about 7 mm and about 8 mm. In yet other embodiments, the distance $D_N$ is about 7.5 mm.

The needle 1452 defines a lumen that is in fluid communication with the medicament container 1400 to define a medicament delivery path through which the epinephrine composition 1420 can flow. The needle 1452 can be any gauge (e.g., 18 gauge, 23 gauge, 24 gauge, 25 gauge, 27 gauge, 32 gauge, etc.) to deliver the epinephrine composition 1420 through the lumen and into the target location T of body. The distal end tip 1454 can have any suitable bevel or shape.

The energy storage member 1570 is disposed within the housing 1110, and is configured to produce a force to deliver the epinephrine composition 1420 (e.g., from the medicament container 1400 to the target location T). The energy storage member 1570 can be any suitable device or mechanism that, when actuated, produces such force. In some embodiments, the energy storage member 1570 can be a mechanical energy storage member, such as a spring, a device containing compressed gas, a device containing a vapor pressure-based propellant or the like. In other embodiments, the energy storage member 1570 can be an electrical energy storage member, such as a battery, a capacitor, a magnetic energy storage member or the like. In yet other embodiments, the energy storage member 1570 can be a chemical energy storage member, such as a container containing two substances that, when mixed, react to produce energy.

As shown in FIG. 1, the energy storage member 1570 can be in any position and/or orientation relative to the medicament container 1400. In some embodiments, for example, the energy storage member 1570 can be positioned within the housing 1110 spaced apart from the medicament container 1400. Moreover, in some embodiments, the energy storage member 1570 can be positioned such that a longitudinal axis of the energy storage member 1570 is offset from the medicament container 1400. In other embodiments, the energy storage member 1570 can substantially surround the medicament container 1400.

As described herein, the actuator 1302 is any suitable device or mechanism that actuates the energy storage member 1570 to release the force. Although the actuator 1302 is shown as being disposed at the proximal end portion of the housing 1110, in other embodiments, the actuator 1302 can be located at the distal end portion of the housing 1110. In some embodiments, for example, the contact surface 1330 and the actuator 1302 can be monolithically constructed. Said another way, in some embodiments, the actuator 1302 can be a distal-end actuator and can include the contact surface 1330.

The use of the medicament delivery device 1000 is shown in FIGS. 1-4, which show the medicament delivery device 1000 in various configurations. To deliver the dose of epinephrine 1420, the medicament delivery device 1000 is first enabled (e.g., by removing a safety lock or the like, not shown). The contact surface 1330 is then placed into contact with the target location T, as shown in FIG. 1. The target location T can be any suitable location of the patient to which the epinephrine 1420 will be delivered. For example, the target location can be the thigh of the patient. As shown, the target location can include a subcutaneous layer SQ, a layer of muscle MUSC, and a bone (identified as BONE) beneath the muscle MUSC. Although not shown, the target location T is covered by a layer of skin. In some embodiments, the needle-based delivery of the medicament delivery device 1000 can accommodate delivery through a layer of clothing between the contact surface 1330 and the skin. Specifically, the medicament delivery device 1000 can be configured to insert the needle 1452 with sufficient force, and the needle 1452 can extend a sufficient distance $D_N$ such that the epinephrine 1420 can be delivered through one or more layers of clothing. Such layers can include typical infant clothing, such as pajamas with leggings, denim material, or the like. In some embodiments, the medicament delivery device 1000 (or any of the other devices or drug products described herein) can be configured to deliver the epinephrine 1420 via the needle 1452 through up to four layers of "duck cloth." Duck cloth is a common term that refers to a heavy, plain woven cotton fabric. Duck cloth can also be referred to as canvas. In some embodiments, the medicament delivery device 1000 (or any of the other devices or drug products described herein) can be configured to deliver the epinephrine 1420 via the needle 1452 through up to four layers of "duck cloth." In some embodiments, the medicament delivery device 1000 (or any of the other devices or drug products described herein) can be configured to deliver the epinephrine 1420 via the needle 1452 through up to four layers of 12-ounce denim cloth.

Figure 2:
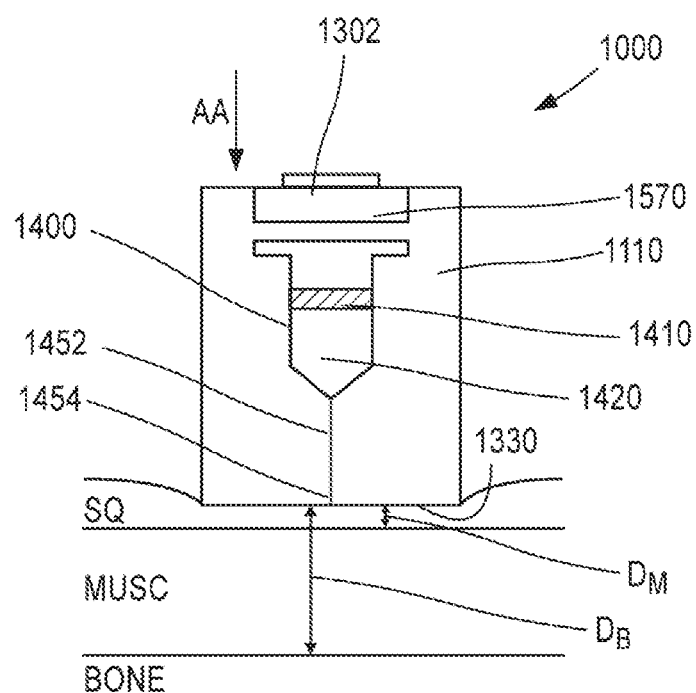

To actuate the device, the housing 1110 and the contact surface 1330 are maintained firmly against the target location T by applying a distal force as shown by the arrow AA in FIG. 2. The actuator 1302 is manipulated to actuate the energy storage member 1570. In particular, the actuator 1302 is moved in the distal direction (indicated by the arrow AA) such that the application of the force to maintain the contact surface 1330 in contact with the target location T is also the force applied to manipulate the actuator 1302. In this manner, the operation of maintaining the contact surface 1330 against the target location and actuating the device 1000 is a single operation. In other embodiments, however, the actuator 1302 can be manipulated in any suitable direction. For example, in other embodiments, the user can apply a distal (or downward) force to maintain the contact surface 1330 in contact with the target location T and a separate force (i.e., having a different direction) to manipulate the actuator 1302. In some embodiments, for example, the actuator 1302 can be moved relative to the housing by a force that is nonparallel to a longitudinal axis of the needle. In some embodiments, the actuator 1302 can be moved relative to the housing by rotating the actuator.

As shown in FIG. 2, the application of the distal force by the contact surface 1330 against the target location T acts to compress the tissue layers of the target location T. Specifically, any of the skin, the subcutaneous layer SQ, or the layer of muscle MUSC can be compressed. As a result, the distance from the outer surface of the target location to the muscle layer (identified as $D_M$ in FIG. 2) is less than that which results when little or no force is applied by the contact surface 1330. Similarly, the distance from the outer surface of the target location to the bone (identified as $D_B$ in FIG. 2) is less than that which results when little or no force is applied by the contact surface 1330. Accordingly, the distance $D_N$ that the needle extends from the contact surface 1330 is selected based on the expected compression of the tissue layers of the specific target location T. As described herein, the selection of the distance $D_N$ is informed by many factors, including, but not limited to, the physical characteristics of the target location T (e.g., anatomical differences between various locations, such as the thigh, buttocks, shoulder, or the like), the nominal size of the patient (i.e., adult vs. pediatric vs. infant), the force applied by the contact surface 1330 against the target location T, the shape and size of the contact surface 1330, the thickness of any layers of clothing that are present, and the expected amount of "kickback" or reduction in force during a delivery event, to name a few.

In some embodiments, the target location T is the patient's thigh. A recent study has shown that compression of the thigh tissue during actuation of a variety of different auto-injectors in patients having a weight of between about 15 kg and about 30 kg results in a decrease in the distance $D_M$ of about 1 mm (from a nominal distance of about 6.7 mm to a nominal distance of about 5.8 mm). Similarly, this study showed decrease in the distance $D_B$ of about 13 mm (from a nominal distance of about 29.5 mm to a nominal distance of about 16.7 mm). Although this study provides general information about the compression of the tissue layers in the thigh for patients having a weight of between about 15 kg and about 30 kg, the distance $D_N$ (or effective needle length) of the medicament delivery device 1000 is specifically tailored for this drug product based on, among other things, the factors described herein.

Figure 4:
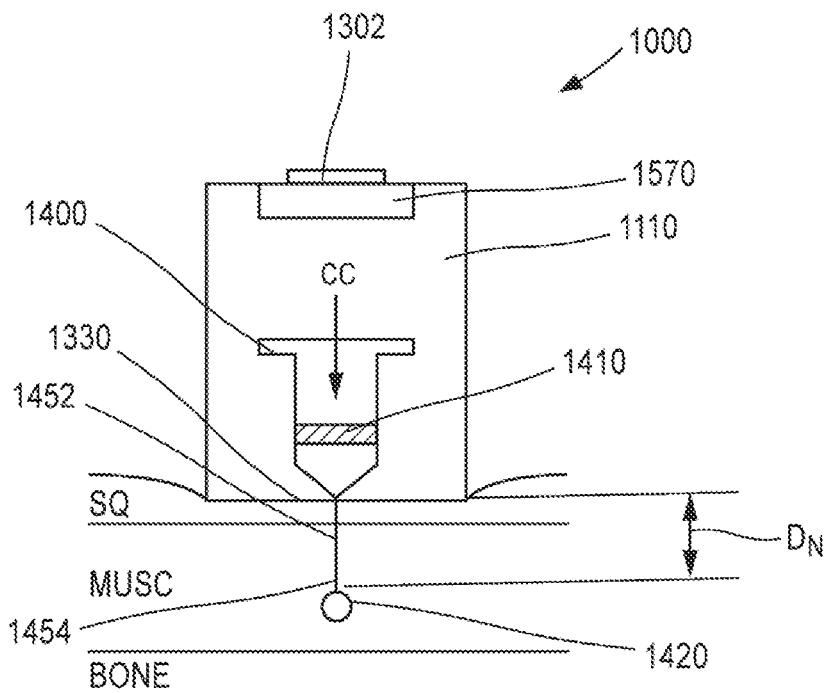

As shown in FIG. 3, after actuation of the device 1000, the energy storage member exerts a force to move the needle 1452 from a first needle position (within the housing, see FIGS. 1 and 2) to a second needle position (insertion position, see FIGS. 3 and 4). When the needle is in the second (or inserted) needle position, the distance $D_N$ (or effective needle length) is such that the distal tip 1454 will be inserted within the thigh muscle for a patient weighing less than 15 kg, and will have a low likelihood of striking the thigh bone (identified as BONE). In this manner, the distance $D_N$ is sufficient to produce an intramuscular delivery of the epinephrine 1420 while also limiting the likelihood of either an intraosseous delivery or a subcutaneous delivery. For example, in some embodiments, the distance $D_N$ is between about 6.35 mm and about 9 mm. In other embodiments, the distance $D_N$ is between about 7 mm and about 8 mm. In yet other embodiments, the distance $D_N$ is about 7.5 mm.

After insertion of the needle 1452, the dose of the epinephrine 1420 is delivered intramuscularly to the patient, as shown in FIG. 4. In particular, in some embodiments, the medicament delivery device 1000 can deliver a dose of epinephrine 1420 effective for administration to a patient experiencing anaphylaxis and having a weight of less than about 15 kg (33 pounds), i.e., an infant-dose auto-injector. Such an infant-dose drug product is configured to deliver 0.1 mL of solution that contains 0.1 mg of epinephrine, 0.78 mg of sodium chloride, 0.15 mg of sodium bisulfite, and hydrochloric acid to adjust the pH. In other embodiments, the medicament delivery device 1000 can deliver a dose of epinephrine 1420 effective for administration to a patient experiencing anaphylaxis and having a weight of between about 7.5 kg and about 15 kg (33 pounds). In such embodiments, the drug product is configured to a solution that contains between about 0.06 mg and about 0.15 mg of epinephrine. In yet other embodiments, the medicament container 1400 can include any suitable drug of the types described herein.

Although the medicament delivery device 1000 is shown as including the actuator 1302 at the proximal end of the housing 1110 (the end opposite the contact surface 1330), in other embodiments, a medicament delivery device and/or drug product can include the contact surface 1330 as a part of a distally-located actuator. In this manner, as described above, the operation of maintaining the contact surface against the target location and actuating the device can be performed in a single operation. For example, FIG. 5 is a schematic illustration of a medicament delivery device (or drug product) 2000. The medicament delivery device 2000 includes a housing 2110 and an actuator 2302. Although not shown, the medicament delivery device 2000 includes a medicament container (coupleable to a needle) and an energy storage member, similar the medicament container 1400 and the energy storage member 1570 described above, or any other medicament containers or energy storage member described herein. Thus, the details of the medicament container, the dose of medicament (e.g., epinephrine), and the like are not described in detail herein.

As shown, the housing 2110 includes a proximal end portion 2112 and a distal end portion 2114. The actuator 2302 is movably coupled to the distal end portion 2114 of the housing 2110. The actuator 2302 includes a contact surface 2330 that, in use, contacts a target location of a patient during the delivery of any of the epinephrine compositions (or other drugs) disclosed herein. The contact surface 2330 can have any suitable size and/or shape to maintain contact with the target location during a delivery event. Specifically, the contact surface 2330 can have any shape as described herein, including a circular shape, a substantially rectangular shape, an oval shape, or the like.

The actuator 2302 is any suitable device or mechanism that actuates the energy storage member to release a force to insert the needle (not shown) and deliver the dose of medicament. For example, in some embodiments, the actuator 2302 (or any of the actuators described herein) can include an engagement portion configured to engage a release rod that releases a spring or any other stored energy member, similar to that shown below for the actuator 4302. Moreover, the contact surface 2330 is a portion of (i.e., the distal-most surface of) the actuator 2302. In this manner, the force applied to maintain contact between the contact surface 2330 and the target location is also exerted to move the actuator 2302 relative to the housing, as shown by the arrow DD in FIG. 5.

Similar the medicament delivery device (or drug product) 1000 described above, the device 2000 is configured such that a distal tip of the needle therein extends from the contact surface 2330 by distance sufficient such that the distal tip is in the muscle layer of the target location. Although not shown in FIG. 5, the distance (or effective needle length) is similar in nature to the needle distance $D_N$ shown above for the device 1000 (see, e.g., FIG. 3). Specifically, in some embodiments, the effective needle length is such that the distal tip will be inserted within the thigh muscle for a patient weighing less than 15 kg, and will have a low likelihood of striking the thigh bone. In this manner, the distance (or effective needle length) is sufficient to produce an intramuscular delivery of epinephrine contained within the drug product 2000 while also limiting the likelihood of either an intraosseous delivery or a subcutaneous delivery. For example, in some embodiments, the distance of needle extension (or effective needle length) is between about 6.35 mm and about 9 mm. In other embodiments, the distance of needle extension (or effective needle length) is between about 7 mm and about 8 mm. In yet other embodiments, the distance of needle extension (or effective needle length) is about 7.5 mm.

As described herein, the selection of the distance of needle extension (or effective needle length) is informed by many factors, including, but not limited to, the physical characteristics of the target location T (e.g., anatomical differences between various locations, such as the thigh, buttocks, shoulder, or the like), the nominal size of the patient (i.e., adult vs. pediatric vs. infant), the force applied by the contact surface 2330 against the target location T, the shape and size of the contact surface 2330, the thickness of any layers of clothing that are present, and the expected amount of "kickback" or reduction in force during a delivery event, to name a few. In some embodiments, the force applied by the contact surface 2330 (shown by the arrow DD in FIG. 5) can be within a range such that expected compression of the tissue layers can be understood when in conjunction with determining the effective needle length. For example, in some embodiments, the force applied by the contact surface 2330 to actuate the device 2000 (or the distal force applied by any of the devices shown herein) can be between about 8.9 N (2 lbf) and about 44.5 N (10 lbf). In other embodiments, the force applied by the contact surface 2330 to actuate the device 2000 (or the distal force applied by any of the devices shown herein) can be about 26.7 N (6 lbf).

Because the force applied against the contact surface 2330 (or by the contact surface onto the target location) is applied over the surface area of the contact surface, the pressure against the target location is determined as the force divided by the area of the contact surface. Moreover, the pressure applied against the target location can vary spatially depending on the contact between the contact surface 2330 and the target location. Thus, the size and/or shape of the contact surface 2330 (or any of the contact surfaces described herein) can impact the amount of compression of the target tissue. In some embodiments, the contact surface 2330 (or any of the contact surfaces described herein) can have a circular cross-sectional shape. In other embodiments, the contact surface 2330 (or any of the contact surfaces described herein) can have an oval or rectangular cross-sectional shape. In yet other embodiments, the contact surface 2330 (or any of the contact surfaces described herein) can have an irregular cross-sectional shape. For example, FIG. 6 shows a schematic illustration of an actuator 3302 having a contact surface 3330 having an irregular shape. This shape can produce the desired tissue compression effect that, in conjunction with the extended needle length, produces the desired delivery (e.g., intramuscular) in the targeted patient population (e.g., patients weighing less than 15 kg).

Although FIG. 6 shows the shape of the contact surface 3330 in a plane substantially normal to a longitudinal axis of the needle, in other embodiments, a contact surface can have any suitable shape in a plane substantially parallel to a longitudinal axis of the needle. For example, in some embodiments, the contact surface 2330 (or any of the contact surfaces described herein) can be substantially planar when viewed in a plane substantially parallel to a longitudinal axis of the needle. In other embodiments, however, the contact surface 2330 (or any of the contact surfaces described herein) can be non-planar when viewed in a plane substantially parallel to a longitudinal axis of the needle. For example, FIG. 7 shows a side view schematic illustration of an actuator 3302' having a contact surface 3330'. Similar to the other devices (drug products) described herein, the device depicted in FIG. 7 includes a needle 3452' having a distal tip 3454' that, in use, extends from the contact surface 3330' by a distance $D_N$ (extended needle length). The distance $D_N$ can be any suitable length as described herein. As shown in FIG. 7, when viewed in a plane substantially parallel to a longitudinal axis of the needle 3452', the contact surface 3330' is non-planar. Specifically, the contact surface 3330' is convex. In this manner, when the contact surface 3330' is depressed against the target tissue, the convex shape ensures that the area of the contact surface 3330' surrounding the needle 3452' will maintain firm contact with the target location. This arrangement prevents inadvertent spacing or separation between the target location and the contact surface 3330' during use. Such spacing could, for example, result in the distal end tip 3454' of the needle 3452' being insufficiently inserted to reach the muscular layer.

The surface area of the contact surface 3330', the contact surface 3300 or any of the contact surfaces described herein can be any suitable value to produce the desired injection characteristics. For example, any of the contact surfaces described herein can have an area that, taken in conjunction with the actuation force, produces a pressure against the target location that is within a desired range. For example, in some embodiments, any of the contact surfaces described herein (including the contact surfaces 1330, 2330, 3300, 4330) can have a contact area of about 322 mm$^2$ (about 0.5 square inches) to about 645 mm$^2$ (about 1 square inch). Such contact area can exclude any openings, cut-outs, or the like. In other embodiments, the contact area can be greater than about 645 mm$^2$ (about 1 square inch). For example, in some embodiments the contact area of any of the contact surfaces described herein (including the contact surfaces 1330, 2330, 3300, 4330) can be between about 645 mm$^2$ (about 1 square inch) and about 968 mm$^2$ (about 1.5 square inches) or between about 645 mm$^2$ (about 1 square inch) and about 1290 mm$^2$ (about 2 square inches).

Figure 8:
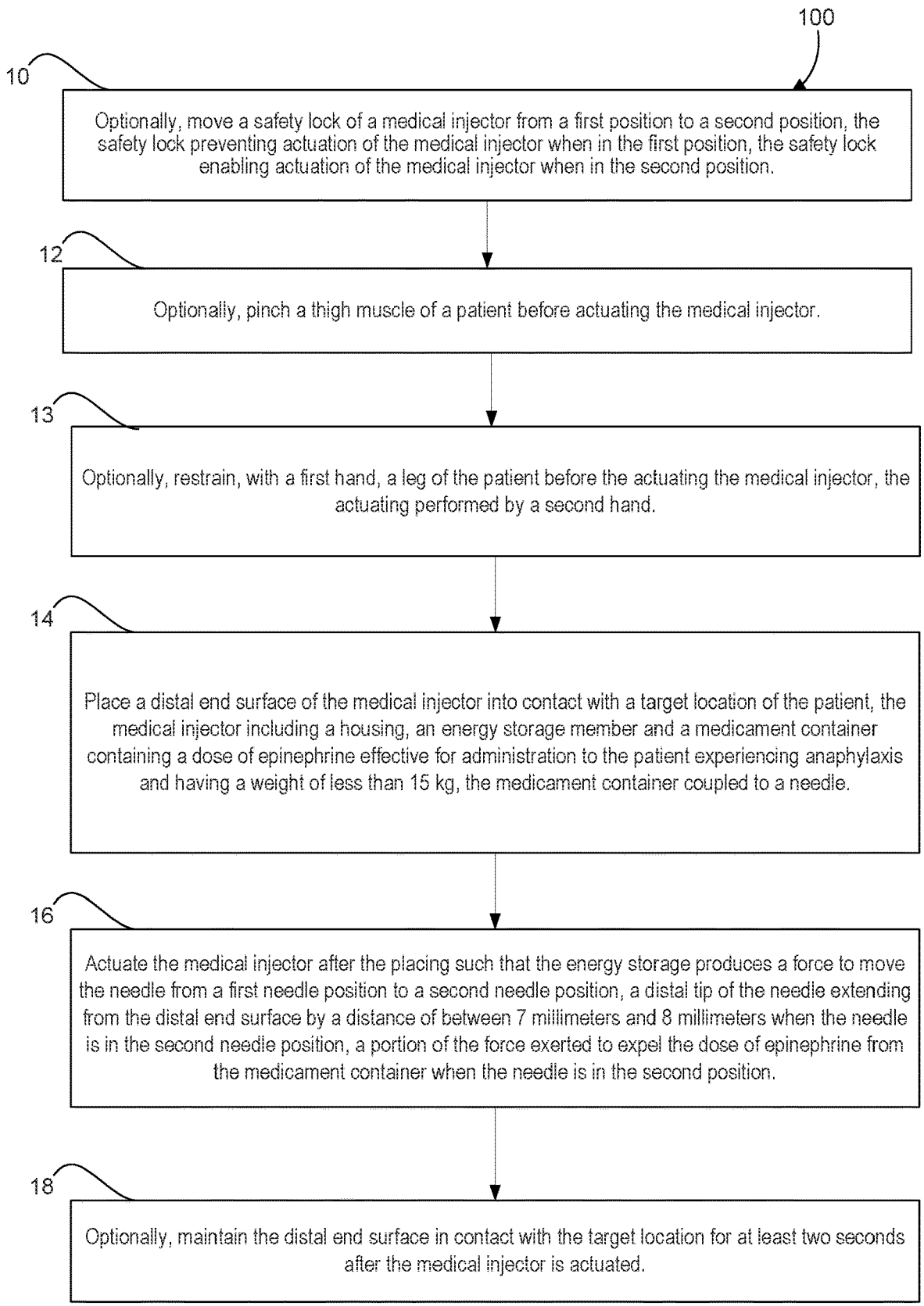
FIG. 8 is a flow chart of a method of delivering drugs, according to an embodiment.
Figure 10:
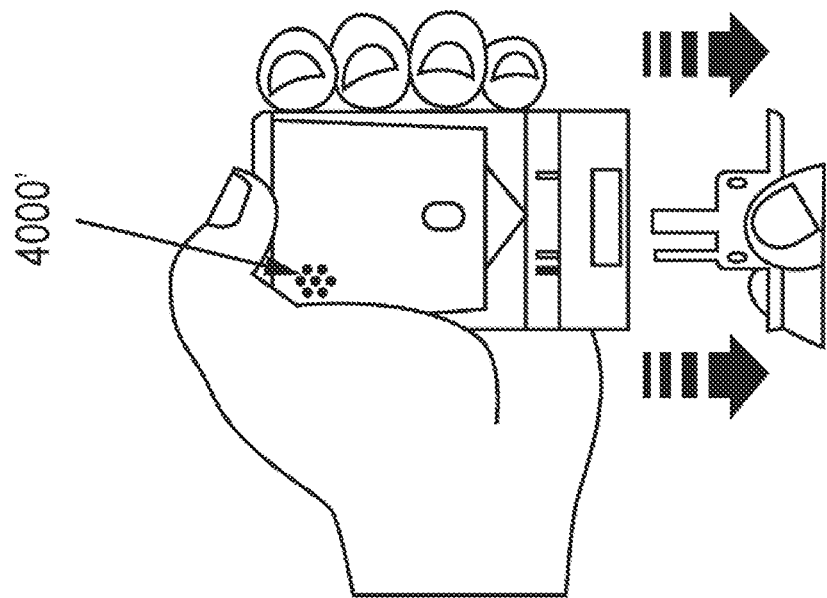
FIGS. 9-10, 11A, and 11B are images showing a method of use of a medicament delivery device, according to an embodiment.
Figure 9:
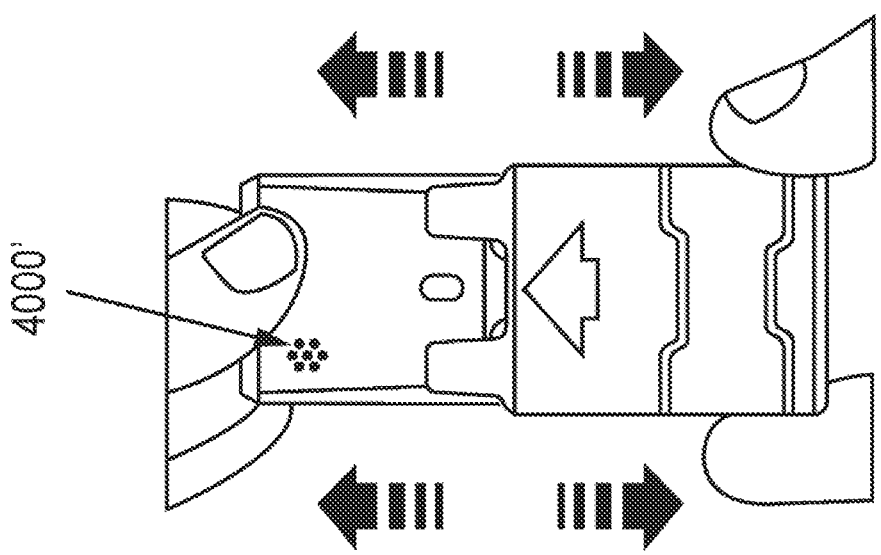

Any of the devices and/or drug products described herein can be used according to any suitable method delivery the desired drug formulation to a specific target location of a specific patient population. For example, FIG. 8 is a flow chart is showing a method 100 of using a delivery device to deliver a dose of epinephrine to a patient weighing less than 15 kg according to an embodiment. For example, the method 100 can be performed with any of the medicament delivery devices (or drug products) described herein, including the delivery devices 1000, 2000, 4000, and 4000'. For purposes of explanation, the method 100 is described with reference to FIGS. 9, 10, 11A, and 11B, which show a device 4000' and an infant patient, P. The device 4000' can be similar to the device 4000 described below, or any other devices described herein. In some embodiments, the method 100 optionally includes moving a safety lock 4700' of a medical injector from a first position to a second position, at 10. The safety lock 4700', which can be similar to the safety lock 4700 (or the cover 4200) described below, can prevent actuation of the medical injector when in the first position, and can enable actuation of the medical injector when in the second position. For example, FIG. 9 shows the removal of a cover 4200' (similar to the cover 4200) from about the device 4000'. FIG. 10 shows the removal of a distal-end safety lock, similar to the safety lock 4700, from the device 4000'. In this manner, moving (or removing) the safety lock places the medical injector in a "ready" state.

Figure 11B:
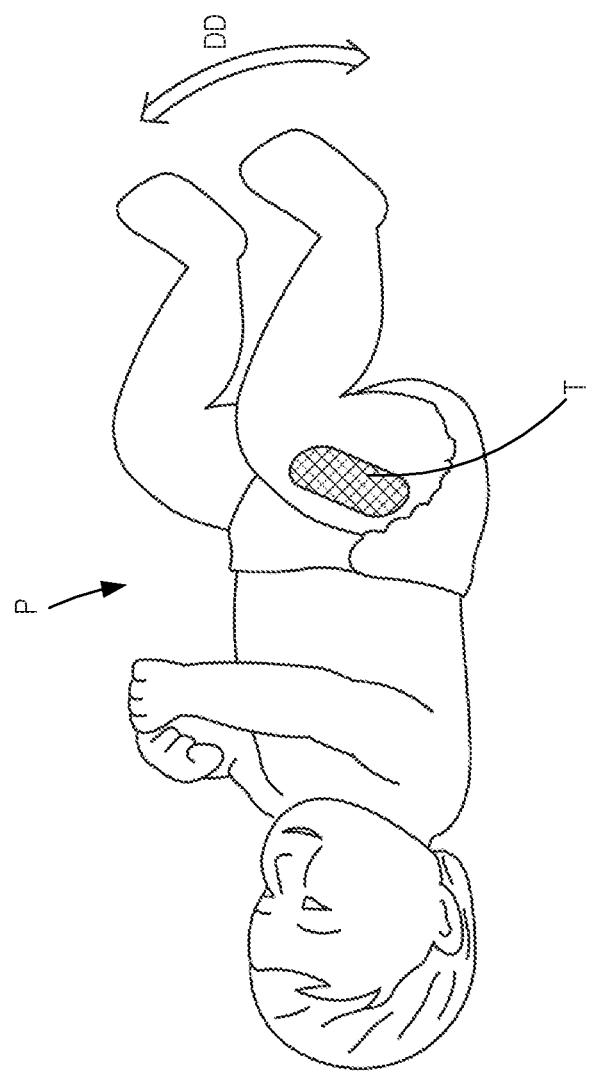

In some embodiments, the target location for injection is the thigh, and more specifically, the anterolateral aspect of the thigh, as indicated by the reference character T and the shaded region shown in FIG. 11B. In some embodiments, the method 100 optionally includes pinching a thigh muscle of the patient before actuating the medical injector, at 12. Pinching of the leg or thigh muscle can move the intended injection site (or target location) away from the underlying bone. This optional step can therefore increase the margin of safety to avoid needle contact or penetration of bone. FIG. 11 shows a caregiver pinching the thigh T of the patient P before (and during) actuation of the device 4000'.

A distal end surface of the medical injector is then placed into contact with a target location of a patient, at 14. As described above, the medical injector includes a housing, an energy storage member and a medicament container containing a dose of epinephrine effective for administration to the patient experiencing anaphylaxis and having a weight of less than 15 kg (and more specifically, between 7.5 kg and 15 kg). The medicament container is coupled to a needle. In some embodiments, the dose of epinephrine contains between about 0.06 mg epinephrine and about 0.150 mg epinephrine. In some embodiments, the dose of epinephrine contains about 0.1 mg epinephrine. In some embodiments, the dose of epinephrine includes about 0.1 mL of a solution containing about 0.1 mg epinephrine, about 0.78 mg sodium chloride, and about 0.15 mg sodium bisulfite hydrochloric acid.

Figure 11A:
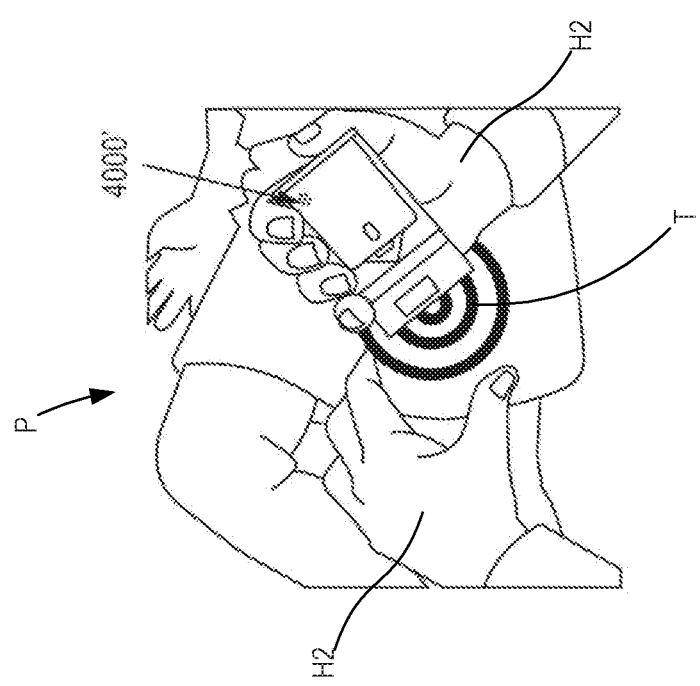

As shown in FIG. 11A, in some embodiments, a contact surface of the medical injector can be placed into direct contact with a clothing article covering the target location.

The medical injector is then actuated after it is placed in position on the target location, at 16. The actuation causes the energy storage member to produce a force to move the needle from a first needle position to a second needle position. As described above, a distal tip of the needle extends from the distal end surface by a distance of between 7 millimeters and 8 millimeters when the needle is in the second needle position. Moreover, after the needle is inserted, a portion of the force is exerted to expel the dose of epinephrine from the medicament container when the needle is in the second position. In some embodiments, the medical injector can be actuated by pressing the actuator against the target location. In some such embodiments, the actuator can be pressed against the target location with a force of between about 8.9 N (2 lbf) and about 44.5 N (10 lbf). In other embodiments, the actuator can be pressed against the target location with a force of about 26.7 N (6 lbf).

In some embodiments, the method 100 optionally includes maintaining the distal end surface in contact with the target location for at least two seconds after the medical injector is actuated, at 18.

Because the method 100 addresses delivery of epinephrine to patients weighing less than 15 kg, such patients are typically very young and are unable to administer the dose themselves. Moreover, in some instances, the patient may be uncooperative and kick or move, as shown by the arrow DD in FIG. 11B. Accordingly, in some embodiments, the method 100 optionally includes holding and/or limiting movement of the target location before and after the medical injector is actuated. Specifically, in some embodiments, the method 100 optionally includes restraining a leg of the patient with a first hand H1, and actuating the device by pressing the actuator against the target location with a second hand H2, at 13. In this manner, the likelihood that the patient will move suddenly to disrupt the delivery process is minimized Although the method 100 includes restraining the leg of the patient with the user's hand (H1), in other embodiments, a method can include restraining the leg of the patient by any suitable method. For example, in some embodiments, the user can support the patient on the user's lap and restrain the patient's leg between the user's legs. This can allow one hand of the user to restrain the patient's arms or torso, while using the other hand to manipulate the medical injector.

Figure 12:
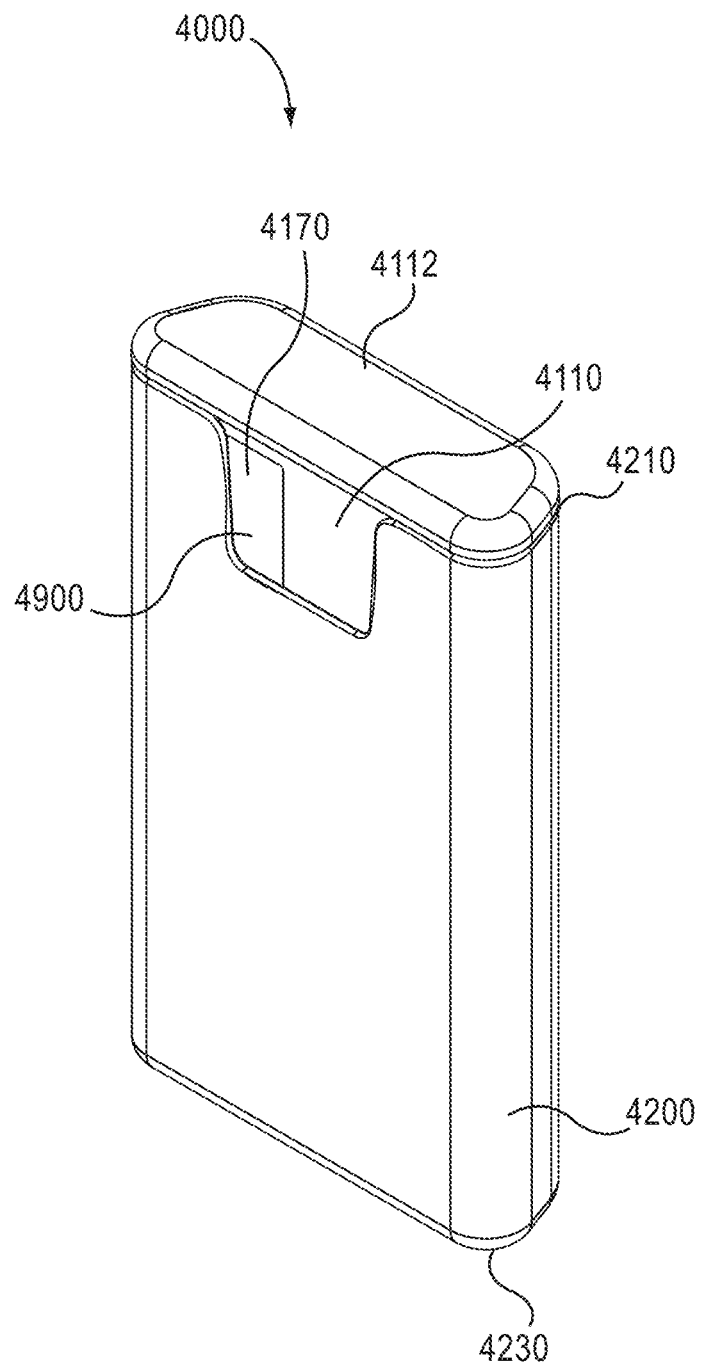
FIGS. 12 and 13 are perspective views of a medical injector according to an embodiment, in a first configuration.
Figure 13:
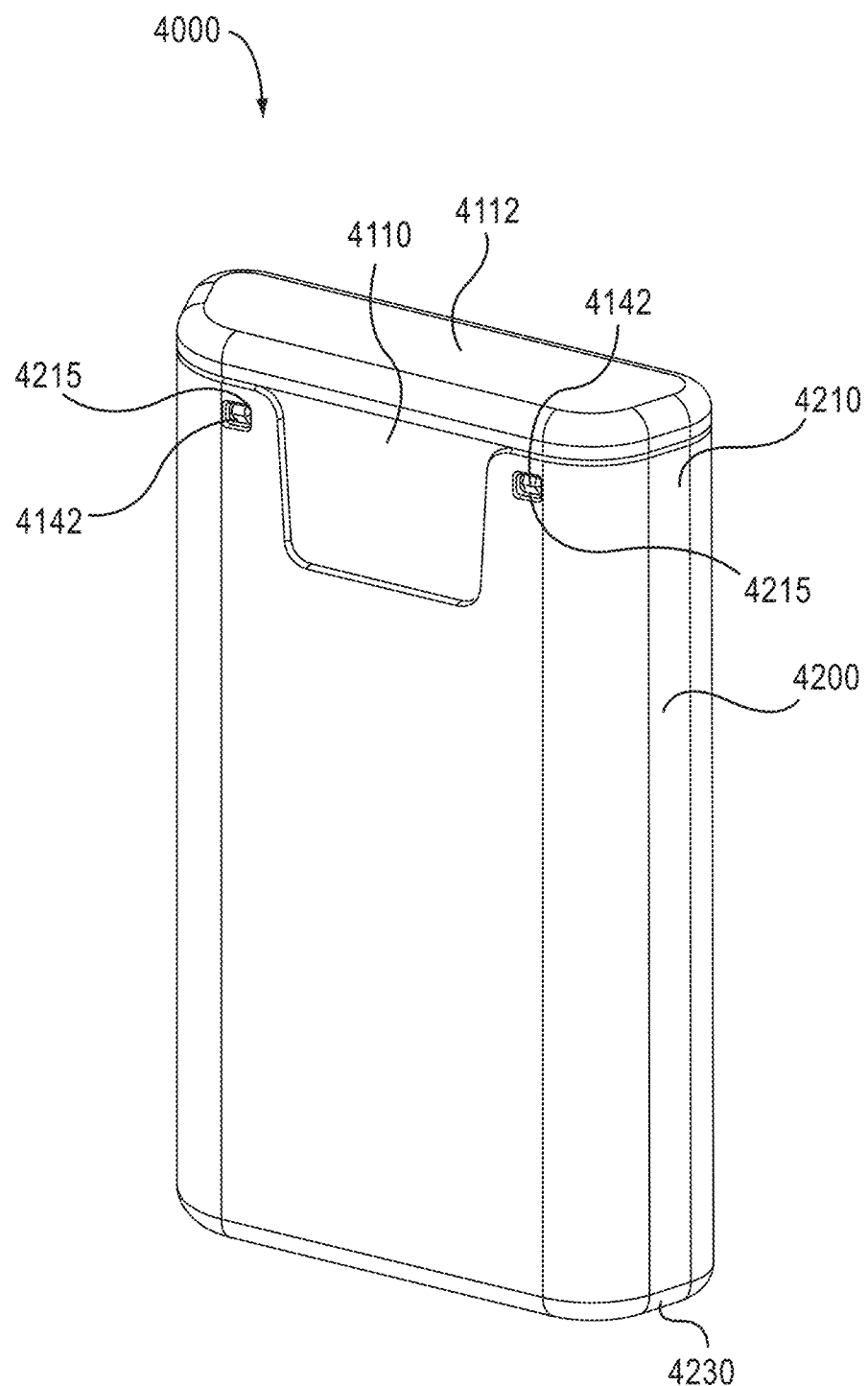
Figure 14:
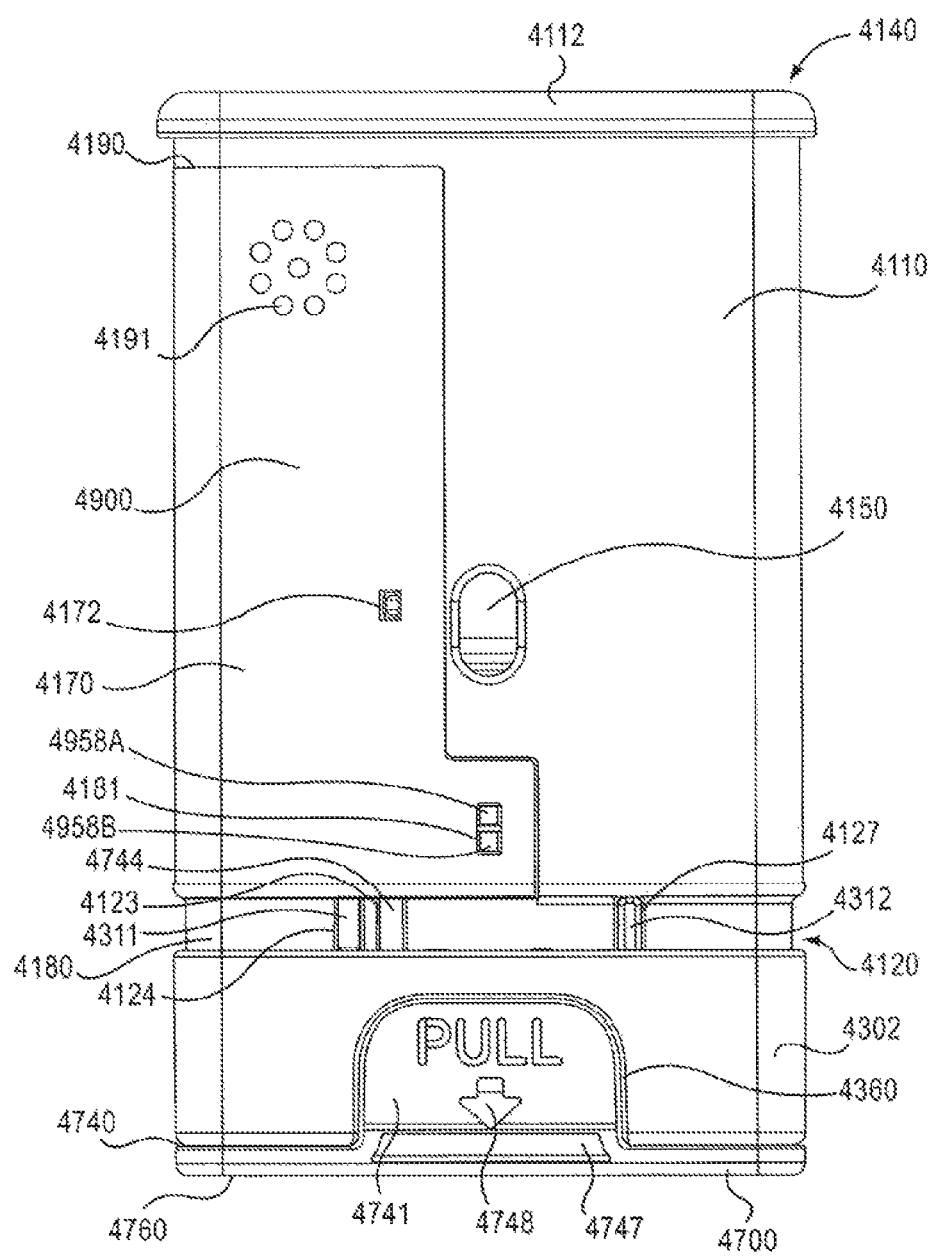
FIG. 14 is a front view of the medical injector illustrated in FIG. 12 with the cover removed.
Figure 37:
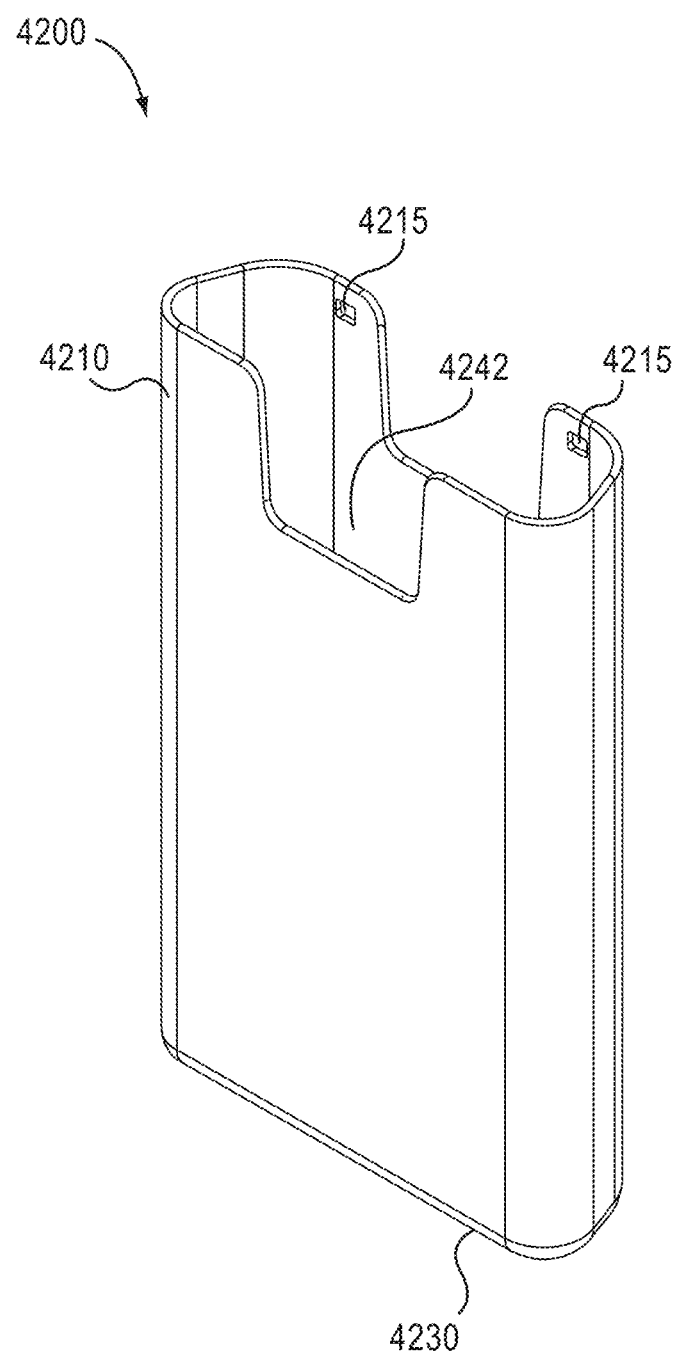
FIGS. 37 and 38 are perspective views of a cover of the medical injector illustrated in FIG. 12.
Figure 38:
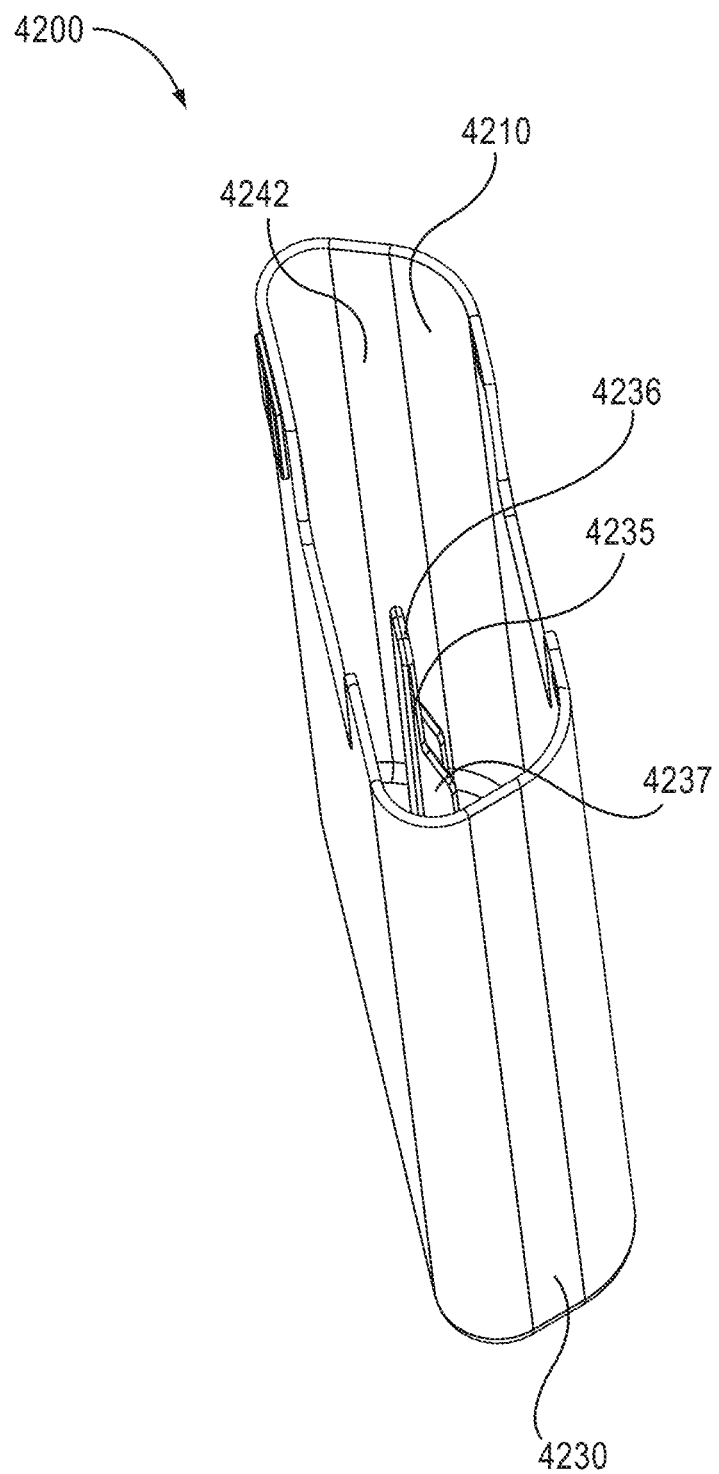
Figure 39:
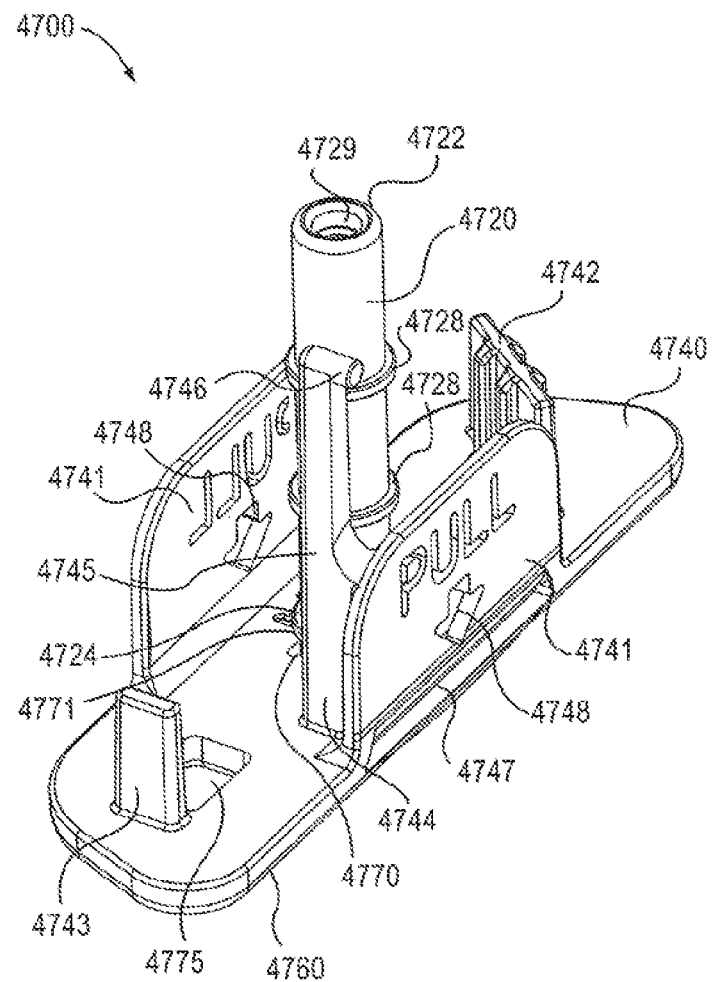
FIG. 39 is a perspective view of a safety lock of the medical injector illustrated in FIG. 12.
Figure 40:
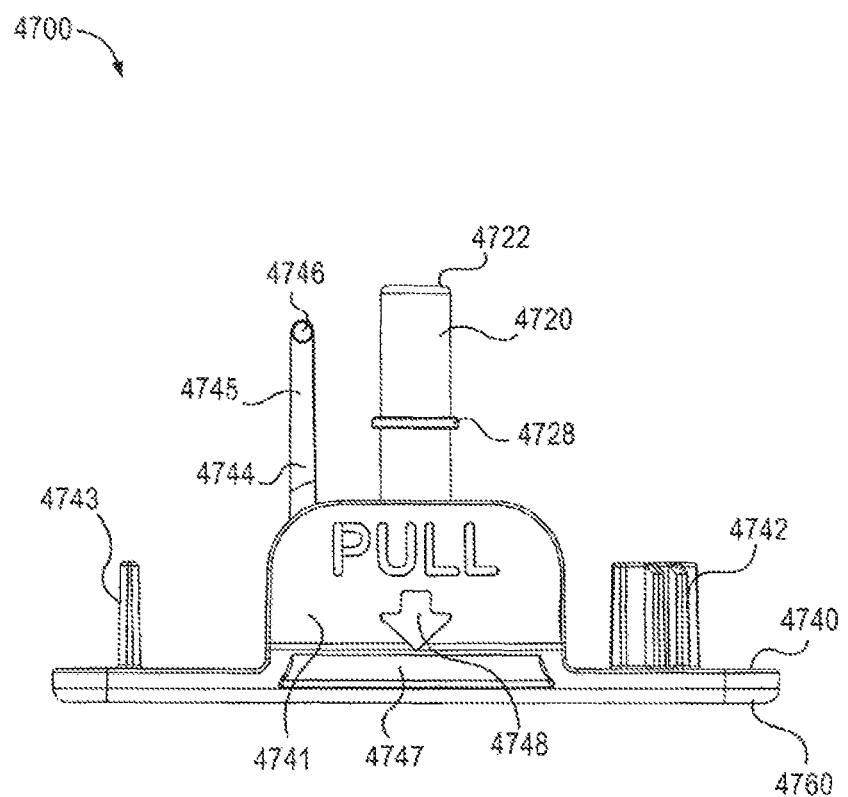
FIG. 40 is a front view of the safety lock of the medical injector illustrated in FIG. 39.

In some embodiments, any of the methods or medicament delivery devices described herein can be an auto-injector configured to automatically deliver an epinephrine composition. For example, FIGS. 12-50 show a medical injector 4000, according to an embodiment. FIGS. 12-13 are perspective views of the medical injector 4000 in a first configuration (i.e., prior to use). The medical injector 4000 includes a housing 4110, a delivery mechanism 4500 (see e.g., FIGS. 21-22), a medicament container 4400 containing a dose of epinephrine 4420 (see e.g., FIG. 24), an electronic circuit system 4900 (see e.g., FIGS. 26-36), a cover 4200 (see e.g., FIGS. 37-38), a safety lock 4700 (see e.g., FIGS. 39-42) and a system actuator assembly 4300 (see e.g., FIGS. 21, 23, 43 and 44). A discussion of the components of the medical injector 4000 will be followed by a discussion of the operation of the medical injector 4000.

As shown in FIGS. 14-20, the housing 4110 has a proximal end portion 4140 and a distal end portion 4120. The housing 4110 defines a first status indicator aperture 4150 and a second status indicator aperture 4151. The first status indicator aperture 4150 defined by the housing 4110 is located on a first side of the housing 4110, and the second status indicator aperture 4151 of the housing 4110 is located on a second side of the housing 4110. The status indicator apertures 4150, 4151 can allow a patient (or caregiver) to monitor the status and/or contents of the medicament container 4400 contained within the housing 4110. For example, by visually inspecting the status indicator apertures 4150, 4151, a patient (or caregiver) can determine whether the medicament container 4400 contains a medicament and/or whether a medicament has been dispensed. The patient (or caregiver) can also see various status indicators through the status indicator apertures 4150, 4151, such as, for example, portions of the carrier 4520, the medicament container 4400, including the crimp seal, or the like.

Figure 18:
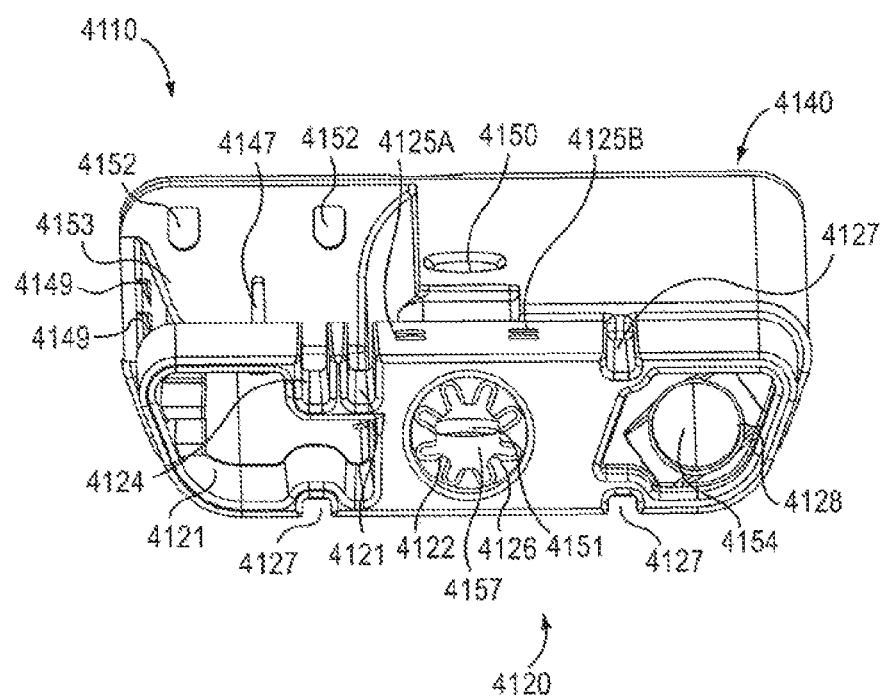
FIG. 18 is a bottom perspective view of a housing of the medical injector illustrated in FIG. 12.
Figure 19:
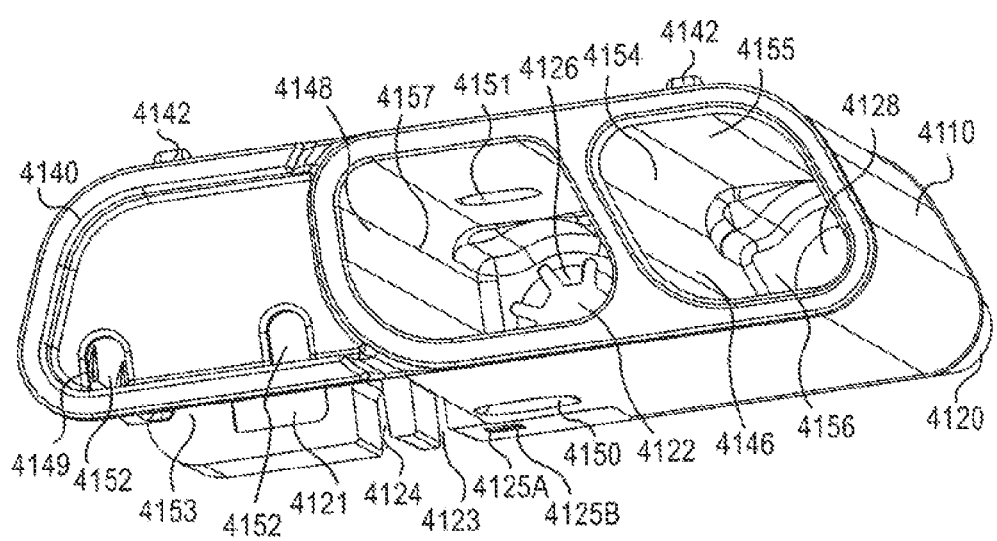
FIG. 19 is a top perspective view of a housing of the medical injector illustrated in FIG. 12.
Figure 21:
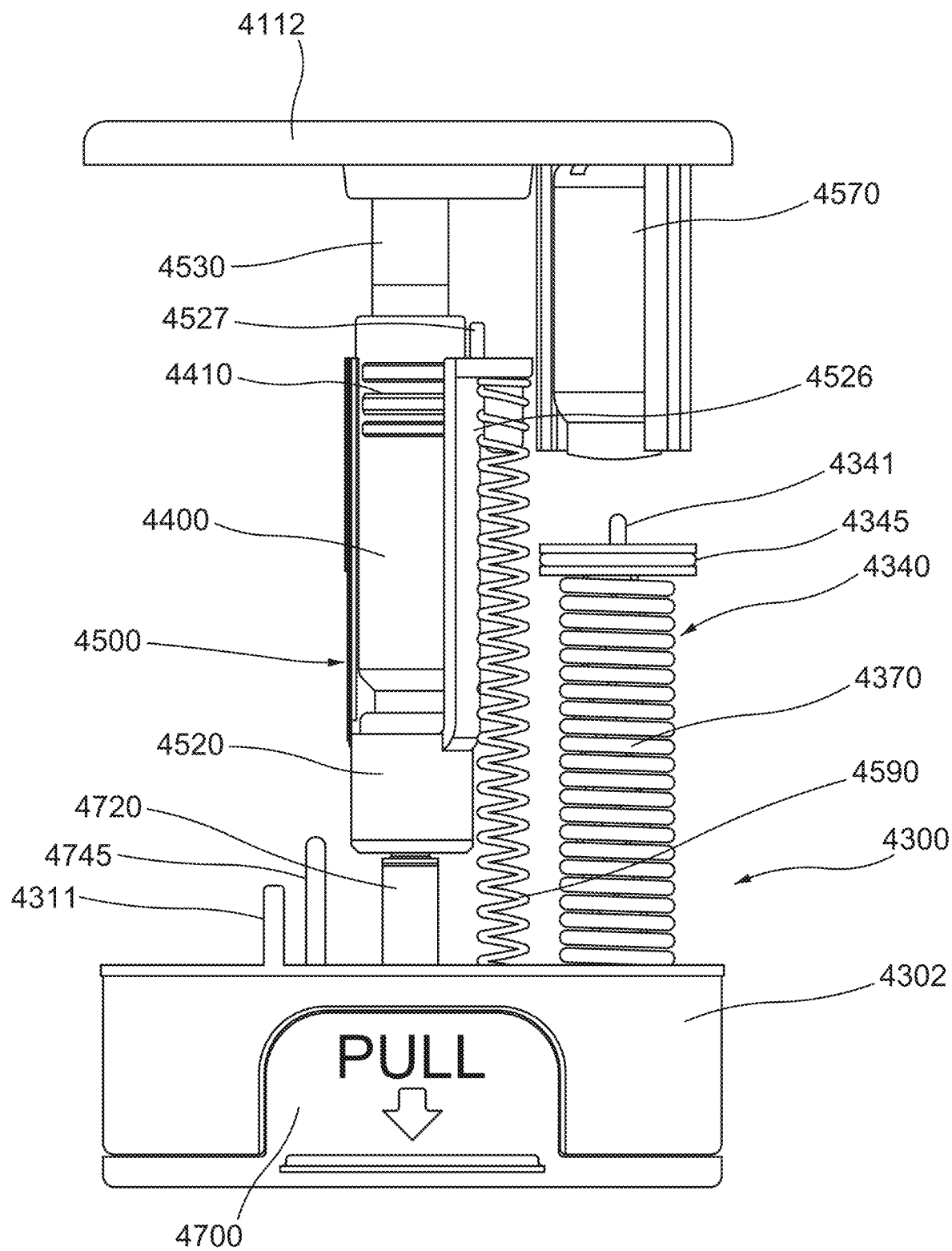
FIGS. 21 and 22 are front views of a medicament delivery mechanism of the medical injector illustrated in FIG. 12.
Figure 22:
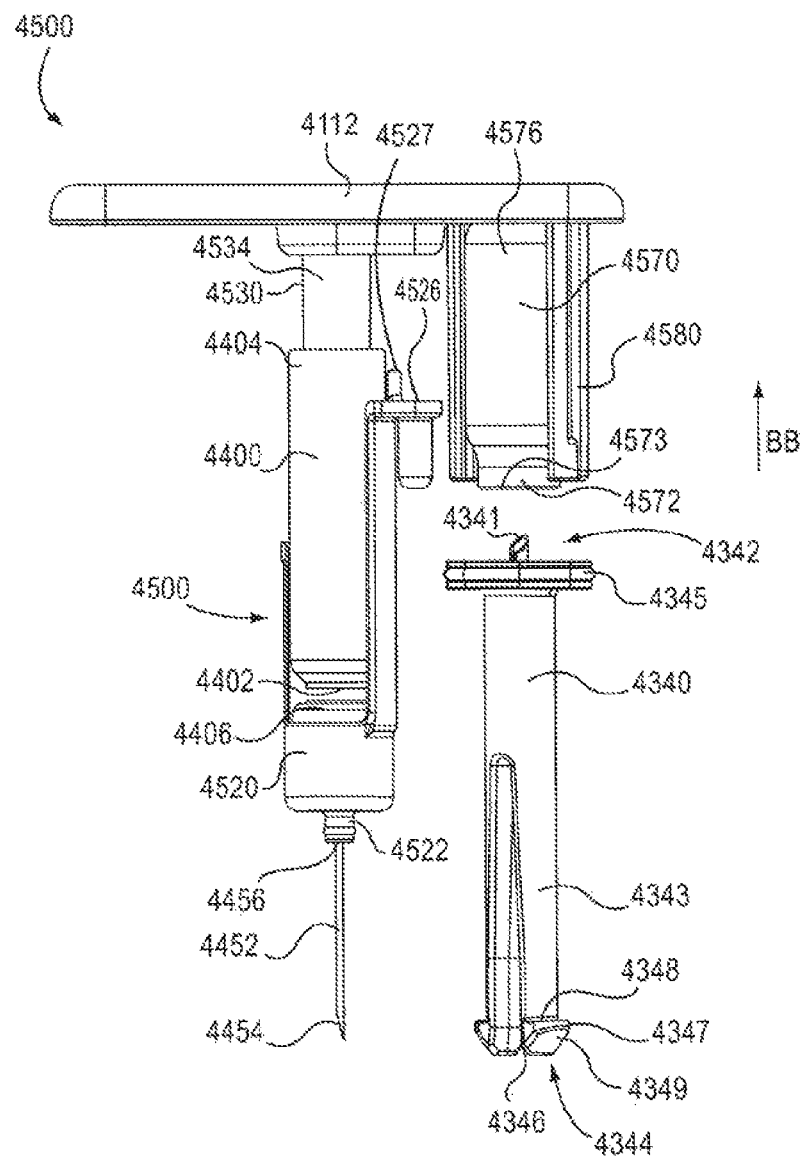

As shown in FIGS. 18 and 19, the housing 4110 defines a gas cavity 4154, a medicament cavity 4157 and an electronic circuit system cavity 4153. The gas cavity 4154 has a proximal end portion 4155 and a distal end portion 4156. The gas cavity 4154 is configured to receive the gas container 4570 and a portion of the system actuator assembly 4300 (e.g., the release member 4340 and the spring 4370, as shown in FIGS. 21 and 22) as described in further detail herein. The proximal end portion 4155 of the gas cavity 4154 is configured to receive the gas container retention member 4580 of the proximal cap 4112 of the housing 4110, as described in further detail herein. The gas cavity 4154 is in fluid communication with the medicament cavity 4157 via a gas passageway 4144 (see e.g., FIG. 20), as described in further detail herein, and the gas cavity 4154 is in fluid communication with a region outside the housing 4110 via a safety lock aperture 4128 (see e.g., FIGS. 18 and 19).

The medicament cavity 4157 is configured to receive the medicament container 4400 and a portion of the delivery mechanism 4500. In particular, the carrier 4520 and the moveable member 4530 of the medicament delivery mechanism 4500 are movably disposed in the medicament cavity 4157. The medicament cavity 4157 is in fluid communication with a region outside the housing 4110 via a needle aperture 4122 (see e.g., FIGS. 18 and 19).

The electronic circuit system cavity 4153 is configured to receive the electronic circuit system 4900. The housing 4110 has protrusions 4149 (see e.g., FIG. 17) configured to stabilize the electronic circuit system 4900 when the electronic circuit system 4900 is disposed within the electronic circuit system cavity 4153. The housing 4110 also defines connection apertures 4152 configured to receive connection protrusions 4171 of the electronic circuit system 4900, and aperture 4145 (see e.g., FIG. 15) configured to receive a portion of a protrusion 4174 of the electronic circuit system 4900. In this manner, the electronic circuit system 4900 can be coupled to the housing 4110 within the electronic circuit system cavity 4153. In other embodiments, the electronic circuit system 4900 can be coupled within the electronic circuit system cavity 4153 by other suitable means such as an adhesive, a clip, a label and/or the like.

The electronic circuit system cavity 4153 is fluidically and/or physically isolated from the gas cavity 4154 and/or the medicament cavity 4157 by a sidewall 4148. The sidewall 4148 can be any suitable structure to isolate the electronic circuit system cavity 4153 within the housing 4110 from the gas cavity 4154 and/or the medicament cavity 4157 within the housing 4110. Similarly, the gas cavity 4154 and the medicament cavity 4157 are separated by a sidewall 4146. In some embodiments, sidewall 4146 can be similar to the sidewall 4148, which isolates the gas cavity 4154 and the medicament cavity 4157 from the electronic circuit system cavity 4153. In other embodiments, the gas cavity 4154 can be fluidically and/or physically isolated from the medicament cavity 4157.

Figure 15:
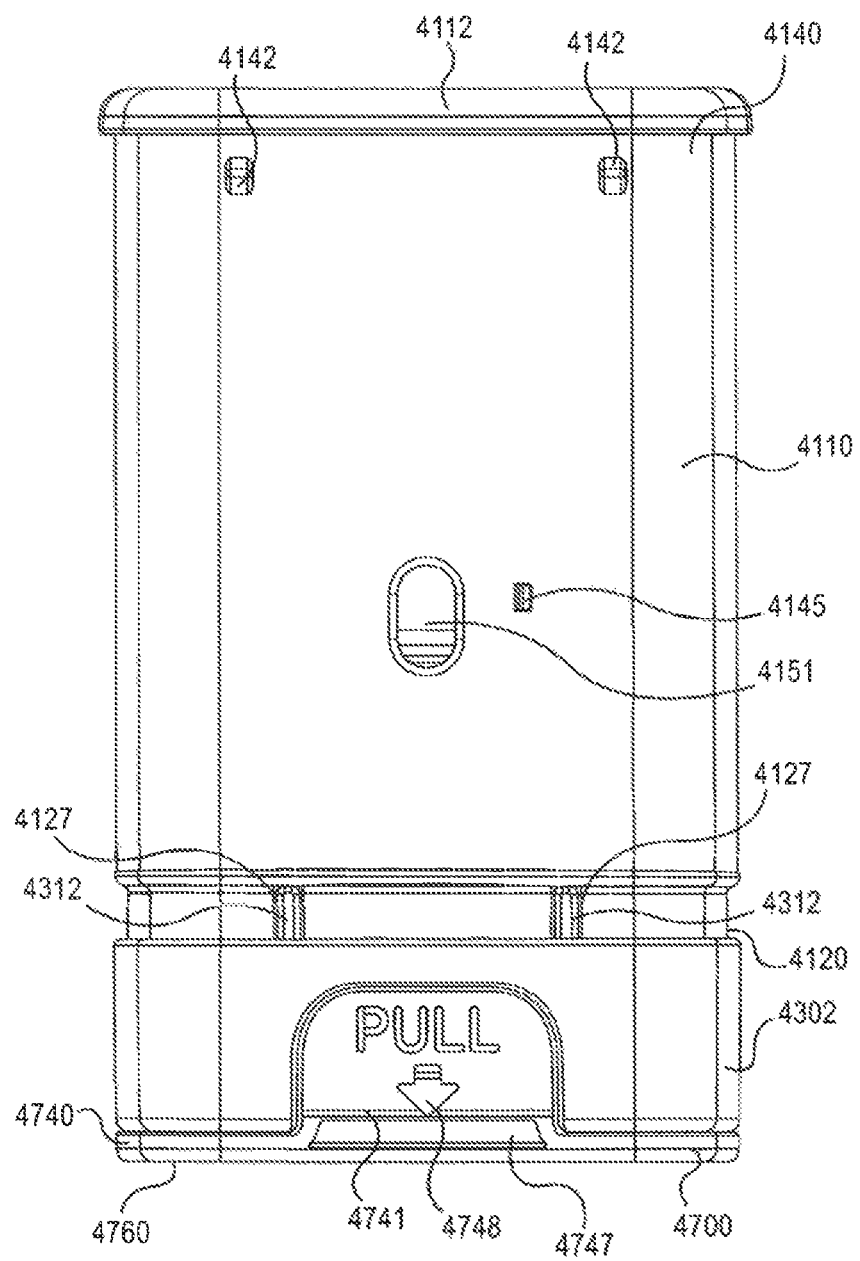
FIG. 15 is a back view of the medical injector illustrated in FIG. 12 with the cover removed.

The proximal end portion 4140 of the housing 4110 includes a proximal cap 4112, a speaker protrusion 4147 (see e.g., FIGS. 17 and 18), and cover retention protrusions 4142 (see e.g., FIGS. 13 and 15). The speaker protrusion 4147 is configured to maintain a position of an audio output device 4956 of the electronic circuit system 4900 relative to the housing 4110 when the electronic circuit system 4900 is attached to the housing 4110, as described herein. Cover retention protrusions 4142 are configured to be received within corresponding openings 4215 on the cover 4200. In this manner, as described in more detail herein, the cover 4200 can be removably coupled to and disposed about at least a portion of the housing 4110.

Figure 20:
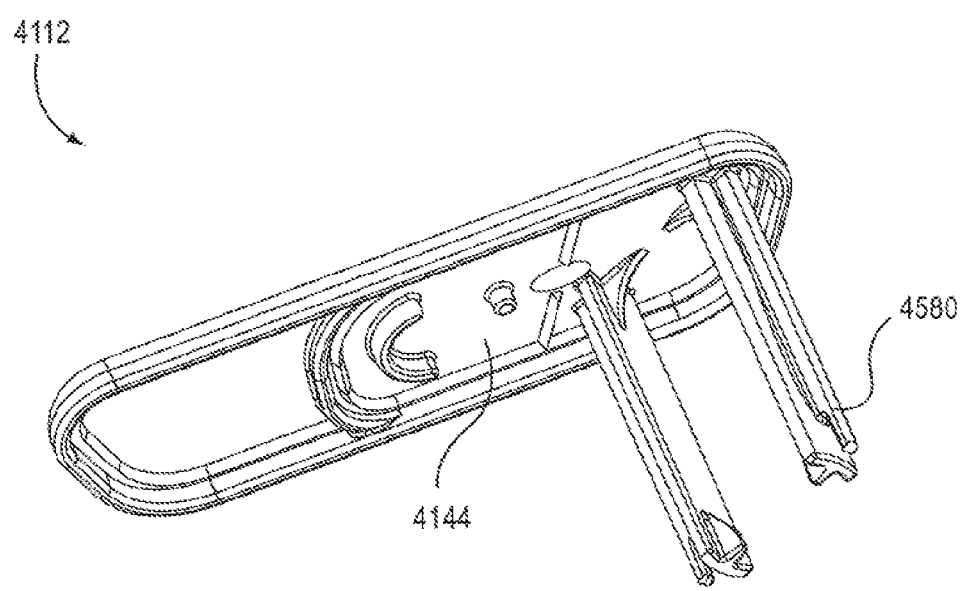
FIG. 20 is a perspective view of a proximal cap of the medical injector illustrated in FIG. 12.

As shown in FIG. 20, the proximal cap 4112 includes a gas container retention member 4580 and defines a gas passageway 4144. The gas container retention member 4580 is configured to receive and/or retain a gas container 4570 that can contain a pressurized gas. The gas passageway 4144 is configured to allow for the passage of gas contained in the gas container 4570 from the gas cavity 4154 to the medicament cavity 4157, as further described herein. Said another way, the gas passageway 4144 places the gas cavity 4154 in fluid communication with the medicament cavity 4157.

Figure 16:
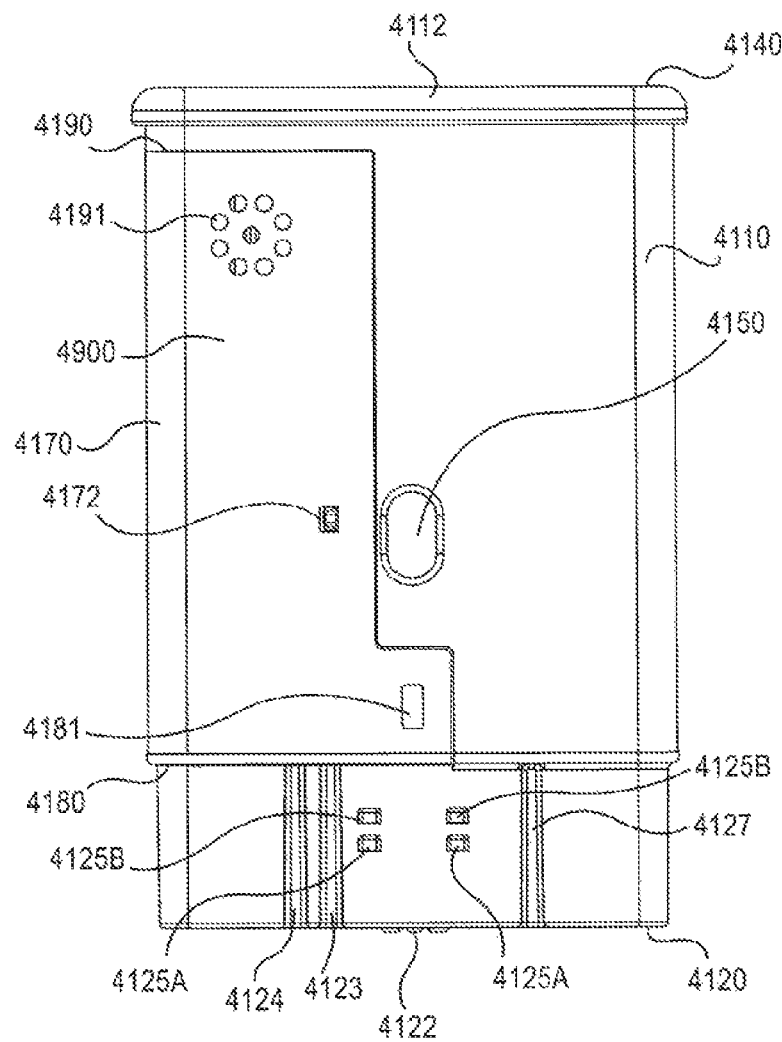
FIG. 16 is a front view of a portion of the medical injector illustrated in FIG. 12.
Figure 17:
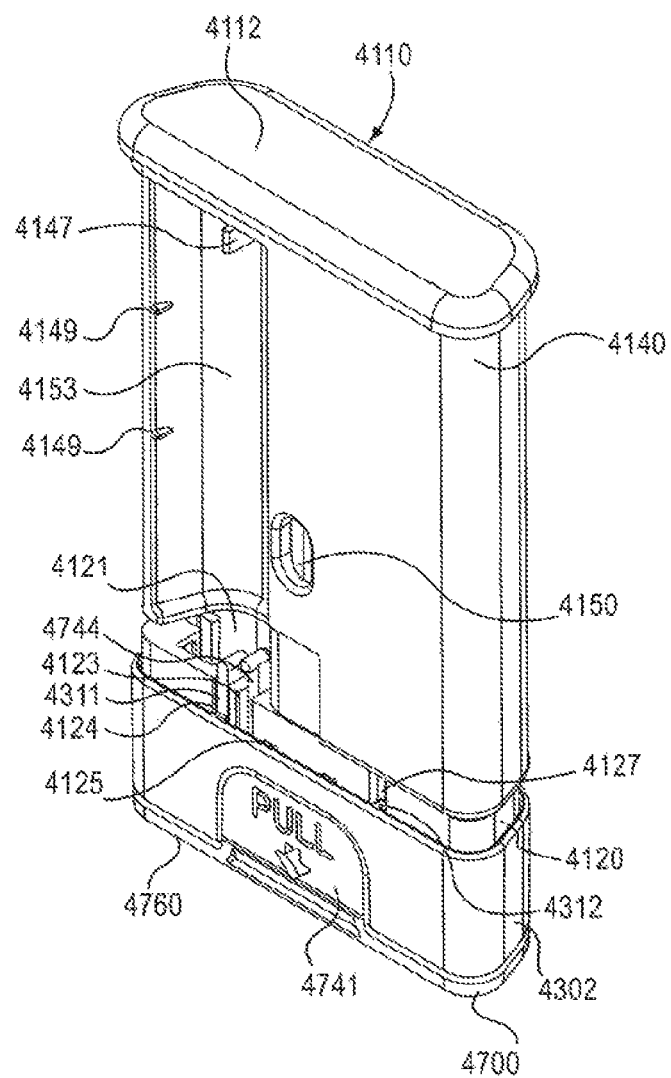
FIG. 17 is a perspective view of a portion of the medical injector illustrated in FIG. 12.

As shown in FIGS. 16 and 18, the distal end portion 4120 of the housing 4110 defines a battery isolation protrusion aperture 4121, a needle aperture 4122, a safety lock actuator groove 4123, a safety lock aperture 4128, a base actuator groove 4124, base retention recesses 4125A, 4125B, and base rail grooves 4127. The battery isolation protrusion aperture 4121 is configured to receive the battery isolation protrusion 4235 of the cover 4200 (see e.g., FIG. 38), as described in further detail herein.

The needle aperture 4122 is configured to allow the needle 4452 (see e.g., FIGS. 21, 47 and 48) to exit the housing 4110 when the medical injector 4000 is actuated. As described herein, the housing 4110, the base 4302, and the needle are configured such that the distal tip of the needle extends from the surface of the base 4302 by a predetermined distance (i.e., the needle extension) to produce the desired drug delivery characteristics. The portion of the sidewall of the housing 4110 that defines the needle aperture 4122 includes multiple sheath retention protrusions 4126. In some embodiments, the sheath retention protrusions can interact with a plurality of ribs 4728 of the needle sheath 4720 (see e.g. FIG. 42) to maintain a position of the needle sheath 4720 relative to the safety lock 4700 when the safety lock 4700 is coupled to the housing 4110 and/or when the safety lock 4700 is being removed from the housing 4110.

The safety lock actuator groove 4123 is configured to receive an actuator 4744 of the safety lock 4700. As described in more detail herein, the actuator 4744 is configured to engage and/or activate the electronic circuit system 4900 when the safety lock 4700 is moved with respect to the housing 4110. The safety lock aperture 4128 is configured to receive a safety lock protrusion 4742 (see e.g., FIGS. 38 and 39). As described in more detail below, when the medical injector is in the first configuration (i.e., when the safety lock 4700 is in place prior to use), the safety lock protrusion 4742 is disposed within an opening 4346 between extensions 4343 of a release member 4340 (see e.g., FIGS. 22 and 23) such that activation of the medical injector 4000 is prevented. The safety lock 4700, its components and functions are further described herein.

The distal base retention recesses 4125A are configured to receive the base connection knobs 4358 of the actuator 4302 (also referred to herein as "base 4302," see e.g., FIG. 43) when the base 4302 is in a first position relative to the housing 4110. The proximal base retention recesses 4125B are configured to receive the base connection knobs 4358 of the base 4302 when the base 4302 is in a second position relative to the housing 4110. The base retention recesses 4125A, 4125B have a tapered proximal sidewall and a non-tapered distal sidewall. This allows the base retention recesses 4125A, 4125B to receive the base connection knobs 4358 such that the base 4302 can move proximally relative to the housing 4110, but cannot move distally relative to the housing 4110. Said another way, the distal base retention recesses 4125A are configured to prevent the base 4302 from moving distally when the base 4302 is in a first position and the proximal base retention recesses 4125B are configured to prevent the base 4302 from moving distally when the base 4302 is in a second position. Similarly stated, the proximal base retention recesses 4125B and the base connection knobs 4358 cooperatively prevent "kickback" after the medical injector 4000 is actuated.

Moreover, the engagement between the distal base retention recesses 4125A and the base connection knobs 4358 when the base 4302 is in the first position is such that the base 4302 cannot be moved proximally to actuate the device until an actuation force exceeds a minimum value. In this manner, the likelihood of inadvertently actuating the device 4000 is reduced. Moreover, the distal base retention recesses 4125A and the base connection knobs 4358 can be configured such that an upper limit required to move the base 4302 proximally does not exceed an amount that could lead to patient discomfort or excessive compression of the tissue at the target location. For example, in some embodiments, the distal base retention recesses 4125A and the base connection knobs 4358 can be configured such that the force applied by the distal contact surface 4330 to actuate the device 4000 is between about 8.9 N (2 lbf) and about 44.5 N (10 lbf). In other embodiments, the distal base retention recesses 4125A and the base connection knobs 4358 can be configured such that the force applied by the distal contact surface 4330 to actuate the device 4000 is about 26.7 N (6 lbf).

Moreover, the distal contact surface 4330 described herein can have an area that, taken in conjunction with the actuation force, produces a pressure against the target location that is within a desired range. In some embodiments, the distal contact surface 4330 can have a contact area between about 322 mm$^2$ (about 0.5 square inches) and about 645 mm$^2$ (about 1 square inch). Such contact area can exclude any openings, cut-outs, or the like. In other embodiments, the contact area can be greater than about 645 mm$^2$ (about 1 square inch). For example, in some embodiments the contact area of any of the contact surfaces described herein (including the contact surfaces 1330, 2330, 3300, 4330) can be between about 645 mm$^2$ (about 1 square inch) and about 968 mm$^2$ (about 1.5 square inches) or between about 645 mm$^2$ (about 1 square inch) and about 1290 mm$^2$ (about 2 square inches).

The base actuator groove 4124 is configured to receive an actuator 4311 of the base 4302. As described in more detail herein, the actuator 4311 of the base 4302 is configured to engage the electronic circuit system 4900 when the base 4302 is moved with respect to the housing 4110. The base rail grooves 4127 are configured to receive the guide members 4312 of the base 4302. The guide members 4312 of the base 4302 and the base rail grooves 4127 of the housing 4110 engage each other in a way that allows the guide members 4312 of the base 4302 to slide in a proximal and/or distal direction within the base rail grooves 4127 while limiting lateral movement of the guide members 4312. This arrangement allows the base 4302 to move in a proximal and/or distal direction with respect to the housing 4110 but prevents the base 4302 from moving in a lateral direction with respect to the housing 4110.

FIGS. 21-24 show the medicament container 4400, the system actuator assembly 4300 and the medicament delivery mechanism 4500 of the medical injector 4000. The medical injector 4000 is similar to the auto-injectors described in U.S. Pat. No. 7,648,482, entitled "Devices, Systems and Methods for Medicament Delivery," filed Nov. 21, 2006, which is incorporated herein by reference in its entirety.

Figure 24:
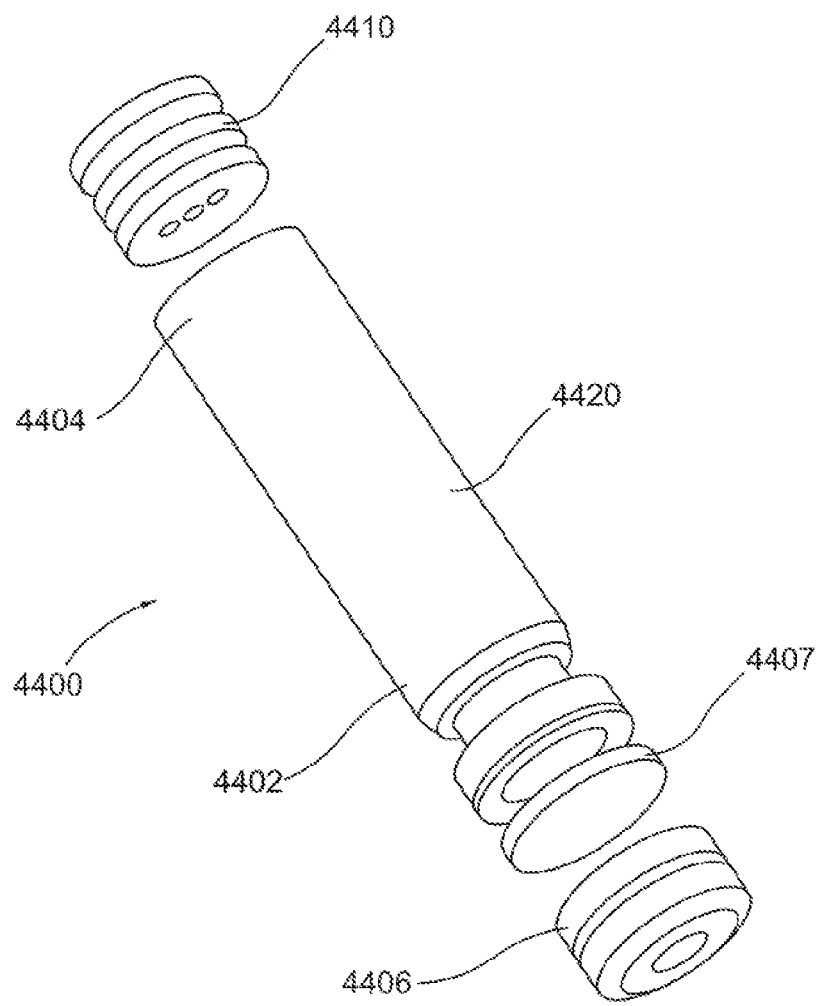
FIG. 24 is an exploded view of a medicament container of the medical injector illustrated in FIG. 12.
Figure 25:
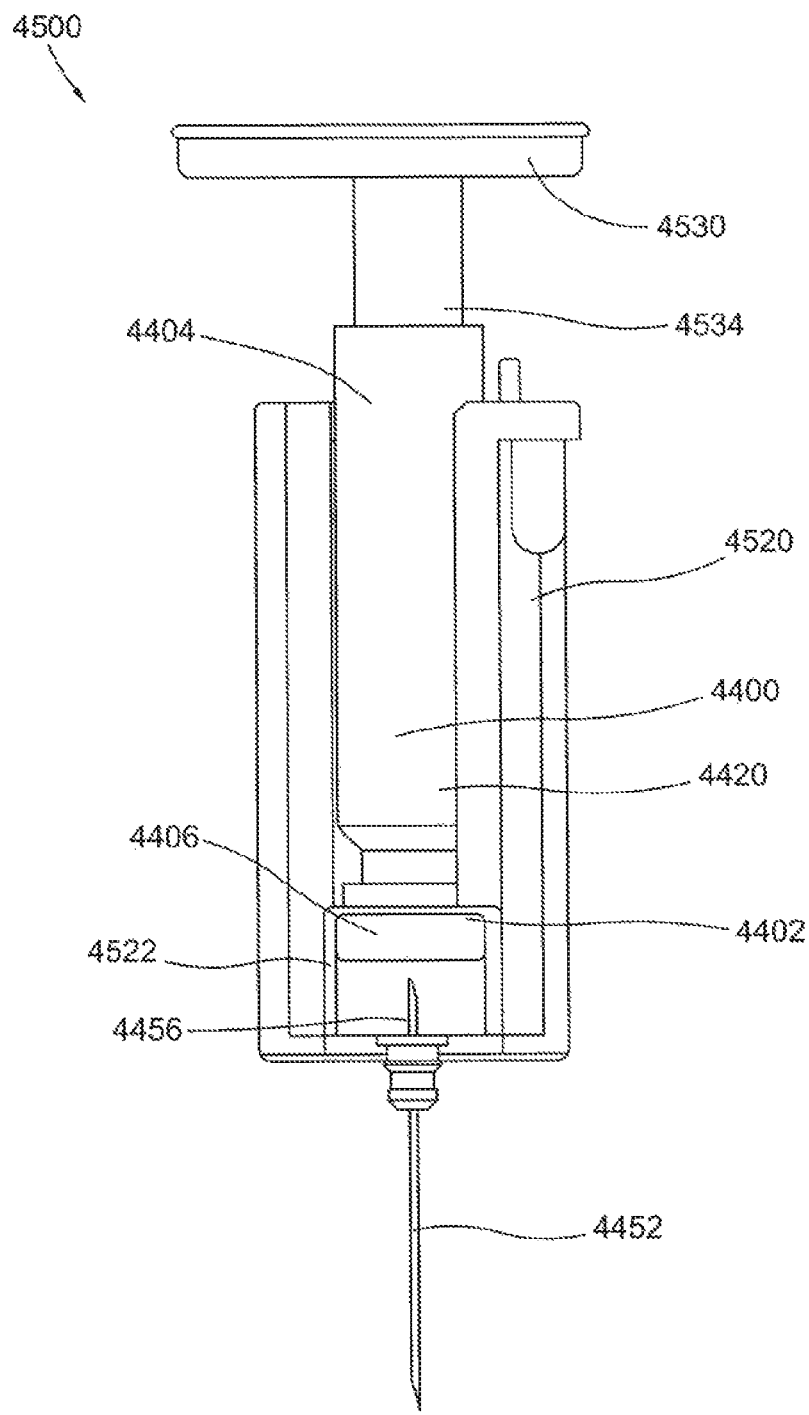
FIG. 25 is a front view of a portion of the medical injector illustrated in FIG. 12.
Figure 26:
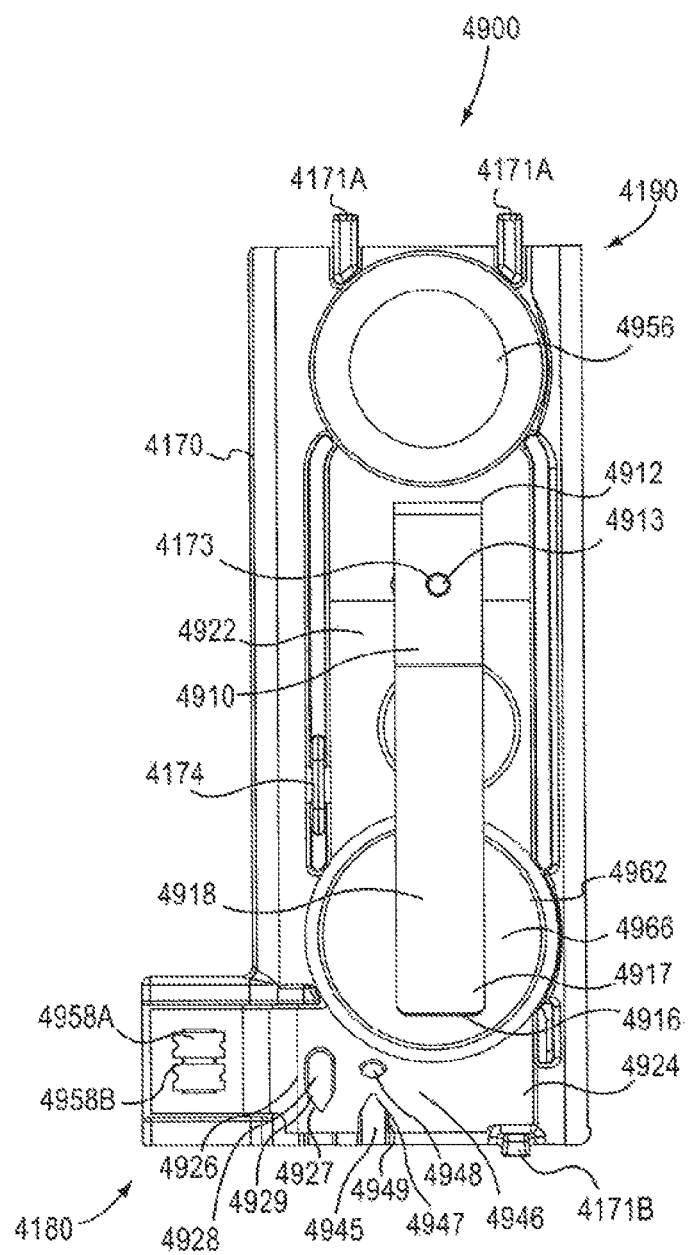
FIG. 26 is a back view of an electronic circuit system of the medical injector illustrated in FIG. 12.
Figure 27:
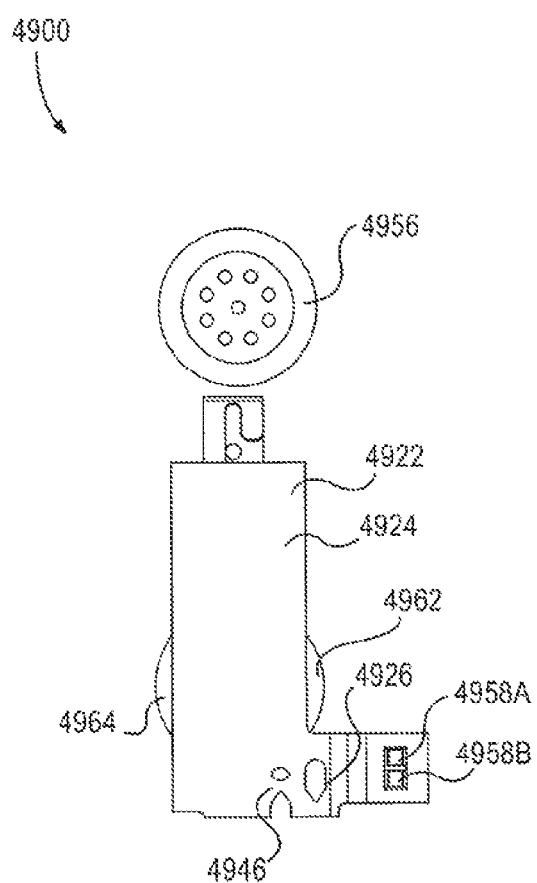
FIG. 27 is a front view of a portion of the electronic circuit system of the medical injector illustrated in FIG. 26.
Figure 28:
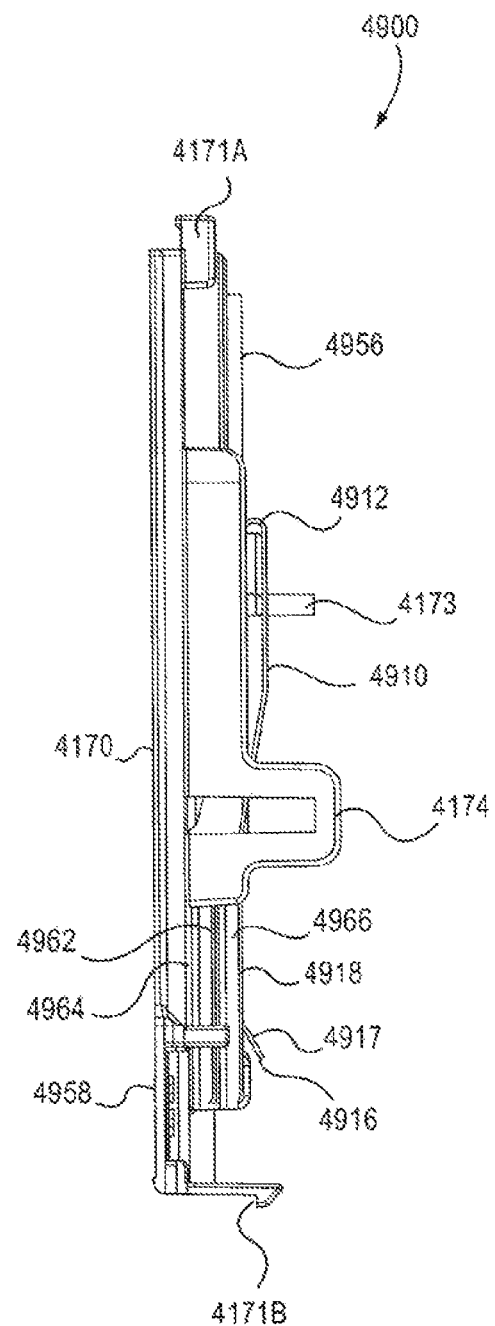
FIG. 28 is a side view of the electronic circuit system of the medical injector illustrated in FIG. 26.

The medicament container 4400 of the medicament delivery mechanism 4500 has a distal end portion 4402 and a proximal end portion 4404, and contains (i.e., is filled with or partially filled with) an epinephrine composition 4420 (see, e.g., FIG. 24). The distal end portion 4402 of the medicament container 4400 contains a seal 4406. The seal 4406, which can be, for example, an 8-I crimp seal, is configured to burst when punctured by the proximal end 4456 of the needle 4452, as described below. The proximal end portion 4404 of the medicament container 4400 includes an elastomeric member 4410, and is configured to receive a piston portion 4534 of the movable member 4530. Although the medicament container 4400 is shown in FIG. 24 as including a liner 4407, in other embodiments, the medicament container 4400 need not include the liner 4407.

The medicament container 4400 can have any suitable size (e.g., length and/or diameter) and can contain any suitable volume of the epinephrine composition 4420. Moreover, the medicament container 4400 and the movable member 4530 can be collectively configured such that the movable member 4530 travels a desired distance within the medicament container 4400 (i.e., the "stroke") during an injection event. In this manner, the medicament container 4400, the volume of the epinephrine composition 4420 within the medicament container 4400 and the movable member 4530 can be collectively configured to provide a desired fill volume and delivery volume. In some embodiments, for example, the size of the medicament container 4400 and the length of the movable member 4530 can be such that the fill volume of the epinephrine composition 4420 is approximately 0.76 mL and the delivery volume of the epinephrine composition 4420 is approximately 0.30 mL (providing a delivery volume to fill volume ratio of approximately 0.4). The 0.3 mL dose is used for patients experiencing anaphylaxis and having a weight of 30 kg or more. In other embodiments, for example, the size of the medicament container 4400 and the length of the movable member 4530 can be such that the fill volume of the epinephrine composition 4420 is approximately 0.76 mL and the delivery volume of the epinephrine composition 4420 is approximately 0.15 mL (providing a delivery volume to fill volume ratio of approximately 0.2). The 0.15 mL dose is used for patients experiencing anaphylaxis and having a weight of between about 15 kg and about 30 kg. In yet other embodiments, for example, the size of the medicament container 4400 and the length of the movable member 4530 can be such that the fill volume of the epinephrine composition 4420 is approximately 0.76 mL and the delivery volume of the epinephrine composition 4420 is approximately 0.10 mL (providing a delivery volume to fill volume ratio of approximately 0.13). The 0.1 mL dose is used for patients experiencing anaphylaxis and having a weight of less than about 15 kg (and more specifically, between 7.5 kg and 15 kg).

Moreover, the length of the medicament container 4400, the length of the carrier 4520, and the length of the movable member 4530 can be configured such that the medicament delivery mechanism 4500 can fit in the same housing 4110 regardless of the fill volume, the delivery volume and/or the ratio of the fill volume to the delivery volume. In this manner, the same housing and production tooling can be used to produce devices having various dosages of the epinephrine composition. For example, in a first ("adult-dose") embodiment, the drug product 4000 has a fill volume to delivery volume ratio of 0.4, and configured to deliver 0.3 mL epinephrine. In this embodiment, the medicament container has a first length, the carrier has a first length, and the movable member has a first length. In a second ("pediatric-dose") embodiment, the drug product 4000 has a fill volume to delivery volume ratio of 0.2, and is configured to deliver 0.15 mL epinephrine. In this embodiment, the medicament container and the movable member can have the same length (i.e., they can be identical to those used with the "adult-dose" embodiment), but the carrier has a second length longer than the first length. In this manner, the stroke of the device of the second embodiment is shorter than that of the device of the first embodiment, thereby expelling a lower dosage. In particular, the gas valve actuator 4527 of the carrier 4520 can be longer, thereby releasing the gas valve earlier in the stroke. Finally, in a second ("infant-dose") embodiment, the drug product 4000 has a fill volume to delivery volume ratio of 0.13, and is configured to deliver 0.1 mL epinephrine. In this embodiment, the medicament container and the movable member can have the same length (i.e., they can be identical to those used with the "adult-dose" embodiment), but the carrier has a third length longer than the first length. In this manner, the stroke of the device of the second embodiment is shorter than that of the device of the first or second embodiments, thereby expelling a lower dosage.

The epinephrine composition 4420 contained within the medicament container 4400 can be any of the epinephrine compositions described herein. In particular, the epinephrine composition 4420 can include an effective amount of epinephrine, i.e., (−)-3,4-Dihydroxy-α-[(methylamino)methyl] benzyl alcohol. In some embodiments, the medicament container contains approximately 0.76 mL epinephrine solution, with each 0.1 mL contains 0.1 mg of epinephrine, 0.78 mg of sodium chloride, 0.15 mg of sodium bisulfite, and hydrochloric acid to adjust the pH. In some embodiments, the medicament container 4400 and/or the drug product 4000 contains a dose of epinephrine effective for administration to a patient experiencing anaphylaxis and having a weight of greater than about 30 kg (66 pounds), i.e., an adult-dose auto-injector that delivers 0.3 mg of epinephrine. In other embodiments, the medicament container 4400 and/or the drug product 4000 contains a dose of epinephrine effective for administration to a patient experiencing anaphylaxis and having a weight of between about 15 kg (33 pounds) and about 30 kg (66 pounds), i.e., a pediatric-dose auto-injector that delivers 0.15 mg of epinephrine. In yet other embodiments, the medicament container 4400 and/or the drug product 4000 contains a dose of epinephrine effective for administration to a patient experiencing anaphylaxis and having a weight of less than about 15 kg (33 pounds), and more specifically between about 7.5 kg (17 pounds) and about 15 kg, i.e., an infant-dose auto-injector that delivers 0.10 mg of epinephrine.

The elastomeric member 4410 can be of any design or formulation suitable for contact with the epinephrine composition 4420. For example, the elastomeric member 4410 can be formulated to minimize any reduction in the efficacy of the epinephrine composition 4420 that may result from contact (either direct or indirect) between the elastomeric member 4410 and the epinephrine composition 4420. For example, in some embodiments, the elastomeric member 4410 can be formulated to minimize any leaching or outgassing of compositions that may have an undesired effect on the epinephrine composition 4420. In other embodiments, the elastomeric member 4410 can be formulated to maintain its chemical stability, flexibility and/or sealing properties when in contact (either direct or indirect) with epinephrine over a long period of time (e.g., for up to six months, one year, two years, five years or longer). In some embodiments, the elastomeric member 4410 can include or be composed of bromo-butyl rubber.

As shown in FIG. 21, the system actuator 4300 includes the base 4302, a release member 4340 and a spring 4370. FIG. 22 shows certain of the internal components of the medical injector 4000 without the base 4302 and the spring 4370 so that the release member 4340 can be more clearly shown.

The release member 4340 has a proximal end portion 4342 and a distal end portion 4344, and is movably disposed within the distal end portion 4156 of the gas cavity 4154.

The proximal end portion 4342 of the release member 4340 includes a sealing member 4345 and a puncturer 4341. The sealing member 4345 is configured to engage the sidewall of the housing 4110 defining the gas cavity 4154 such that the proximal end portion 4155 of the gas cavity 4154 is fluidically isolated from the distal end portion 4156 of the gas cavity 4154. In this manner, when gas is released from the gas container 4570, the gas contained in the proximal end portion 4155 of the gas cavity 4154 is unable to enter the distal end portion 4156 of the gas cavity 4154. The puncturer 4341 of the proximal end portion 4342 of the release member 4340 is configured to contact and puncture a frangible seal 4573 on the gas container 4570 when the release member 4340 moves proximally within the gas cavity 4154, as shown by the arrow BB in FIG. 22.

Figure 23:
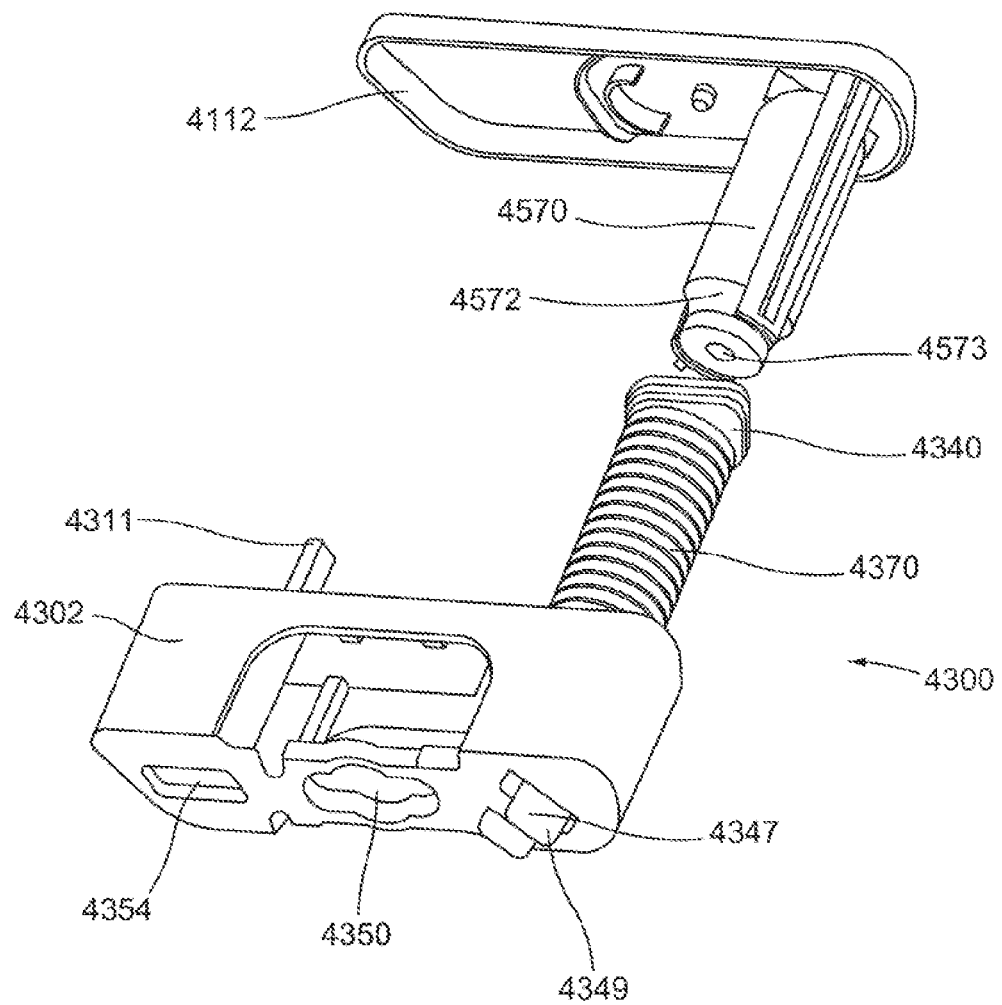
FIG. 23 is a perspective view of a portion of the medical injector illustrated in FIG. 12.

The distal end portion 4344 of the release member 4340 includes extensions 4343. The extensions 4343 include projections 4347 that include tapered surfaces 4349 and engagement surfaces 4348. Further, the extensions 4343 define an opening 4346 between the extensions 4343. The engagement surfaces 4348 of the projections 4347 are configured to extend through the safety lock aperture 4128 of the housing 4110 and contact a distal surface of the housing 4110, as shown in FIG. 23. In this manner, the engagement surfaces 4348 of the projections 4347 limit proximal movement of the release member 4340 when the engagement surfaces 4348 are in contact with the distal surface of the housing 4110.

Figure 35:
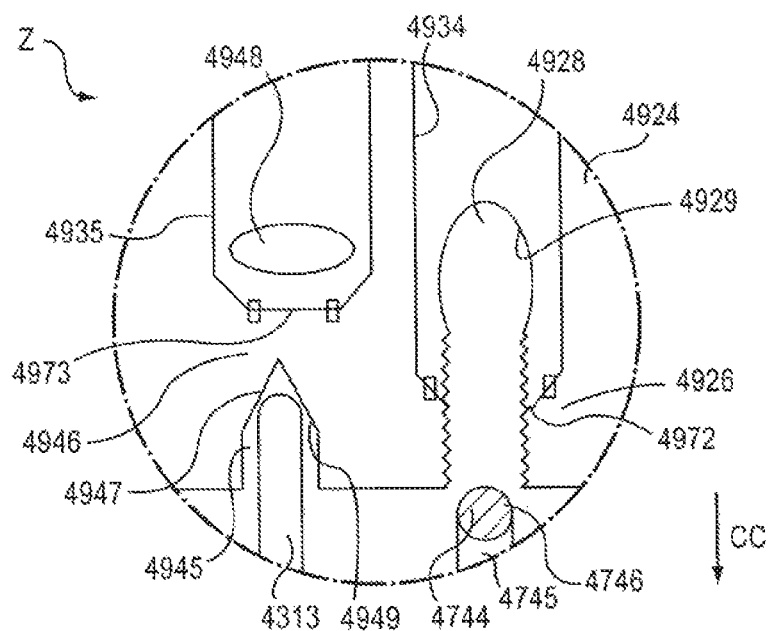

The opening 4346 defined by the extensions 4343 is configured to receive the safety lock protrusion 4742 of the safety lock 4700 (see e.g., FIGS. 23 and 35). The safety lock protrusion 4742 is configured to prevent the extensions 4343 from moving closer to each other. Said another way, the safety lock protrusion 4742 is configured to ensure that the extensions 4343 remain apart and the engagement surfaces 4348 of the projections 4347 remain in contact with the distal end portion 4120 of the housing 4110. In some embodiments, for example, the release member 4340 and/or the extensions 4343 can be constructed from any suitable material configured to withstand deformation that may occur when exposed to a load over an extended period of time. In some embodiments, for example, the release member 4340 and/or the extensions 4343 can be constructed from brass.

The tapered surfaces 4349 of the projections 4347 are configured to contact protrusions 4313 on a proximal surface 4310 of the base 4302 (see e.g., FIG. 43) when the base 4302 is moved proximally relative to the housing 4110. Accordingly, when the base 4302 is moved proximally relative to the housing 4110, the extensions 4343 are moved together by the contact protrusions 4313. The inward movement of the extensions 4343 causes the release member 4340 to become disengaged from the distal end portion of the housing 4110, thereby allowing the release member 4340 to be moved proximally along its longitudinal axis as the spring 4370 expands.

The medicament delivery mechanism 4500 includes a gas container 4570, a carrier 4520, a movable member 4530, and a retraction spring 4590. As described above, the carrier 4520 and the movable member 4530 are disposed within the medicament cavity 4157 of the housing 4110. The gas container 4570 is disposed within the gas cavity 4154 of the housing 4110.

The gas container 4570 includes a distal end portion 4572 and a proximal end portion 4576, and is configured to contain a pressurized gas. The distal end portion 4572 of the gas container 4570 contains a frangible seal 4573 configured to break when the puncturer 4341 of the proximal end portion 4342 of the release member 4340 contacts the frangible seal 4573. The gas container retention member 4580 of the proximal cap 4112 of the housing 4110 is configured to receive and/or retain the proximal end portion 4576 of the gas container 4570. Said another way, the position of the gas container 4570 within the gas cavity 4154 is maintained by the gas container retention member 4580.

The movable member 4530 of the medicament delivery mechanism 4500 is movably disposed within the medicament cavity 4157. The movable member 4530 includes a piston portion 4534 having a plunger at the distal end portion of the piston portion 4534. The piston portion 4534 is configured to move within the medicament container 4400. In this manner, the piston portion 4534 of the movable member 4530 can apply a force to the elastomeric member 4410 to convey the epinephrine composition 4420 contained in the medicament container 4400. The piston portion 4534 can be constructed of a resilient, durable, and/or sealing material, such as a rubber.

The carrier 4520 of the medicament delivery mechanism 4500 includes a distal end portion 4522 and a proximal end portion 4526. The needle 4452 is coupled within the distal end portion 4522 such that the proximal end tip 4456 can be selectively inserted into the medicament container 4400, as described below. The needle 4452, as well as any other needles shown and described herein, can have any diameter and/or length to facilitate the injection of the epinephrine composition 4420 according to the methods described herein. For example, the needle can have a length suitable to penetrate clothing and deliver the epinephrine via a subcutaneous injection and/or an intramuscular injection. In some embodiments, the needle 4452 (and any needle disclosed herein) can have a length such that, in use, the distal tip 4454 extends from the contact surface 4330 by distance $D_N$ (see FIG. 47) sufficient such that the distal tip 4454 is in the muscle layer of the target location. Specifically, in some embodiments, the distance $D_N$ (or effective needle length) is such that the distal tip 4454 will be inserted within the thigh muscle for a patient weighing less than 15 kg (and more specifically between about 7.5 kg and about 15 kg), and will have a low likelihood of striking the thigh bone. In this manner, the distance $D_N$ is sufficient to produce an intramuscular delivery of the epinephrine 4420 while also limiting the likelihood of either an intraosseous delivery or a subcutaneous delivery. For example, in some embodiments, the distance $D_N$ is between about 6.35 mm and about 9 mm. In other embodiments, the distance $D_N$ is between about 7 mm and about 8 mm. In yet other embodiments, the distance $D_N$ is about 7.5 mm.

The needle 4452 defines a lumen that can be selectively placed in fluid communication with the medicament container 4400 to define a medicament delivery path through which the epinephrine composition 4420 can flow. The needle 41452 can be any gauge (e.g., 18 gauge, 23 gauge, 24 gauge, 25 gauge, 27 gauge, 32 gauge, etc.) to deliver the epinephrine composition 1420 through the lumen and into the target location of body (not shown). The distal end tip 1454 can have any suitable bevel or shape.

The medicament container 4400 is coupled to the carrier 4520 via a "snap-fit" connection (not shown) such that the medicament container 4400 can move relative to the carrier 4520 between a first configuration and a second configuration during an injection event. In the first configuration (see FIG. 25), the carrier 4520 is configured to move within the medicament cavity 4157 such that movement of the carrier 4520 within the medicament cavity 4157 causes contemporaneous movement of the medicament container 4400 within the medicament cavity 4157. The proximal end portion 4456 of the needle 4452 is spaced apart from the seal 4406 of the medicament container 4400 when the carrier 4520 and the medicament container 4400 are collectively in the first configuration (e.g., during needle insertion). When the carrier 4520 and the medicament container 4400 are moved to the second configuration, the medicament container 4400 releases from the "snap-fit" causing the medicament container 4400 to move distally with respect to the carrier 4520, causing the proximal end portion 4456 of the needle 4452 to pierce the seal 4406. In this manner, the needle 4452 can be selectively placed in fluid communication with the medicament container 4400 to define a medicament delivery path (not shown).

Figure 49:
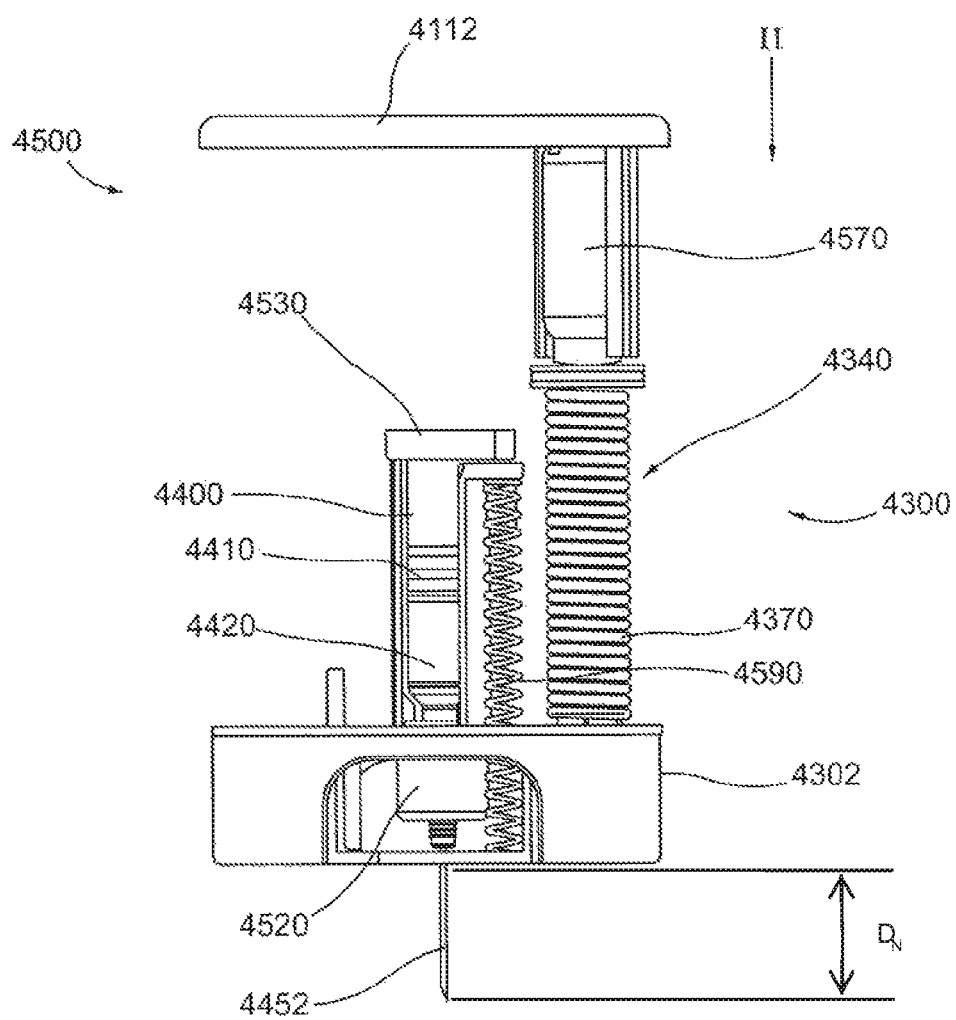
FIG. 49 is a front view of the medical injector illustrated in FIG. 12 in a fifth configuration (i.e., the injection configuration).

As shown in FIGS. 21, 22 and 49, the proximal end portion 4526 of the carrier 4520 includes a gas valve actuator 4527. The gas valve actuator 4527 is configured to engage a gas relief valve (not shown) of the movable member 4530 to allow the pressurized gas contained within the gas chamber (i.e., the volume within the medicament cavity 4157 between the proximal end of the housing 4110 and the proximal end of the movable member 5530) to escape when the injection event is complete. Thus, after the gas pressure within the medicament cavity 4157 decreases below a certain level, the force exerted by the retraction spring 4590 on the carrier 4520 can be sufficient to cause the carrier 4520 to move proximally within the housing 4110 (i.e., to retract). In addition, this arrangement results in there being substantially no residual force within the housing, which decreases stress on the components after the injection event.

As described above, the length of the carrier 4520 and/or the gas valve actuator 4527 can determine the point along the travel of the movable member 4530 at which the gas relief valve is actuated. In this manner, the length of the carrier 4520 and/or the gas valve actuator 4527 can determine the "stroke" of the movable member, and therefore, the volume of epinephrine delivered. Moreover, the tolerance of this dimension (along with the tolerance of the medicament container 4400 dimensions) can impact the accuracy of the dose delivered.

Figure 32:
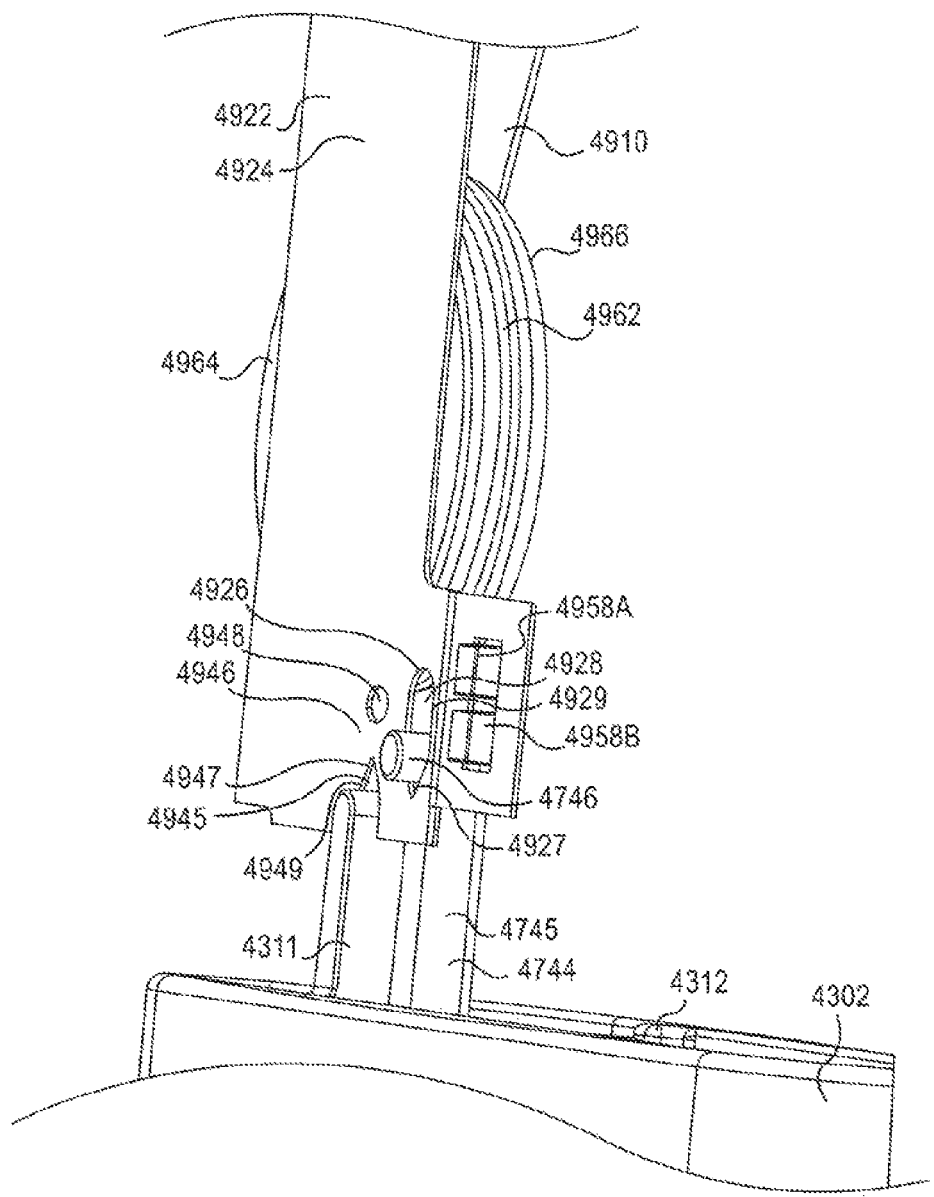
FIG. 32 is a perspective view of a portion of an electronic circuit system of the medical injector illustrated in FIG. 12, in a first configuration.
Figure 33:
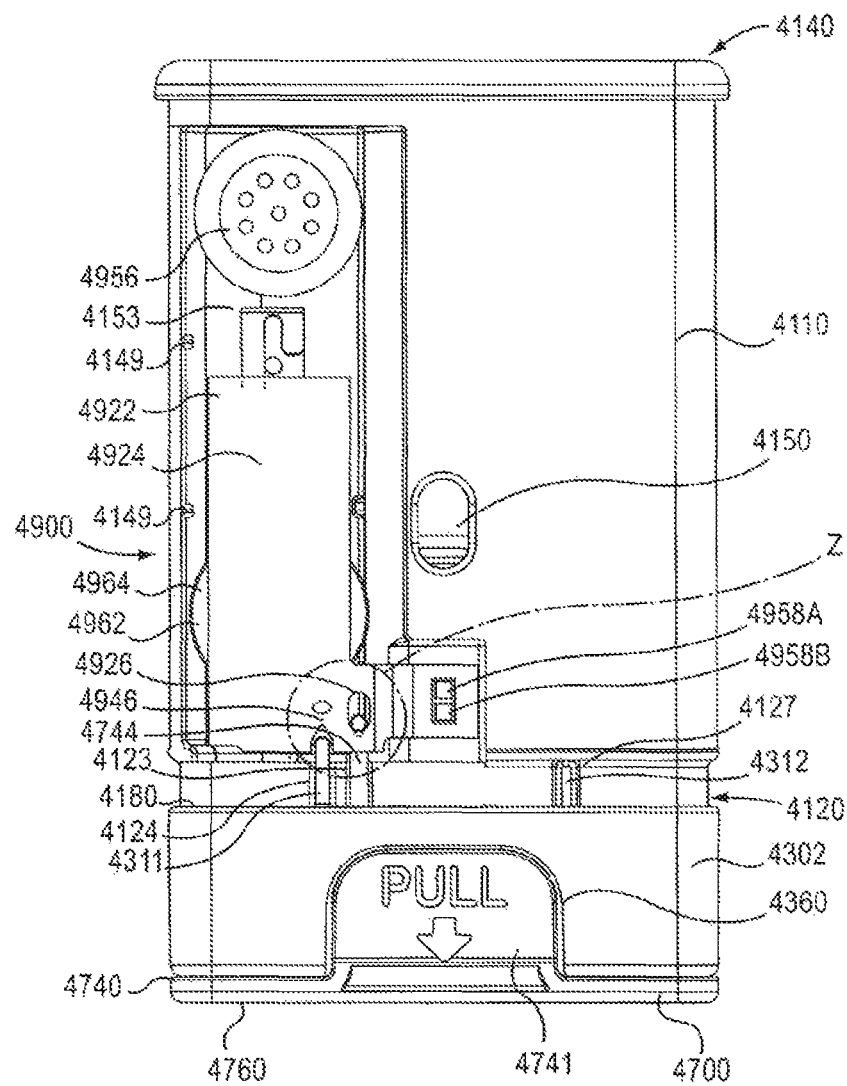
FIG. 33 is a front view of the medical injector illustrated in FIG. 12 in a first configuration showing the electronic circuit system.

FIGS. 26-36 show the electronic circuit system 4900. The electronic circuit system 4900 of the medical injector 4000 includes an electronic circuit system housing 4170, a printed circuit board 4922, a battery assembly 4962, an audio output device 4956, two light emitting diodes (LEDs) 4958A, 4958B and a battery clip 4910. As shown in FIG. 33, the electronic circuit system 4900 is configured to fit within the electronic circuit system cavity 4153 of the housing 4110. Accordingly, as described above, the electronic circuit system 4900 is physically and/or fluidically isolated from the medicament cavity 4157, the gas cavity 4154 and/or the medicament delivery device 4500. As described herein, the electronic circuit system 4900 is configured to output an electronic output associated with the use of the medical injector 4000.

The electronic circuit system housing 4170 of the electronic circuit system 4900 includes a distal end portion 4180 and a proximal end portion 4190. The proximal end portion 4190 includes connection protrusions 4171A and a battery clip protrusion 4173. The connection protrusions 4171A extend from the proximal end portion 4190 of the electronic circuit system housing 4170, and are configured to be disposed within the connection apertures 4152 of the housing 4110, as described above. In this manner, the electronic circuit system 4900 can be coupled to the housing 4110 within the electronic circuit system cavity 4153. In other embodiments, the electronic circuit system 4900 can be coupled to the housing 4110 by other suitable means such as an adhesive, a clip, a label and/or the like. As described in more detail herein, the battery clip protrusion 4173 is configured to hold the battery clip 4910 in place.

The proximal end portion 4190 of the electronic circuit system housing 4170 defines multiple sound apertures 4191. The audible output device 4956 is disposed against the proximal end portion 4190 of the electronic circuit system housing 4170 such that the front face of the audible output device 4956 is disposed adjacent the sound apertures 4191. In this manner, the sound apertures 4191 are configured to allow sound from an audio output device 4956 to pass from the audio output device 4956 to a region outside of the housing 4110.

Figure 29:
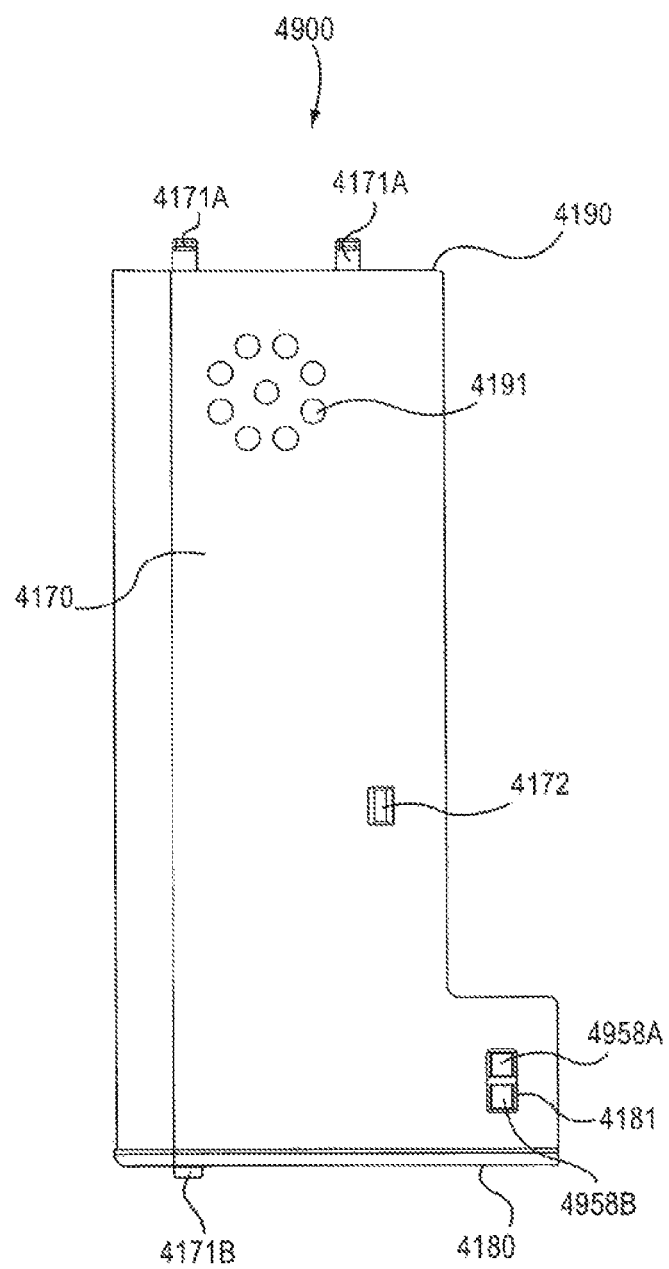
FIG. 29 is a front view of an electronic circuit system housing of the electronic circuit system illustrated in FIG. 26.
Figure 30:
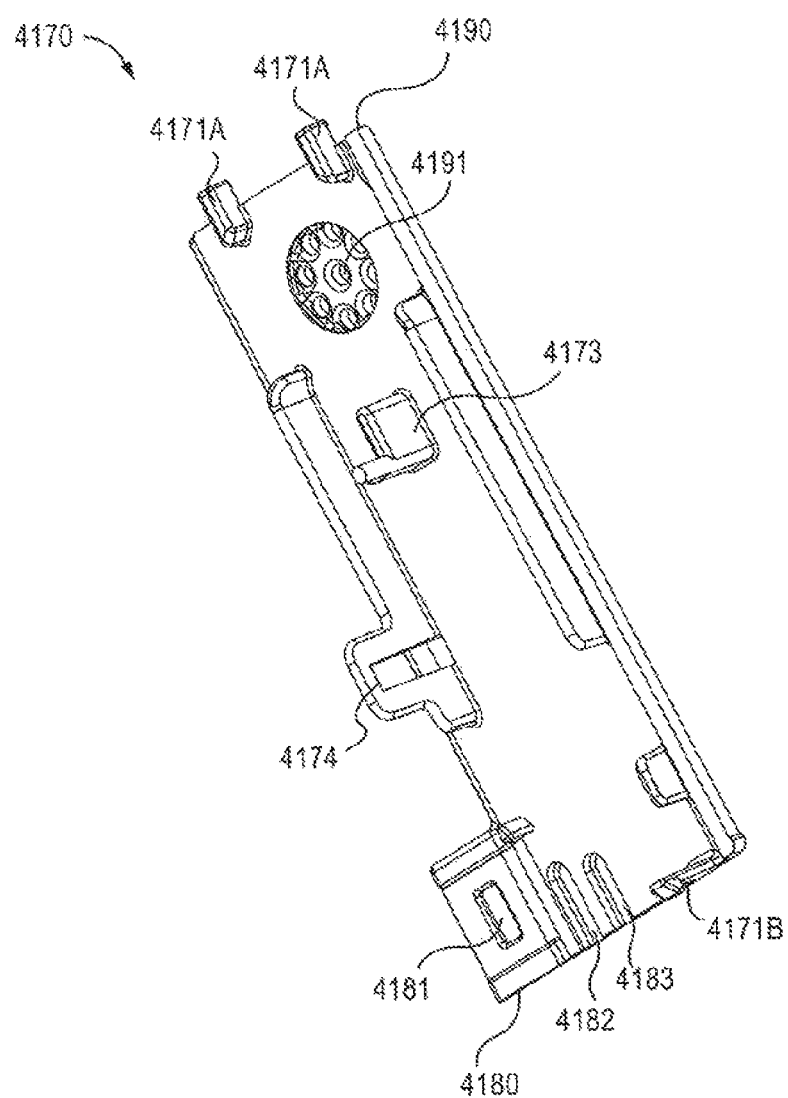
FIG. 30 is a perspective view of the electronic circuit system housing of the electronic circuit system illustrated in FIG. 29.
Figure 31:
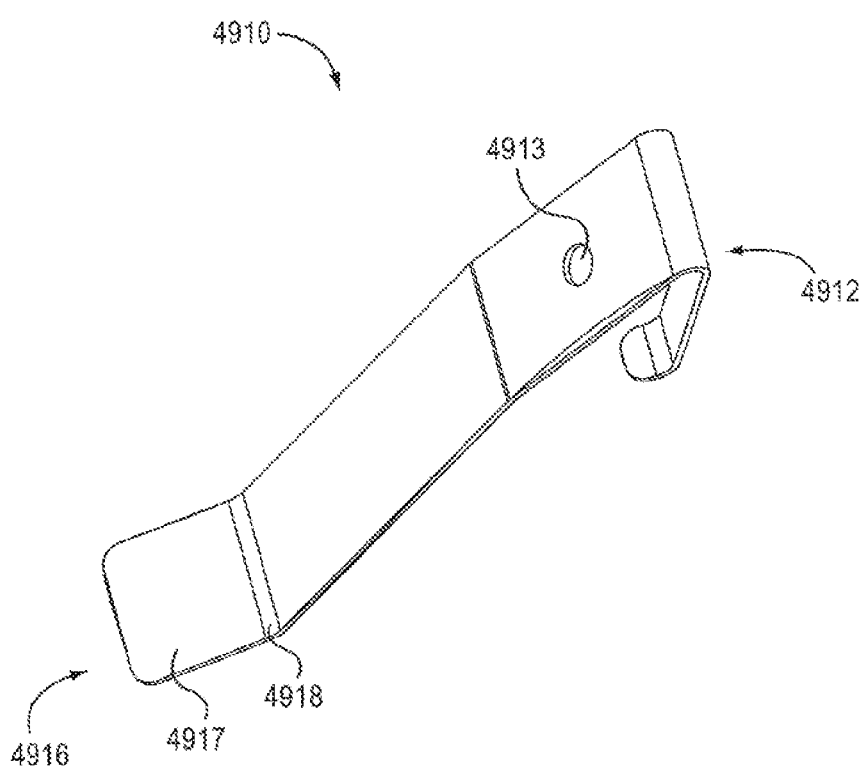
FIG. 31 is a perspective view of a battery clip of the electronic circuit system illustrated in FIG. 26.

As shown in FIGS. 29 and 30, the distal end portion 4180 of the electronic circuit system housing 4170 includes a connection protrusion 4171B, a stiffening protrusion 4174, and defines an LED aperture 4181, an aperture 4172, a safety lock actuator groove 4182, and a base actuator groove 4183. The LED aperture 4181 is configured to receive the LEDs 4958A, 4958B such that a user can view the LEDs 4958A, 4958B, which are described in more detail herein.

The connection protrusion 4171B extends from the distal end portion 4180 of the electronic circuit system housing 4170, and is configured to attach the electronic circuit system 4900 to the housing 4110, as described above. The stiffening protrusion 4174 is configured to have at least a portion received within and/or accessible via the aperture 4145 in the housing 4110 (see e.g., FIG. 15). The stiffening protrusion 4174 is configured to limit the bending (e.g., buckling) of the electronic circuit system housing 4170 when the electronic circuit system housing 4170 is coupled to the housing 4110. Moreover, a user can access the stiffening protrusion 4174 via the aperture 4172. In this manner, for example, the user can disengage the stiffening protrusion 4174 from the aperture 4145.

The safety lock actuator groove 4182 of the electronic circuit system housing 4170 is configured to be disposed adjacent the safety lock actuator groove 4123 of the distal end portion 4120 of the housing 4110. In this manner, the safety lock actuator groove 4182 of the electronic circuit system housing 4170 and the safety lock actuator groove 4123 of the distal end portion 4120 of the housing 4110 collectively receive the actuator 4744 of the safety lock 4700, which is described in more detail herein. Similarly, the base actuator groove 4183 of the electronic circuit system housing 4170 is configured to be disposed about the base actuator groove 4124 of the distal end portion 4120 of the housing 4110. The base actuator groove 4183 of the electronic circuit system housing 4170 and the base actuator groove 4124 of the distal end portion 4120 of the housing 4110 collectively receive the actuator 4311 of the base 4302, which is described in more detail herein.

The printed circuit board 4922 of the electronic circuit system 4900 includes a substrate 4924, a first actuation portion 4926 and a second actuation portion 4946. The substrate 4924 of the printed circuit board 4922 includes the electrical components necessary for the electronic circuit system 4900 to operate as desired. For example, the electrical components can be resistors, capacitors, inductors, switches, microcontrollers, microprocessors and/or the like. The printed circuit board may also be constructed of materials other than a flexible substrate such as a FR4 standard board (rigid circuit board).

Figure 34:
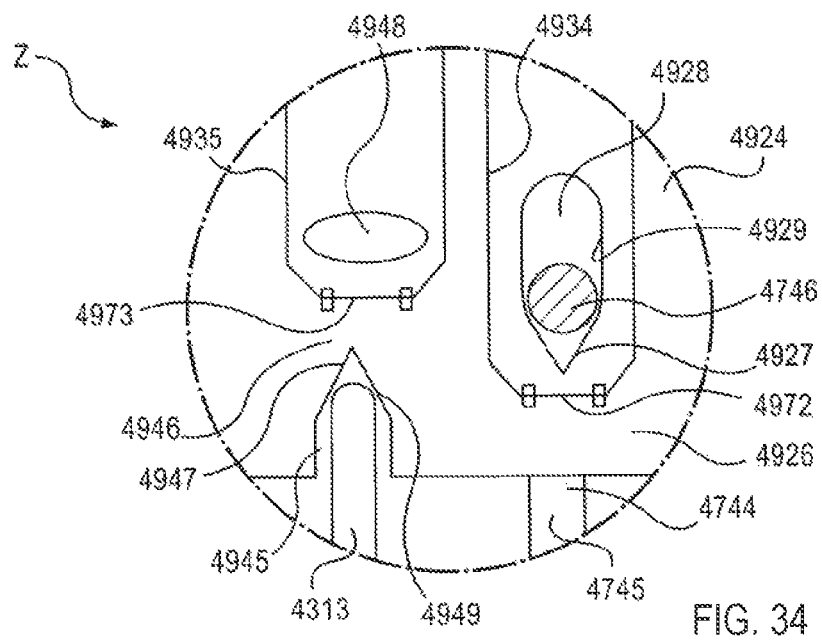
FIGS. 34-36 are front views of a portion of the electronic circuit system of the medical injector labeled as Region Z in FIG. 33 in a first configuration, a second configuration, and a third configuration, respectively.
Figure 36:
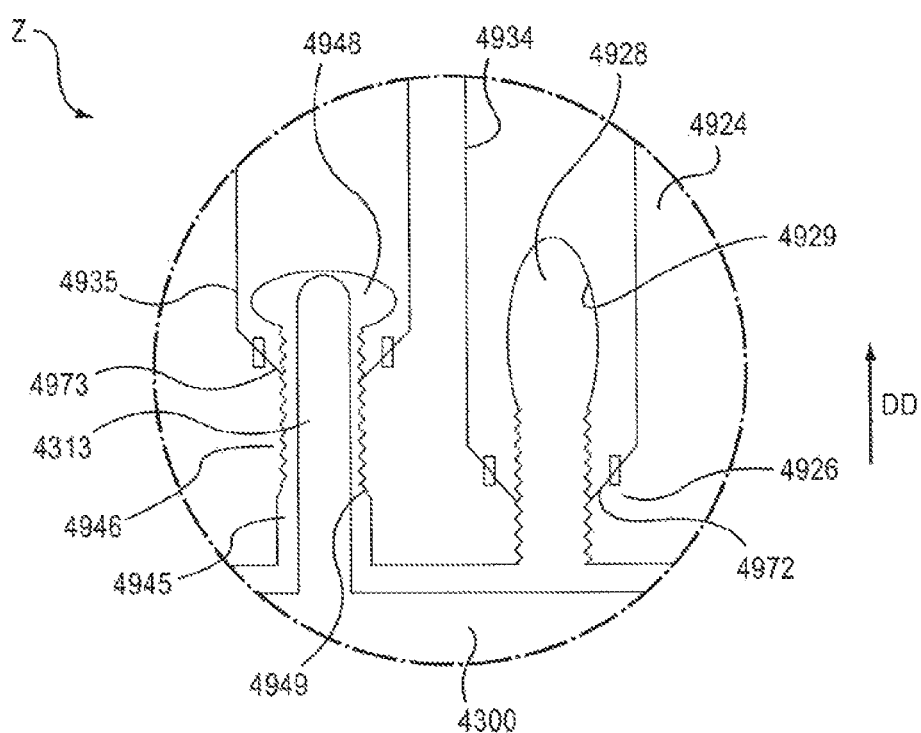

As shown in FIGS. 34-36, the first actuation portion 4926 includes a first electrical conductor 4934 and defines an opening 4928 having a boundary 4929. The opening 4928 of the first actuation portion 4926 is configured to receive a protrusion 4746 of the actuator 4744 of the safety lock 4700. The boundary 4929 of the first opening 4928 has a discontinuous shape, such as, for example, a teardrop shape, that includes a stress concentration riser 4927. The discontinuity and/or the stress concentration riser 4927 of the boundary 4929 can be of any suitable shape to cause the substrate 4924 to deform in a predetermined direction when the protrusion 4746 of the actuator 4744 of the safety lock 4700 is moved relative to the opening 4928, as shown by the arrow CC in FIG. 35.

The opening 4928 is defined adjacent the first electrical conductor 4934 that electronically couples the components included in the electronic circuit system 4900. The first electrical conductor 4934 includes a first switch 4972, which can be, for example a frangible portion of the first electrical conductor 4934. In use, when the safety lock 4700 is moved from a first position (see e.g., FIG. 34) to a second position (see e.g., FIG. 35), the actuator 4744 moves in a direction substantially parallel to a plane defined by a surface of the first actuation portion 4926 of the substrate 4924. The movement of the actuator 4744 causes the protrusion 4746 to move within the first opening 4928, as indicated by the arrow CC in FIG. 35. The movement of the protrusion 4746 tears the first actuation portion 4926 of the substrate 4924, thereby separating the portion of the first electrical conductor 4934 including the first switch 4972. Said another way, when the safety lock 4700 is moved from its first position to its second position (see e.g., FIG. 46), the actuator 4744 moves irreversibly the first switch 4972 from a first state (e.g., a state of electrical continuity) to a second state (e.g., a state of electrical discontinuity). Said yet another way, when the safety lock 4700 is moved from its first position to its second position, the actuator 4744 disrupts the first electrical conductor 4934.

The second actuation portion 4946 includes a second electrical conductor 4935 and defines an opening 4945, having a boundary 4949 and a tear propagation limit aperture 4948. As shown in FIGS. 33-36, the opening 4945 of the second actuation portion 4946 is configured to receive a portion of an actuator 4311 of the base 4302. The boundary 4949 of the opening 4945 has a discontinuous shape that includes a stress concentration riser 4947. The discontinuity and/or the stress concentration riser 4947 of the boundary 4949 can be of any suitable shape to cause the substrate 4924 to deform in a predetermined direction when the actuator 4311 of the base 4302 is moved in a proximal direction relative to the opening 4945, as shown by the arrow DD in FIG. 31.

The second electrical conductor 4935 includes a second switch 4973 disposed between the opening 4945 and the tear propagation limit aperture 4948, which can be, for example, a frangible portion of the second electrical conductor 4935. In use, when the base 4302 is moved from its first position to its second position (see e.g., FIG. 47), the actuator 4311 moves in a proximal direction, substantially parallel to a plane defined by a surface of the second actuation portion 4946 of the substrate 4924. The proximal movement of the actuator 4311 tears the second actuation portion 4946 of the substrate 4924, thereby separating the portion of the second electrical conductor 4935 including the second switch 4973. Said another way, when the base 4302 is moved from its first position to its second position, the actuator 4311 moves irreversibly the second switch 4973 from a first state (e.g., a state of electrical continuity) to a second state (e.g., a state of electrical discontinuity). The tear propagation limit aperture 4948 is configured to limit the propagation of the tear in the substrate 4924 in the proximal direction. Said another way, the tear propagation limit aperture 4948 is configured to ensure that the tear in the substrate 4924 does not extend beyond the tear propagation limit aperture 4948. The tear propagation limit aperture 4948 can be any shape configured to stop the propagation of a tear and/or disruption of the substrate 4924. For example, the tear propagation limit aperture 4948 can be oval shaped. In other embodiments, the proximal boundary of the tear propagation limit aperture 4948 can be reinforced to ensure that the tear in the substrate 4924 does not extend beyond the tear propagation limit aperture 4948.

In some embodiments, the safety lock 4700 and base 4302 can be configured to interact with mechanical and/or optical switches to produce an electronic output in a reversible manner.

The battery assembly 4962 of the electronic circuit system 4900 includes two batteries stacked on top of one another. In other embodiments, the electronic circuit system can include any number of batteries and/or any suitable type of power source. In some embodiments, for example, the battery assembly can include Lithium batteries such as, for example, CR1616, CR2016s, type AAA or the like. The battery assembly 4962 has a first surface 4964 and a second surface 4966. The first surface 4964 of the battery assembly 4962 can contact an electrical contact (not shown) disposed on the substrate 4924. The second surface 4966 of the battery assembly 4962 is configured to contact a contact portion 4918 of a distal end portion 4916 of a battery clip 4910. When both the electrical contact of the substrate 4924 and the contact portion 4918 of the distal end portion 4916 of the battery clip 4910 contact the battery assembly 4962, the batteries of the battery assembly 4962 are placed in electrical communication with the electronic circuit system 4900. Said another way, when the electrical contact of the substrate 4924 and the contact portion 4918 of the distal end portion 4916 of the battery clip 4910 contact the battery assembly 4962, the battery assembly 4962 is configured to supply power to the electronic circuit system 4900.

The battery clip 4910 (shown in FIG. 31) includes a proximal end portion 4912 and a distal end portion 4916. The proximal end portion 4912 defines a retention aperture 4913. The retention aperture 4913 is configured to receive the battery clip protrusion 4173 of the electronic circuit system housing 4170. In this manner, the battery clip protrusion 4173 maintains the position of the battery clip 4910 with respect to the electronic circuit system housing 4170 and/or the battery assembly 4962.

The distal end portion 4916 of the battery clip 4910 includes a contact portion 4918 and an angled portion 4917. As described above, the contact portion 4918 is configured to contact the second surface 4966 of the battery assembly 4962 to place the battery assembly 4962 in electrical communication with the electronic circuit system 4900. The angled portion 4917 of the distal end portion 4916 of the battery clip 4910 is configured to allow a proximal end portion 4236 of a battery isolation protrusion 4235 (see e.g., FIG. 38) to be disposed between the second surface 4966 of the battery assembly 4962 and the contact portion 4918 of the distal end portion 4916 of the battery clip 4910. When the battery isolation protrusion 4235 is disposed between the second surface 4966 of the battery assembly 4962 and the contact portion 4918 of the distal end portion 4916 of the battery clip 4910, the electrical path between the battery assembly 4962 and the remainder of the electrical circuit system 4900 is severed, thereby removing power from the electronic circuit system 4900. The contact portion 4918 of the distal end portion 4916 of the battery clip 4910 is biased such that when the battery isolation protrusion 4235 is removed, the contact portion 4918 will move into contact the second surface 4966 of the battery assembly 4962, thereby restoring electrical communication between the battery assembly 4962 and the electronic circuit system 4900. In some embodiments, the battery isolation protrusion 4235 can be repeatedly removed from between the second surface 4966 of the battery assembly 4962 and the contact portion 4918 of the distal end portion 4916 of the battery clip 4910 and reinserted. Said another way, the battery isolation protrusion 4235 and the battery clip 4910 collectively form a reversible on/off switch.

The audio output device 4956 of the electronic circuit system 4900 is configured to output audible sound to a user in response to a use of the medical injector 4000. In some embodiments, the audible output device 4956 can be a speaker. In some embodiments, the audible sound can be, for example, associated with a recorded message and/or a recorded speech. In other embodiments, the audible instructions can be an audible beep, a series of tones and/or or the like.

In other embodiments, the medical injector 4000 can have a network interface device (not shown) configured to operatively connect the electronic circuit system 4900 to a remote device (not shown) and/or a communications network (not shown). In this manner, the electronic circuit system 4900 can send information to and/or receive information from the remote device. The remote device can be, for example, a remote communications network, a computer, a compliance monitoring device, a cell phone, a personal digital assistant (PDA) or the like. Such an arrangement can be used, for example, to download replacement processor-readable code from a central network to the electronic circuit system 4900. In some embodiments, for example, the electronic circuit system 4900 can download information associated with a medical injector 4000, such as an expiration date, a recall notice, updated use instructions or the like. Similarly, in some embodiments, the electronic circuit system 4900 can upload compliance information associated with the use of the medical injector 4000 via the network interface device.

FIGS. 32 and 33 show the cover 4200 of the medical injector 4000. The cover 4200 includes a proximal end portion 4210 and a distal end portion 4230, and defines a cavity 4242. The cavity 4242 of the cover 4200 is configured to receive at least a portion of the housing 4110. Thus, when the portion of the housing 4110 is disposed within the cover 4200, the cover 4200 blocks an optical pathway between the medicament container 4400 and a region outside of the housing 4110. Similarly stated, when the portion of the housing 4110 is disposed within the cover 4200, the cover 4200 is obstructs the first status indicator aperture 4150 and/or the second status indicator aperture 4151 of the housing 4110 to reduce the amount of light transmitted to the epinephrine composition 4420 within the medicament container 4400. In this manner, the life of the epinephrine composition 4420 can extended by the prevention and/or reduction of degradation to the epinephrine that may be caused by ultra-violet radiation.

The proximal end portion 4210 of the cover 4200 defines apertures 4215 configured to receive the cover retention protrusions 4142 of the housing 4110 (shown in FIGS. 13 and 15). In this manner, the apertures 4215 and the cover retention protrusions 4142 of the housing 4110 removably retain the cover 4200 about at least a portion of the housing 4110. Said another way, the apertures 4215 and the cover retention protrusions 4142 of the housing 4110 are configured such that the cover 4200 can be removed from a portion of the housing 4110 and then replaced about the portion of the housing 4110.

As described above, the electronic circuit system 4900 can be actuated when the housing 4110 is at least partially removed from the cover 4200. More particularly, the distal end portion 4230 of the cover 4200 includes a battery isolation protrusion 4235. The battery isolation protrusion 4235 includes a proximal end portion 4236 and a tapered portion 4237. The proximal end portion 4236 of the battery isolation protrusion 4235 is configured to be removably disposed between the second surface 4966 of the battery assembly 4962 and the contact portion 4918 of the distal end portion 4916 of the battery clip 4910, as described above.

FIGS. 39-42 show the safety lock 4700 of the medical injector 4000. The safety lock 4700 of the medical injector 4000 includes a proximal surface 4740, a distal surface 4760 opposite the proximal surface 4740 and a needle sheath 4720. The safety lock 4700 defines a needle sheath aperture 4770 and a battery isolation protrusion aperture 4775. The battery isolation protrusion aperture 4775 is configured to receive the battery isolation protrusion 4235 of the cover 4200 such that the battery isolation protrusion 4235 can be disposed within the electronic circuit system cavity 4153 or the electronic circuit system 4900, as described above. Similarly stated, the battery isolation protrusion aperture 4775 of the safety lock 4700 is aligned with the battery isolation protrusion aperture 4121 of the housing 4110, such that the battery isolation protrusion 4235 can be disposed within the electronic circuit system cavity 4153 when the cover 4200 is disposed about a portion of the housing 4110.

The proximal surface 4740 of the safety lock 4700 includes a safety lock protrusion 4742, a stopper 4743, an actuator 4744 and two opposing pull tabs 4741. As described above, when the safety lock 4700 is in a first (locked) position, the safety lock protrusion 4742 is configured to be disposed in the opening 4346 defined by the extensions 4343 of the distal end portion 4344 of the release member 4340 (see also FIG. 23). Accordingly, the safety lock protrusion 4742 is configured to prevent the extensions 4343 from moving closer to each other, thereby preventing proximal movement of the release member 4340 of the medicament delivery mechanism 4500 and/or delivery of the epinephrine composition 4420. The stopper 4743 of the safety lock 4700 is a protrusion extending from the proximal surface 4740 of the safety lock 4700. The stopper 4743 is configured to contact a portion of the housing 4110 to limit the proximal movement of the safety lock 4700 relative to the housing 4110. In other embodiments, the stopper 4743 can be any structure configured to limit the proximal movement of the safety lock 4700.

The actuator 4744 of the safety lock 4700 has an elongated portion 4745 and a protrusion 4746. The elongated portion 4745 extends in a proximal direction from the proximal surface 4740. In this manner, the elongated portion 4745 can extend through a safety lock actuator opening 4356 of the base 4302 (see e.g., FIG. 43) and within the safety lock actuator groove 4123 of the housing 4110 and the safety lock actuator groove 4182 of the electronic circuit system housing 4170. The protrusion 4746 extends in a direction substantially transverse to the elongated portion 4745 and/or substantially parallel to the proximal surface 4740 of the safety lock 4700. As described above, the opening 4928 of the first actuation portion 4926 is configured to receive the protrusion 4746 of the actuator 4744 of the safety lock 4700.

The pull tabs 4741 of the safety lock 4700 include a grip portion 4747 and indicia 4748. The grip portion 4747 of the pull tabs 4741 provides an area for the user to grip and/or remove the safety lock 4700 from the rest of the medicament delivery system 4700. The indicia 4748 provides instruction on how to remove the safety lock 4700. In some embodiments, for example, the indicia 4748 can indicate the direction the user should pull the safety lock 4700 to remove the safety lock 4700.

Figure 41:
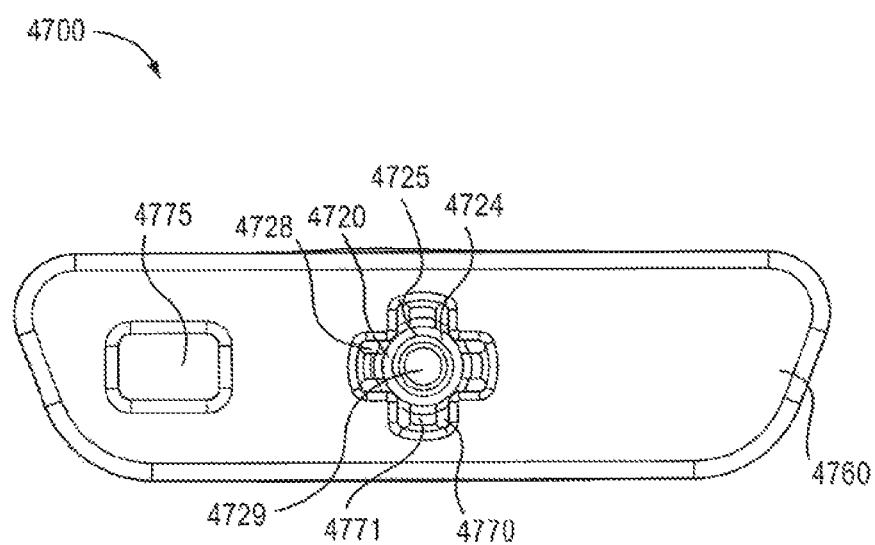
FIG. 41 is a bottom view of the safety lock of the medical injector illustrated in FIG. 39.
Figure 42:
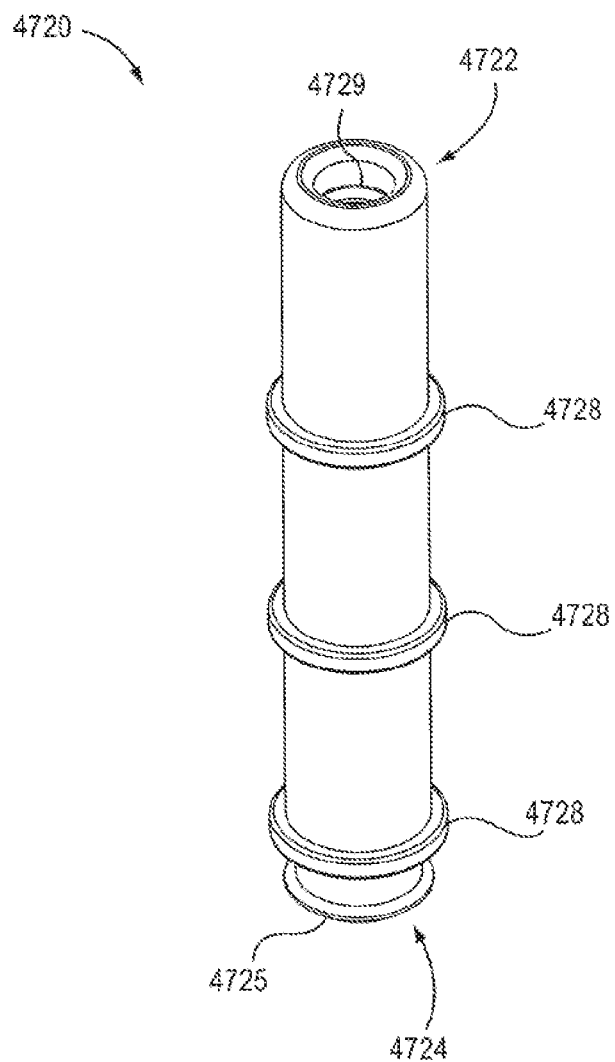
FIG. 42 is a perspective view of a needle sheath of the safety lock of the medical injector illustrated in FIG. 39.

As shown in FIG. 41, the needle sheath 4720 of the safety lock 4700 includes a distal end portion 4724, a proximal end portion 4722 and a plurality of ribs 4728. The needle sheath 4720 can also define a lumen 4729. The lumen 4729 of the safety lock 4700 is configured to receive the needle 4452. In this manner, the needle sheath 4720 can protect the user from the needle 4452 and/or can keep the needle 4452 sterile before the user actuates the medical injector 4000. The proximal end portion 4722 of the needle sheath is configured to contact the distal end portion 4522 of the carrier 4520 of the medicament delivery mechanism 4500.

The distal end portion 4724 of the needle sheath 4720 has an angled ridge 4725. The angled ridge 4725 is configured to allow the proximal end portion 4722 of the needle sheath 4720 to irreversibly move through the needle sheath aperture 4770 of the safety lock 4700 in a distal direction. Said another way, the angled ridge 4725 can be configured in such a way as to allow the proximal end portion 4722 of the needle sheath 4720 to move through the needle sheath aperture 4770 in a distal direction, but not in a proximal direction. The needle sheath aperture 4770 has retaining tabs 4771 configured to engage the proximal end of the angled ridge 4725 when the needle sheath 4720 is moved in a proximal direction. In this manner, the retaining tabs 4771 prevent the proximal movement of the needle sheath with respect to the safety lock 4700. Further, the retaining tabs 4771 are configured to engage the proximal end of the angled ridge 4725 when the safety lock 4700 is moved in a distal direction. Said another way, as shown in FIG. 41, the needle sheath 4720 is removed from the needle 4452 when the safety lock 4700 is moved in a distal direction with respect to the housing 4110.

Figure 43:
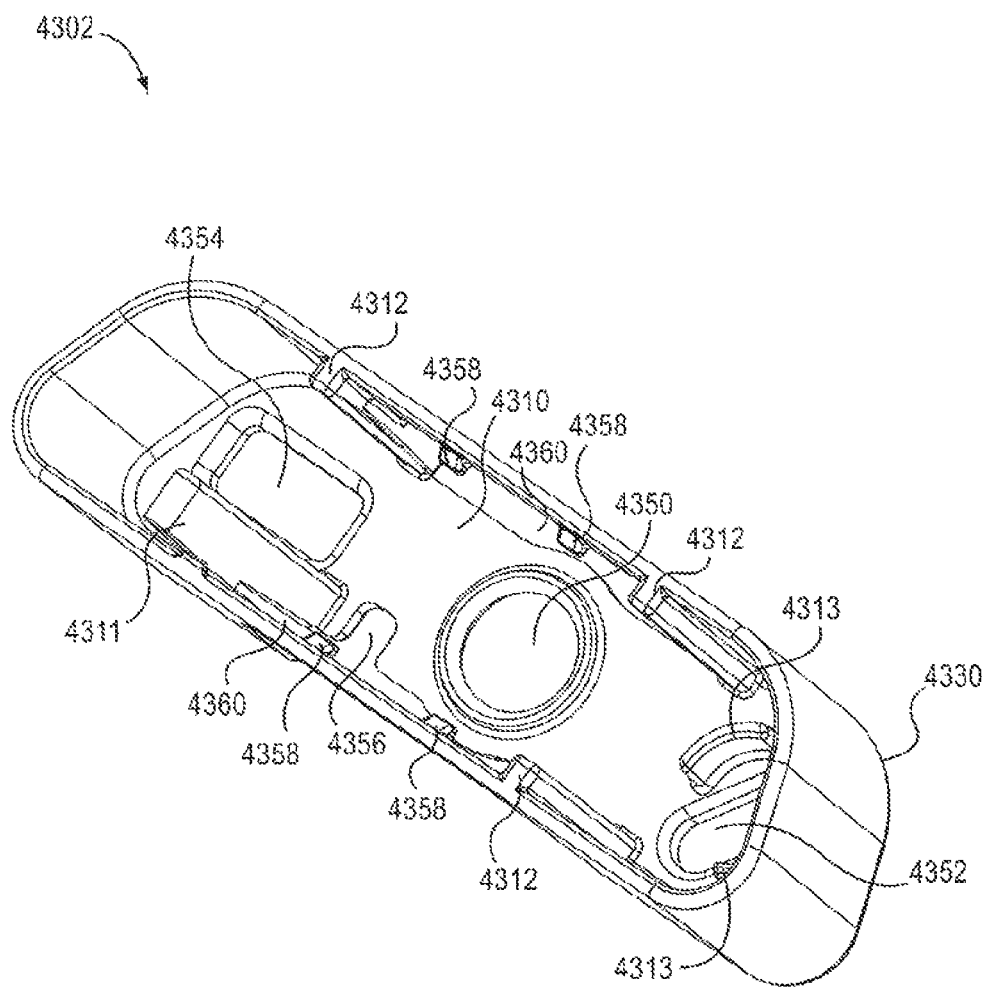
FIG. 43 is a perspective view of a base of the medical injector illustrated in FIG. 12.
Figure 44:
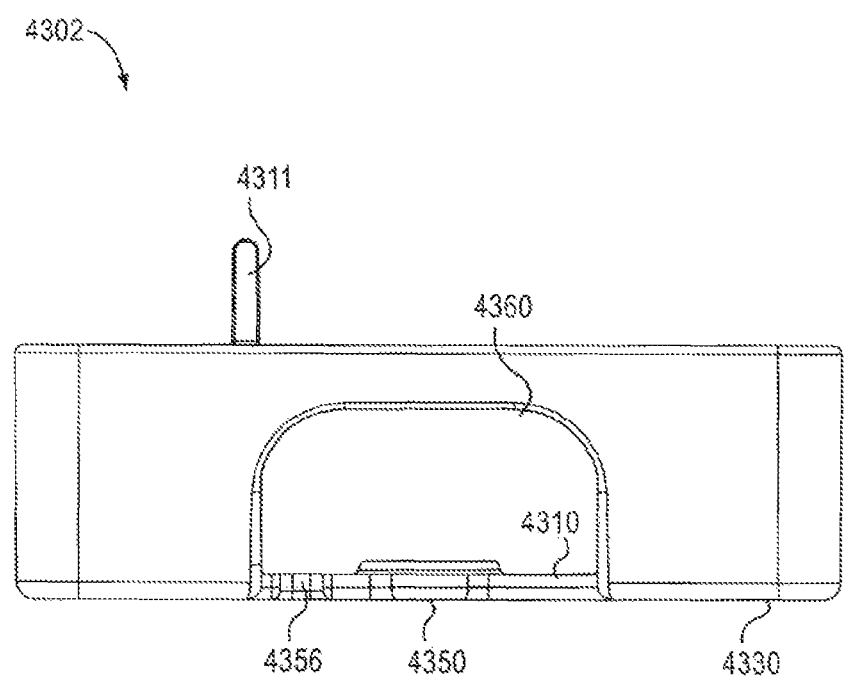
FIG. 44 is a front view of the base of the medical injector illustrated in FIG. 12.

FIGS. 43 and 44 show the base 4302 of the medical injector 4000. The base 4302 includes a proximal surface 4310, a distal contact surface 4330 and base connection knobs 4358. As described above, the distal contact surface 4330 can have an area that, taken in conjunction with the actuation force, produces a pressure against the target location that is within a desired range. In some embodiments, the distal contact surface 4330 can have a contact area between about 322 mm$^2$ (about 0.5 square inches) and about 645 mm$^2$ (about 1 square inch). Such contact area can exclude any openings, cut-outs, or the like. In other embodiments, the contact area can be greater than about 645 mm$^2$ (about 1 square inch). For example, in some embodiments the contact area of any of the contact surfaces described herein (including the contact surfaces 1330, 2330, 3300, 4330) can be between about 645 mm$^2$ (about 1 square inch) and about 968 mm$^2$ (about 1.5 square inches) or between about 645 mm$^2$ (about 1 square inch) and about 1290 mm$^2$ (about 2 square inches).

The base 4302 defines a needle aperture 4350, a safety lock protrusion aperture 4352, a battery isolation protrusion aperture 4354, a safety lock actuator opening 4356, and pull tab openings 4360. The needle aperture 4350 is configured to receive the needle 4452 when the medical injector 4000 is actuated. The safety lock protrusion aperture 4352 of the base 4302 receives the safety lock protrusion 4742 of the safety lock 4700. The battery isolation protrusion aperture 4354 of the base 4302 receives the battery isolation protrusion 4235 of the cover 4200 and the stopper 4743 of the safety lock 4700. The safety lock actuator opening 4356 receives the safety lock actuator 4744 of the safety lock 4700. The pull tab openings 4360 are configured to receive the pull tabs 4741 of the safety lock 4700.

The proximal surface 4310 of the base 4302 includes an actuator 4311, guide members 4312, and protrusions 4313. The actuator 4311 is an elongate member configured to engage the substrate 4924 of the electronic circuit system 4900. As described above, the opening 4945 of the second actuation portion 4946 is configured to receive the actuator 4311 of the base 4302. The guide members 4312 of the base 4302 are configured to engage and/or slide within the base rail grooves 4127 of the housing 4110, as described above. The protrusions 4313 of the base 4302 are configured to engage the tapered surfaces 4349 of the extensions 4343 of the release member 4340. As described in further detail herein, when the safety lock 4700 is removed and the base 4302 is moved in a proximal direction with respect to the housing 4110, the protrusion 4313 of the base 4302 are configured to move the extensions 4343 of the release member 4340 closer to each other, actuating the medicament delivery mechanism 4500.

As described above, the base connection knobs 4358 are configured to engage the base retention recesses 4125A, 4125B in a way that allows proximal movement of the base 4302 but limits distal movement of the base 4302. Moreover, the engagement between the distal base retention recesses 4125A and the base connection knobs 4358 when the base 4302 is in the first position is such that the base 4302 cannot be moved proximally to actuate the device until an actuation force exceeds a minimum value. In this manner, the likelihood of inadvertently actuating the device 4000 is reduced. Moreover, the distal base retention recesses 4125A and the base connection knobs 4358 can be configured such that an upper limit required to move the base 4302 proximally does not exceed an amount that could lead to patient discomfort or excessive compression of the tissue at the target location. For example, in some embodiments, the distal base retention recesses 4125A and the base connection knobs 4358 can be configured such that the force applied by the distal contact surface 4330 to actuate the device 4000 is between about 8.9 N (2 lbf) and about 44.5 N (10 lbf). In other embodiments, the distal base retention recesses 4125A and the base connection knobs 4358 can be configured such that the force applied by the distal contact surface 4330 to actuate the device 4000 is about 26.7 N (6 lbf).

Figure 45:
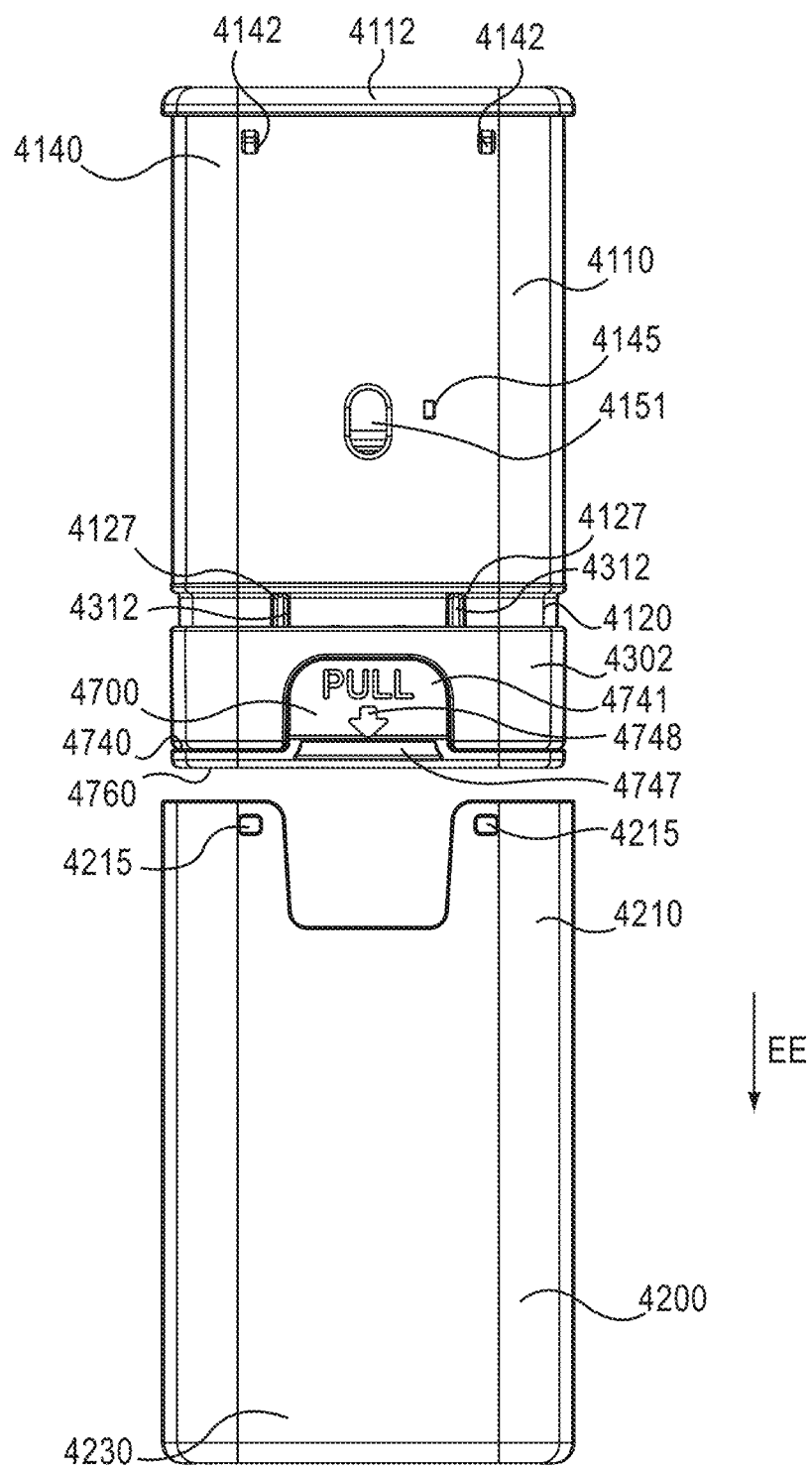
FIG. 45 is a back view of the medical injector illustrated in FIG. 12 in a second configuration.
Figure 46:
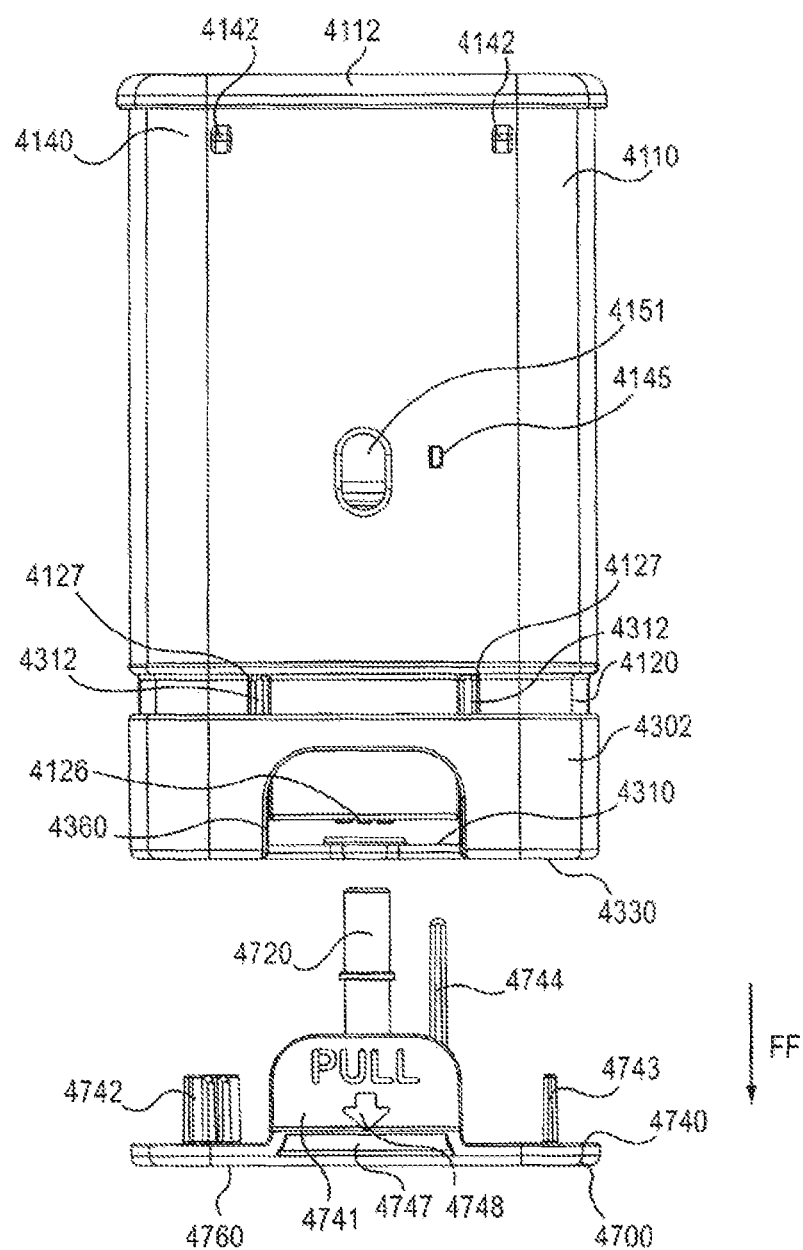
FIG. 46 is a back view of the medical injector illustrated in FIG. 12 in a third configuration.

As shown in FIG. 45, the medical injector 4000 is first enabled by moving the medicament delivery device 4000 from a first configuration to a second configuration by moving the cover 4200 from a first position to a second position. The cover 4200 is moved from the first position to the second position by moving it with respect to the housing 4110 in the direction shown by the arrow EE in FIG. 45. When the cover 4200 is moved with respect to the housing 4110 in the direction EE, the battery isolation protrusion 4235 is removed from the area between the battery clip 4910 and the second surface 4966 of the battery assembly 4962. In this manner, the battery assembly 4962 can be operatively coupled to the electronic circuit system 4900 when the cover 4200 is removed, thereby providing power to the electronic circuit system 4900. Similarly stated, this arrangement allows the electronic circuit system 4900 to be actuated when the cover 4200 is removed.

When power is provided, as described above, the electronic circuit system 4900 can output one or more predetermined electronic outputs. For example, in some embodiments, the electronic circuit system 4900 can output an electronic signal associated with recorded speech to the audible output device 4956. Such an electronic signal can be, for example, associated with a .WAV file that contains a recorded instruction instructing the user in the operation of the medical injector 4000. Such an instruction can state, for example, "remove the safety tab near the base of the auto-injector." The electronic circuit system 4900 can simultaneously output an electronic signal to one and/or both of the LEDs 4958A, 4958B thereby causing one and/or both of the LEDs 4958A, 4958B to flash a particular color. In this manner, the electronic circuit system 4900 can provide both audible and visual instructions to assist the user in the initial operation of the medical injector 4000.

In other embodiments, the electronic circuit system 4900 can output an electronic output associated with a description and/or status of the medical injector 4000 and/or the epinephrine composition 4420 contained therein. For example, in some embodiments, the electronic circuit system 4900 can output an audible message indicating the symptoms for which the epinephrine composition should be administered, the expiration date of the epinephrine composition, the dosage of the epinephrine composition or the like.

As described above, the medical injector 4000 can be can be repeatedly moved between the first configuration and the second configuration when the cover 4200 is moved repeatedly between the first position and the second position respectively. Said another way, the cover 4200 can be removed and replaced about the housing 4110 any number of times. When the cover 4200 is moved from the second position to the first position, the battery isolation protrusion 4235 is inserted between the battery clip 4910 and the second surface 4966 of the battery assembly 4962, deactivating the electronic circuit system 4900. When the cover is moved from the first position to the second position a second time, the electronic circuit system 4900 is once again activated. In this manner, the cover 4200 can be removed and the electronic circuit system 4900 can output an electronic output without compromising the sterility of the needle 4452.

After the cover 4200 is removed from the housing 4110, the medical injector 4000 can be moved from the second configuration to a third configuration by moving the safety lock 4700 from a first position to a second position. The safety lock 4700 is moved from a first position to a second position by moving the safety lock 4700 with respect to the housing 4110 in the direction shown by the arrow FF in FIG. 46. When the safety lock 4700 is moved from the first position to the second position, the safety lock protrusion 4742 is removed from between the extensions 4343 of the release member 4340, thereby enabling the medicament delivery member 4500. Moreover, as shown in FIGS. 34 and 35, when the safety lock 4700 is moved from the housing 4110, the actuator 4744 of the safety lock 4700 moves in the direction CC as shown in FIG. 35, irreversibly moving the first switch 4972 from a first state (e.g., a state of electrical continuity) to a second state (e.g., a state of electrical discontinuity). When the actuator 4744 of the safety lock 4700 moves irreversibly the first switch 4972 of the electronic circuit system 4900 to the second state, the electronic circuit system 4900 can output one or more predetermined electronic outputs. For example, in some embodiments, a processor (not shown) can output an electronic signal associated with recorded speech to the audible output device 4956. Such an electronic signal can be, for example, associated with a recorded message notifying the user of the status of the medical injector 4000. Such a status message can state, for example, "If ready to use the epinephrine auto-injector, pull off the red safety guard." The electronic circuit system 4900 can also simultaneously output an electronic signal to one and/or both of the LEDs 4958A, 4958B, thereby causing one and/or both of the LEDs 4958A, 4958B to stop flashing, change color or the like.

In some embodiments, the first actuation portion 4926 and the actuator 4744 can be configured such that the actuator 4744 must move a predetermined distance before the actuator 4744 engages the boundary 4929 of the opening 4928. For example, in some embodiments, the actuator 4744 must move approximately 0.200 inches before the actuator 4744 engages the boundary 4929 of the opening 4928. In this manner, the safety lock 4700 can be moved slightly without irreversibly moving the first switch 4972 of the electronic circuit system 4900 to the second state. Accordingly, this arrangement will permit the user to inadvertently and/or accidentally move the safety lock 4700 without actuating the electronic circuit system 4900.

In some embodiments, the electronic circuit system 4900 can be configured to output the status message for a predetermined time period, such as, for example, five seconds. After the predetermined time period has elapsed, the electronic circuit system 4900 can output an audible message further instructing the user in the operation of the medical injector 4000. Such an instruction can state, for example, "Place the base of the auto-injector against the patient's thigh. To complete the injection, press the base firmly against the patient's thigh." In some embodiments, the electronic circuit system 4900 can simultaneously output an electronic signal to one and/or both of the LEDs 4958A, 4958B, thereby causing one and/or both of the LEDs 4958A, 4958B to flash a particular color. In this manner, the electronic circuit system 4900 can provide both audible and/or visual instructions to assist the user in the placement and actuation of the medical injector 4000. In some embodiments, the electronic circuit system 4900 can be configured to repeat the instructions after a predetermined time period has elapsed.

As described herein, in other embodiments, the medical injector 4000 can have a network interface device (not shown) configured to operatively connect the electronic circuit system 4900 to a remote device (not shown) and/or a communications network (not shown). In this manner, the electronic circuit system 4900 can send a wireless signal notifying a remote device that the safety lock 4700 of the medical injector 4000 has been removed and that the medical injector 4000 has been armed. In other embodiments, the electronic circuit system 4900 can send a wireless signal (e.g., a wireless 911 call) notifying an emergency responder that the medical injector 4000 has been armed.

After the safety lock 4700 is moved from the first position to the second position, the medical injector 4000 can be moved from the third configuration to a fourth configuration by moving the base 4302 from a first position to a second position. Similarly stated, the medical injector 4000 can be actuated by the system actuator assembly 4300 by moving the base 4302 distally relative to the housing 4110. The base 4302 is moved from its first position to its second position by placing the medical injector 4000 against the body of the patient and moving the base 4302 with respect to the housing 4110 in the direction shown by the arrow GG in FIG. 47. Specifically, the distal contact surface 4330 of the base is placed against a target location of the patient. Moving the base 4302 from the first position to the second position causes the protrusions 4313 on the proximal surface 4310 of the base 4302 to engage the tapered surfaces 4349 of the extensions 4343 of the release member 4340, thereby moving the extensions 4313 together. The inward movement of the extensions 4343 causes the release member 4340 to become disengaged from the distal end portion of the housing 4110, thereby allowing the release member 4340 to be moved proximally along its longitudinal axis as the spring 4370 expands.

Figure 47:
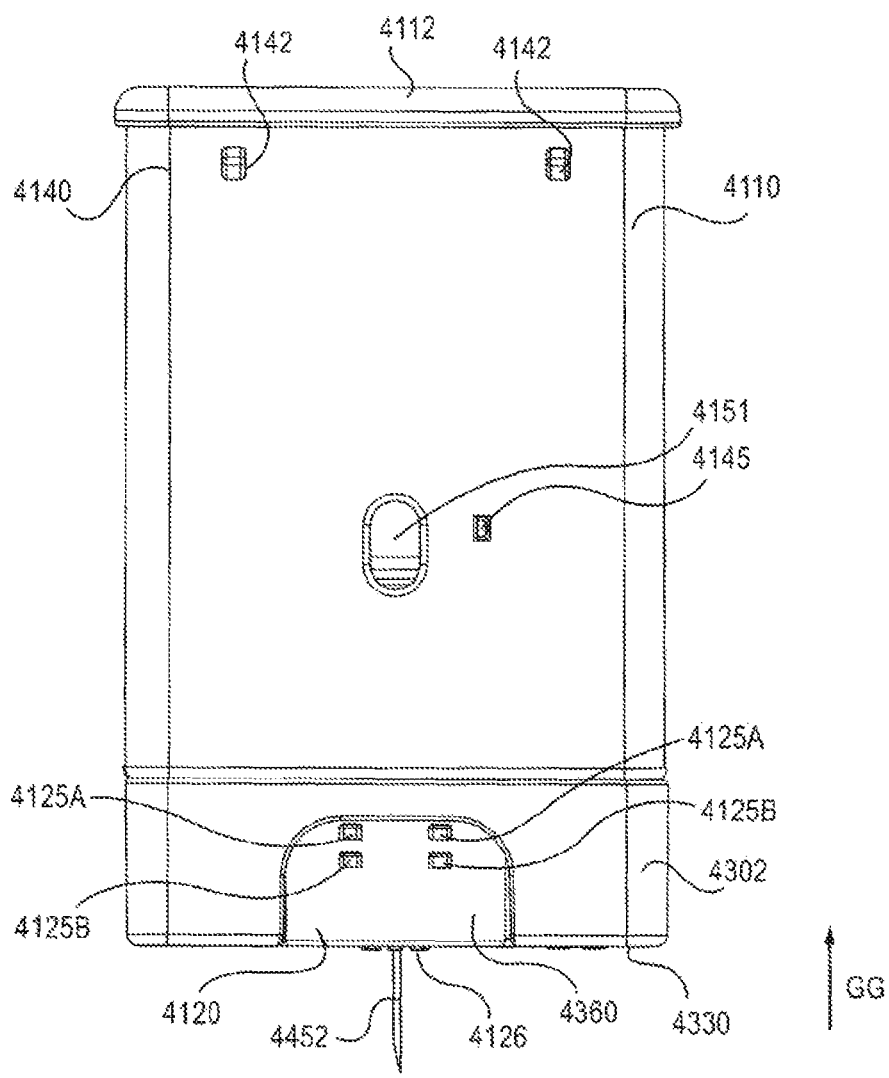
FIG. 47 is a back view of the medical injector illustrated in FIG. 12 in a fourth configuration (i.e., the needle insertion configuration).
Figure 48:
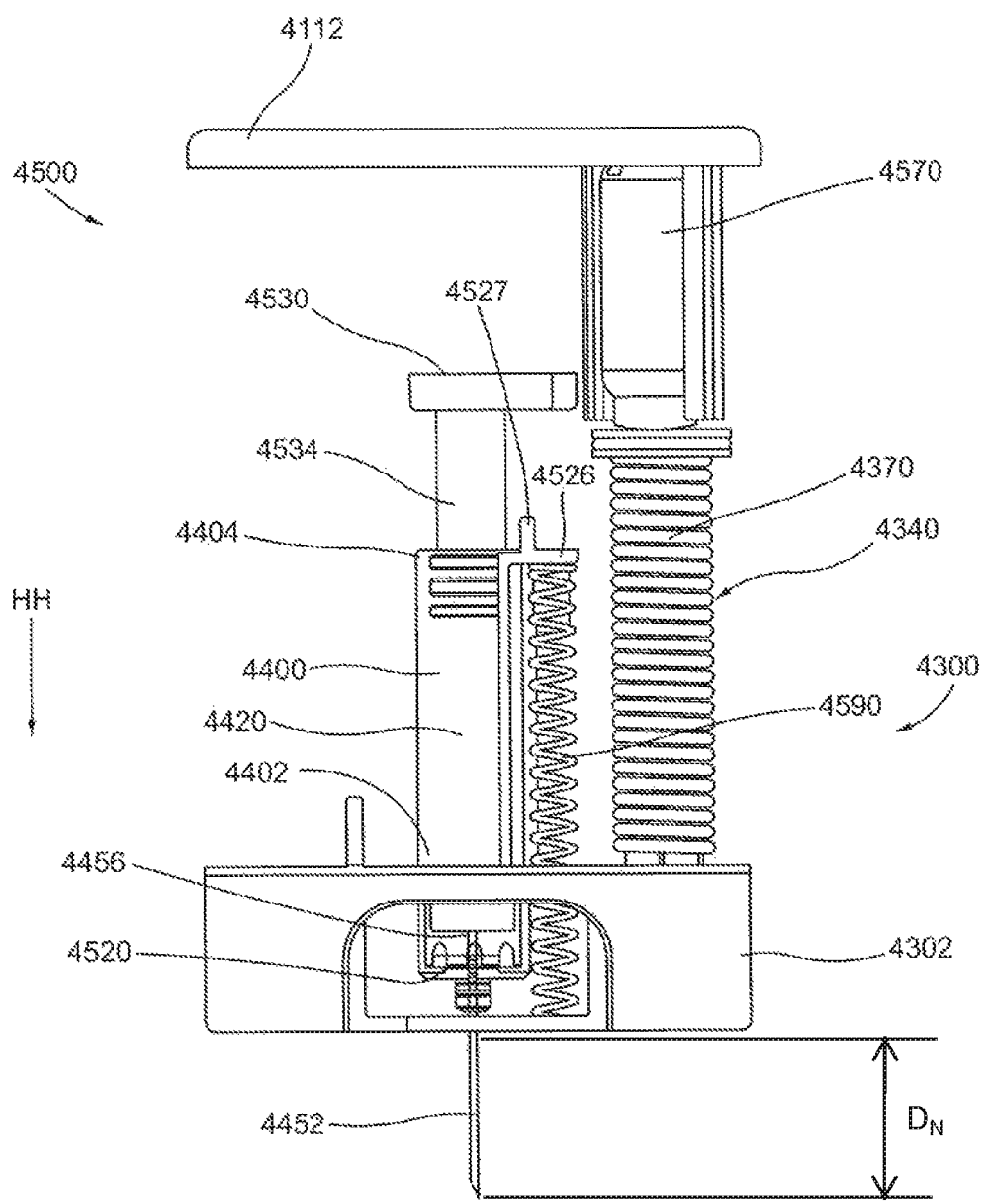
FIG. 48 is a front view of the medical injector illustrated in FIG. 12 in the fourth configuration (i.e., the needle insertion configuration).

When the base 4302 is moved from the first position to the second position, the system actuator 4300 actuates the medicament delivery mechanism 4500, thereby placing the medical injector 4500 in its fourth configuration (i.e., the needle insertion configuration), as shown in FIGS. 47 and 48. More particularly, when the medical injector is in its fourth configuration, the puncturer 4341 of the release member 4340 is in contact with and/or disposed through the frangible seal 4573 of the gas container 4570.

After the frangible seal 4573 has been punctured, an actuating portion of a compressed gas can escape from the gas container 4570 and flow via the gas passageway 4144 into the medicament cavity 4157. The gas applies gas pressure to the movable member 4530 causing the movable member 4530 and the carrier 4520 to move in a distal direction within the medicament cavity 4157, as shown by the arrow HH in FIG. 48. When the carrier 4520 moves distally within the medicament cavity 4157, the carrier 4520 and the medicament container 4400 are in a first configuration. Accordingly, as described above, the medicament container 4400 is connected to the carrier 4520 by a "snap fit" connection. In this manner, the medicament container 4400 and the needle 4452 contemporaneously move with movable member 4530 and/or the carrier 4520 in a distal direction. As described above, the proximal end portion 4456 of the needle 4452 is connected to the distal end portion 4522 of the carrier 4520 and is spaced from the seal 4406 of the medicament container 4400 when the carrier 4520 is in its first configuration. Said another way, the medicament container 4400 and the needle 4452 do not define a medicament delivery path when the carrier 4520 is in the first configuration. The movement of the needle 4452 in a distal direction causes the distal end portion of the needle 4452 to exit the housing 4110 and enter the body of a patient prior to administering the epinephrine composition 4420.

Referring to FIG. 47, the needle 4452 is configured such that the distal tip 4454 extends from the contact surface 4330 by distance $D_N$ sufficient such that the distal tip 1454 is in the muscle layer of the target location. Specifically, in some embodiments, the distance $D_N$ (or effective needle length) is such that the distal tip 4454 will be inserted within the thigh muscle for a patient weighing less than 15 kg, and will have a low likelihood of striking the thigh bone. In this manner, the distance $D_N$ is sufficient to produce an intramuscular delivery of the epinephrine 4420 while also limiting the likelihood of either an intraosseous delivery or a subcutaneous delivery. For example, in some embodiments, the distance $D_N$ is between about 6.35 mm and about 9 mm. In other embodiments, the distance $D_N$ is between about 7 mm and about 8 mm. In yet other embodiments, the distance $D_N$ is about 7.5 mm.

After the carrier 4520 and/or the needle 4452 have moved within the medicament cavity 4157 a predetermined distance, the carrier 4520 and the medicament container 4400 are moved from the first configuration to a second configuration. In the second configuration of the carrier 4520, the medicament container 4400 is released from the "snap-fit" allowing the medicament container 4400 and the movable member 4530 to continue to move in a distal direction relative to the carrier 4520. Said another way, the medicament container 4400 is configured to slidably move within the carrier 4520 when the carrier is moved from the first configuration to the second configuration. As the medicament container 4400 continues to move within the carrier 4520, the proximal end portion 4456 of the needle 4452 contacts and punctures the seal 4406 of the medicament container 4400. This allows the medicament contained in the medicament container 4400 to flow into the lumen (not shown) defined by the needle 4452, thereby defining a medicament delivery path.

After the medicament container 4400 contacts the distal end of the carrier 4520, the medicament container 4400 stops moving within the carrier 4520 while the movable member 4530 continues to move in a distal direction, as shown by the arrow II in FIG. 49. This causes the piston portion 4534 of the movable member 4530 to move within the medicament container 4400 containing the epinephrine composition 4420. As the piston portion 4534 of the movable member 4530 moves within the medicament container 4400, the piston portion 4534 contacts the elastomeric member 4410 and generates a pressure upon the epinephrine composition 4420 contained within the medicament container 4400, thereby allowing at least a portion of the epinephrine composition 4420 to flow out of the medicament container 4400 and into the lumen defined by the needle 4452. The medicament is delivered to a body of a user via the medicament delivery path defined by the medicament container 4400 and the needle 4452.

Figure 50:
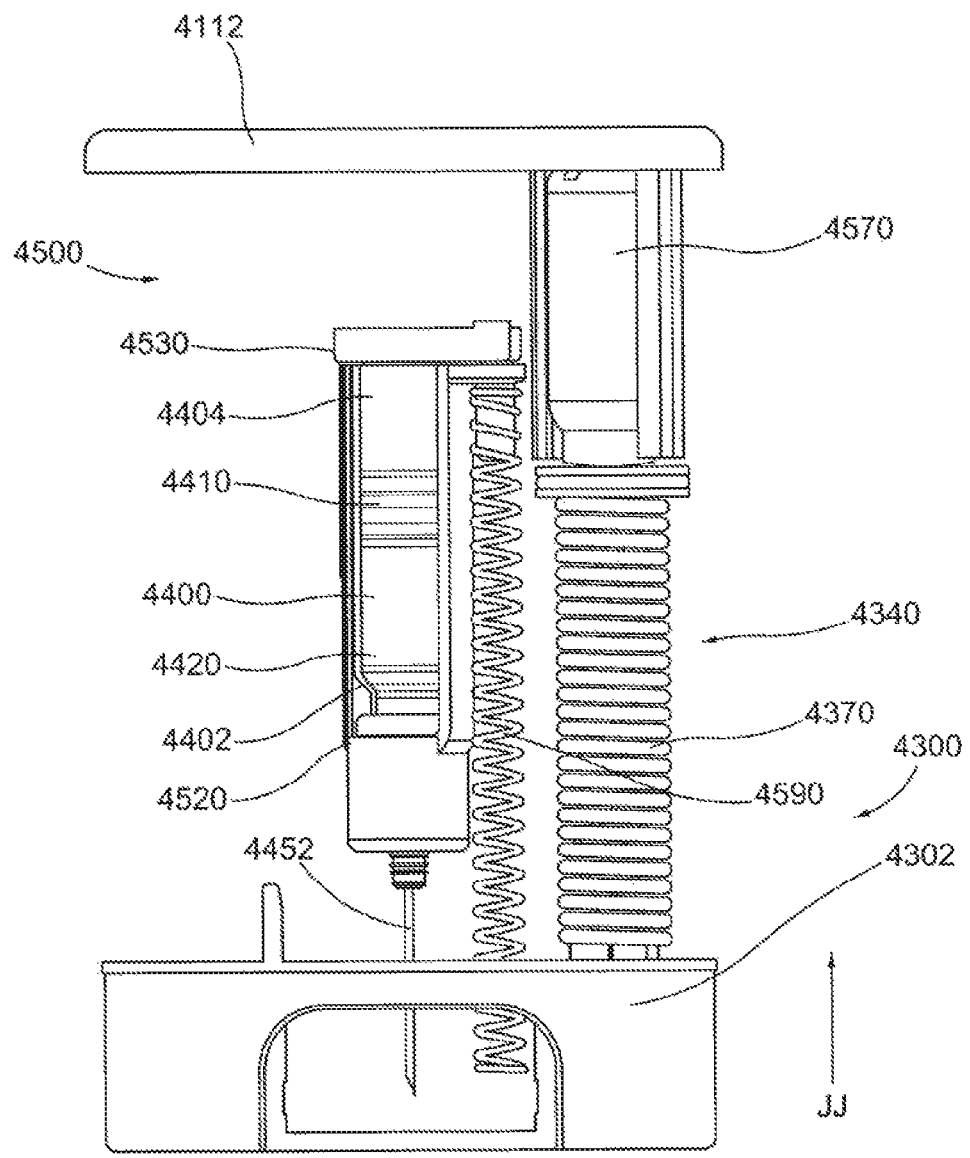
FIG. 50 is a front view of the medical injector illustrated in FIG. 12 in a sixth configuration (i.e., the retraction configuration).
Figure 53:
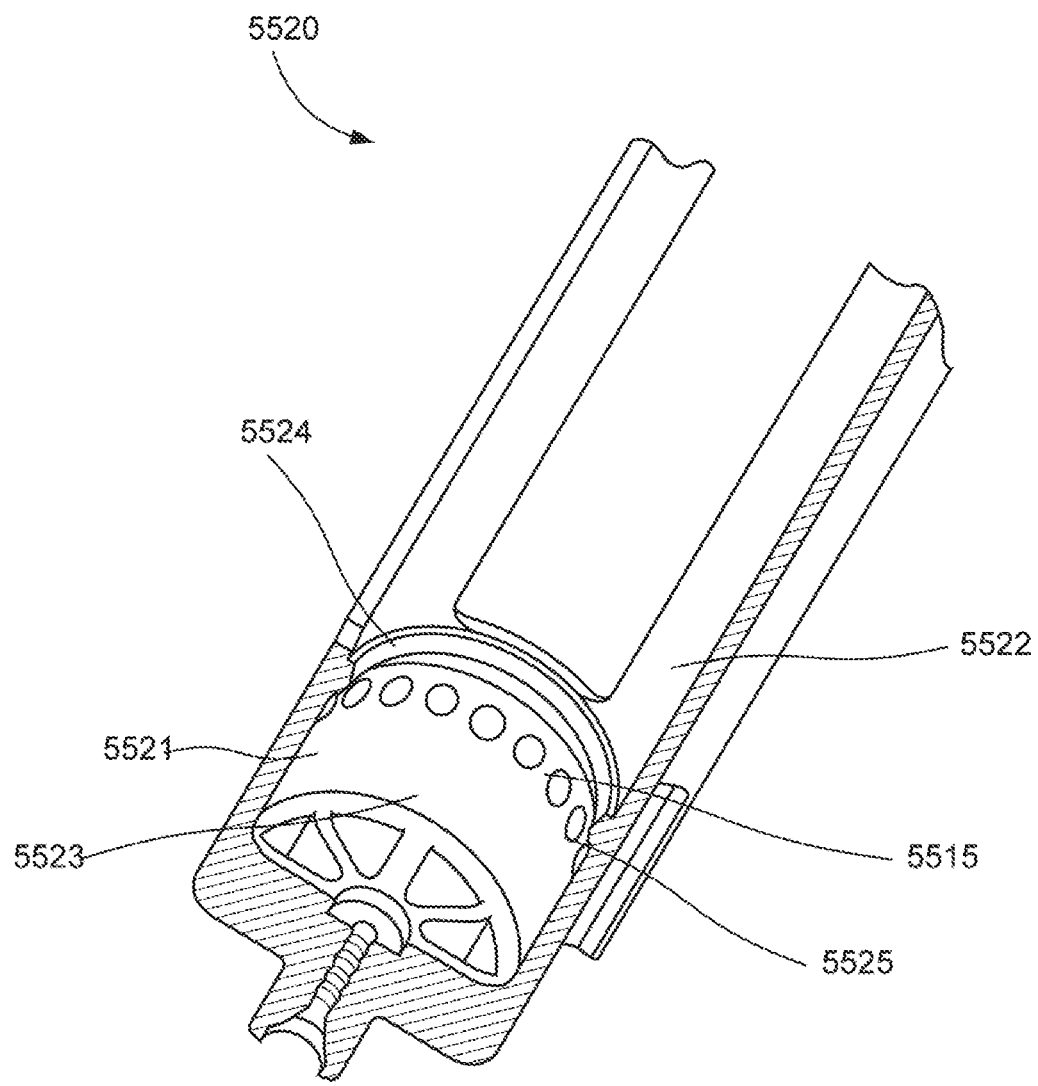
FIG. 53 is a perspective cross-sectional view of a carrier of a medical injector according to an embodiment.
Figure 55:
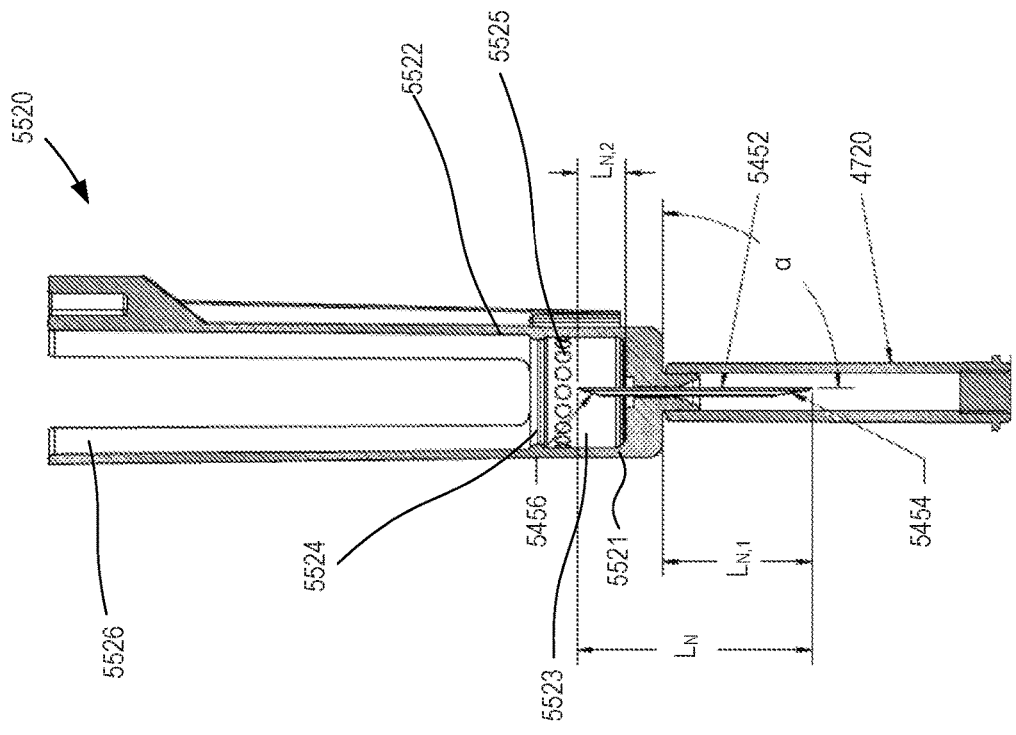
FIG. 55 is a cross-sectional view of the carrier assembly shown in FIG. 54 taken along the line A-A in FIG. 54.
Figure 54:
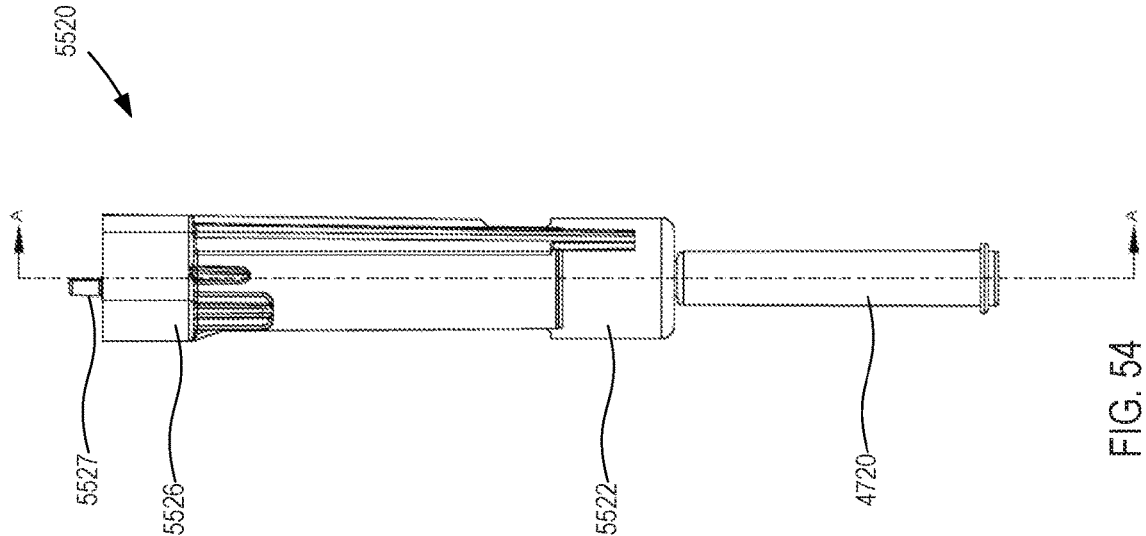
FIG. 54 is side view of a carrier assembly, including the carrier shown in FIG. 53 and the needle shown in FIGS. 51 and 52.
Figure 56:
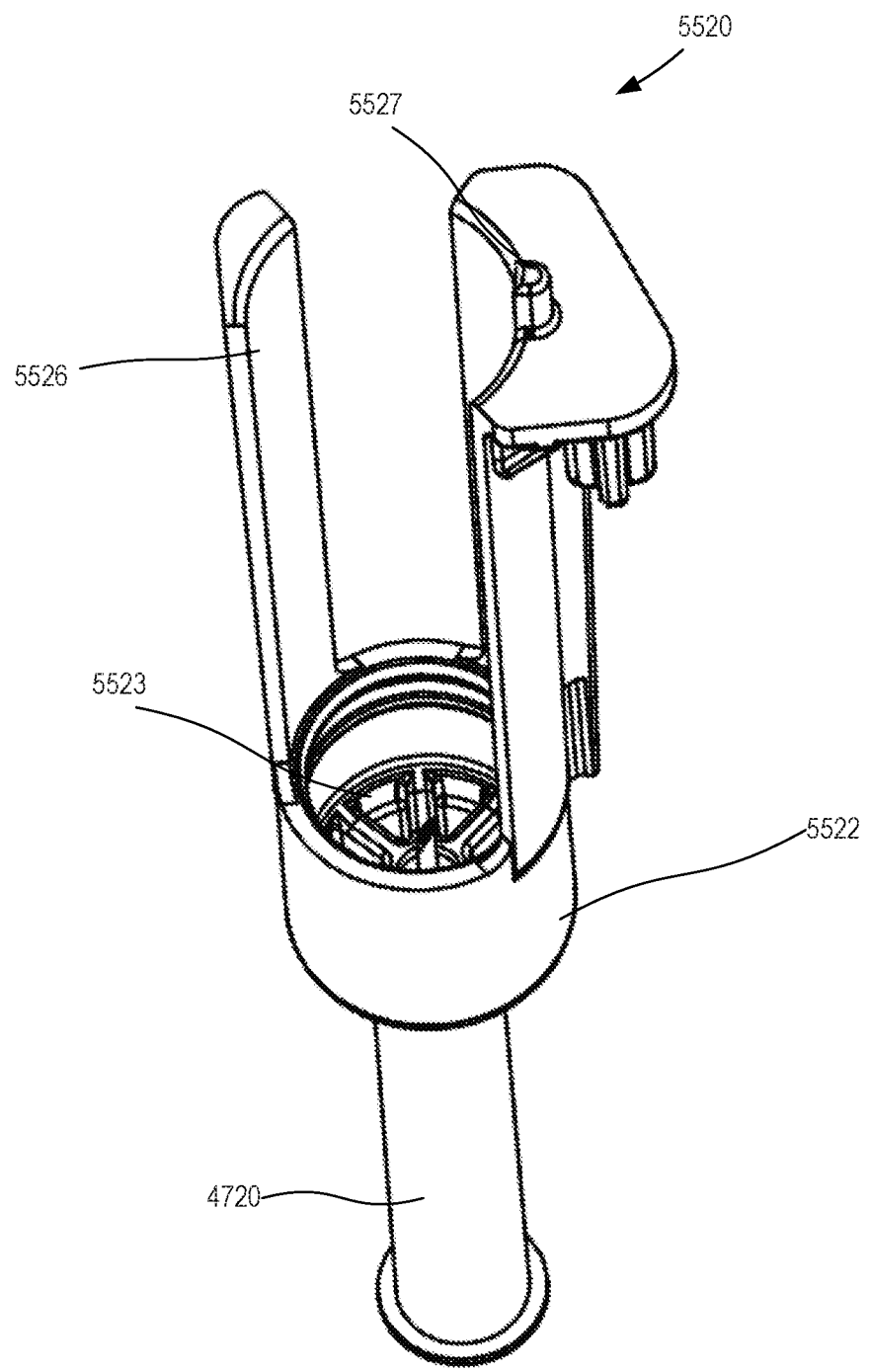
FIG. 56 is a perspective view of the carrier assembly shown in FIG. 54.

As shown in FIG. 50, after the movable member 4530 moves a predetermined distance within the medicament container 4400 (i.e., a distance that corresponds to the desired volumetric dose), the gas valve actuator 4527 of the carrier 4520 engages the gas relief valve (not shown in FIG. 50) of the movable member 4530 thereby allowing the pressurized gas contained within the gas chamber (i.e., the volume within the medicament cavity 4157 between the proximal end of the housing 4110 and the proximal end of the movable member 5530) to escape. Similarly stated, the gas valve actuator 4527 of the carrier 4520 engages the gas relief valve of the movable member 4530, the pressure within the housing 4110 is reduced, thereby ending the injection event. In this manner, the pre-injection distance between the proximal end portion of the movable member 4530 and the gas valve actuator 4527 of the carrier 4520 can be adjusted to control the amount of the epinephrine composition 4420 to be injected. After the gas pressure within the medicament cavity 4157 decreases below a certain level, the force exerted by the retraction spring 4590 on the carrier 4520 can be sufficient to cause the carrier 4520 to move proximally within the housing 4110 (i.e., to retract), as shown by the arrow JJ in FIG. 50.

As described above, the actuator 4311 of the base 4302 actuates the electronic circuit 4900 to trigger a predetermined output or sequence of outputs when the base 4302 is moved from its first position to its second position (see, e.g., FIGS. 32-36). When the actuator 4311 is moved in a proximal direction relative to the opening 4945, as shown by the arrow DD in FIG. 36, the electronic circuit system 4900 is actuated to output one or more predetermined electronic outputs. For example, in some embodiments, the electronic circuit system 4900 can output an electronic signal associated with recorded speech to the audible output device 4956. Such an electronic signal can be, for example, associated with an audible countdown timer, instructing the user on the duration of the injection procedure. Said another way, if it takes, for example, ten seconds to complete an injection, an audible countdown timer can count from ten to zero ensuring that the user maintains the medical injector 4000 in place for the full ten seconds. In other embodiments, the electronic signal can be, for example, associated with a recorded message notifying the user that the injection is complete, instructing the user on post-injection disposal and safety procedures, instructing the user on post-injection medical treatment or the like. Such a status message can state, for example, "The injection is now complete. Please seek further medical attention from a doctor." The electronic circuit system 4900 can also simultaneously output an electronic signal to one and/or both LEDs 4958A, 4958B, thereby causing one and/or both LEDs 4958A, 4958B to stop flashing, change color or the like, to provide a visual indication that the injection is complete. In other embodiments, the electronic circuit system 4900 can send a wireless signal notifying a remote device that the injection is complete. In this manner, a patient's compliance can be monitored.

In some embodiments, the second actuation portion 4946 and the actuator 4311 can be configured such that the base 4500 and/or the actuator 4311 must move a predetermined distance before the actuator 4311 engages the boundary 4949 of the opening 4945. For example, in some embodiments, the actuator 4311 must move approximately 0.200 inches before the actuator 4311 engages the boundary 4949 of the opening 4945. In this manner, the base 4700 can be moved slightly without irreversibly moving the second switch 4973 of the electronic circuit system 4900 to the second state. Accordingly, this arrangement will permit the user to inadvertently and/or accidentally move the base 4500 without actuating the electronic circuit system 4900.

Although the electronic circuit system 4900 is shown and described above as having two irreversible switches (e.g., switch 4972 and switch 4973), in other embodiments, an electronic circuit system can have any number of switches. Moreover, such switches can be either reversible or irreversible.

In some embodiments an auto-injector drug product, such as the medical injector 4000, can include a medicament container containing a dose of epinephrine effective for administration to a patient experiencing anaphylaxis and having a weight of less than 15 kg. Specifically, the auto-injector drug product can be configured to deliver 0.1 mL of epinephrine solution, of the types described herein. Moreover, in such embodiments, the components of the auto-injector drug product are configured such that the delivered dose is within a tolerance (or accuracy) of ±15 percent of the nominal value (i.e., 0.1 mL). Said another way, in such embodiments, the components of the auto-injector drug product are configured such that the delivered dose is between 0.085 mL and 0.115 mL.

As described above, the repeatability and tolerance of the volume delivered is a function of the stroke length of the movable member (e.g., the movable member 4530 or any other device that acts to move the elastomeric member within the medicament container), which, in turn, is controlled by the release of the gas (in gas-powered devices), an end stop mechanism (e.g., to mechanically limit the stroke length), or the like. Accordingly, in some embodiments, the carrier 4520 (or any other carriers described herein) and the gas valve actuator 4527 (or any other gas valve actuators described herein) can have a length and a tolerance that accommodates and/or produces the desired volumetric accuracy.

Moreover, in some embodiments, a needle can have an overall length, and can be coupled within the carrier (e.g., the carrier 4520) in a manner such that the proximal tip of the needle repeatably pierces the seal (e.g., the seal 4406) at the distal end of the medicament container. For example, FIGS. 51-60 show various views of a needle 5452 and a carrier 5520 according to an embodiment. The needle 5452 and the carrier 5520 can be included within any of the medicament delivery devices, auto-injectors and/or drug products disclosed herein. As described below, the needle 5452 and the carrier 5520 are configured such that, in use, the proximal tip 5456 of the needle 5452 is repeatedly and accurately placed into fluid communication with the medicament container 4400 (see FIGS. 57-60). Moreover, the carrier 5520 is configured to reduce any air pressure that can be retained beneath the distal end of the medicament container 4400 during the movement of the medicament container 4400 within the carrier 5520, and which can lead to undesirable variability in the amount of the epinephrine solution delivered. Finally, the needle 5452 and the carrier 5520 are configured such that the distance that the distal tip 5454 extends from the base (not shown) is appropriate for insertion into the thigh muscle for a patient weighing less than 15 kg (and more specifically between about 7.5 kg and about 15 kg). Specifically, the needle 5452 and the carrier 5520 are configured such that the effective needle length (identified as $D_N$ above) is between about 6.35 mm and about 9 mm. In other embodiments, the distance effective needle length is between about 7 mm and about 8 mm. In yet other embodiments, the distance effective needle length is about 7.5 mm. In this manner, a drug product that includes the carrier 5520 and the needle 5452, and that has a dose of epinephrine effective for administration to a patient weighing less than 15 kg, will repeatably and accurately deliver the dose in a manner that such delivery will be within a volumetric tolerance of ±15 percent, have a high likelihood of being an intramuscular delivery, and will have a low likelihood of being an intraosseous delivery.

Referring to FIGS. 51 and 52, the needle 5452 includes a proximal end tip 5456 and a distal end tip 5454. The needle 5452 is coupled within the distal end portion 5522 of the carrier 5520 (see FIG. 55) such that the proximal end tip 5456 can be selectively inserted into the medicament container 4400, as described below. The needle 5452, as well as any other needles shown and described herein, can have any diameter and/or length to facilitate the injection of a medicament (e.g., the epinephrine composition 4420) according to the methods described herein. For example, the needle 5452 can have an overall length $L_N$ that is sufficient to provide the desired length $L_{N,2}$ of the proximal end tip 5456 within the coupling volume 5523 of the carrier 5520 and the desired length $L_{N,1}$ of the distal end tip 5454 extending from the bottom surface of the carrier 5520. For example, the needle 5452 can have a length ($L_N$, $L_{N,1}$) suitable to penetrate clothing and deliver the epinephrine via a subcutaneous injection and/or an intramuscular injection. In some embodiments, the needle 5452 (and any needle disclosed herein) can have a length such that, in use, the distal tip 5454 extends from the contact surface of the device (e.g., the contact surface 4330) by distance sufficient such that the distal tip 5454 is in the muscle layer of the target location. Specifically, in some embodiments, the distance that the distal tip 5454 extends (referred to herein as $D_N$ or the effective needle length) is such that the distal tip 5454 will be inserted within the thigh muscle for a patient weighing less than 15 kg (more specifically, between about 7.5 kg and about 15 kg), and will have a low likelihood of striking the thigh bone. In this manner, the drug product including the carrier 5520 and the needle 5452 are configured to produce an intramuscular delivery of a dose of epinephrine while also limiting the likelihood of either an intraosseous delivery or a subcutaneous delivery. For example, in some embodiments, the distance that the distal tip 5454 extends from the contact surface is between about 6.35 mm and about 9 mm. In other embodiments, such distance is between about 7 mm and about 8 mm. In yet other embodiments, such distance is about 7.5 mm.

To accommodate the desired effective needle length, in some embodiments, the overall length $L_N$ of the needle 5452 can be 17.52 mm±0.78 mm. In some embodiments, the needle can be coupled to the distal end portion 5522 of the carrier 5520 such that the length $L_{N,2}$ is 3.6 mm and the length $L_{N,1}$ is 11.17 mm.

The needle 5452 defines a lumen that can be selectively placed in fluid communication with the medicament container 4400 (or any other medicament containers described herein) to define a medicament delivery path through which the epinephrine composition can flow. The needle 51452 can be any gauge (e.g., 18 gauge, 23 gauge, 24 gauge, 25 gauge, 27 gauge, 32 gauge, etc.). The distal end tip 5454 can have any suitable bevel or shape. For example, in some embodiments, the distal end tip 5454 can include an overall bevel length of about 3.2 mm, a primary bevel angle of about 9.75 degrees, and a secondary bevel angle of about 18.5 degrees. The proximal end tip 5456 can also have any suitable bevel or shape. For example, in some embodiments, the proximal end tip 5456 can include an overall bevel length of about 2.0 mm, a primary bevel angle of about 17 degrees, and a secondary bevel angle of about 25 degrees.

Referring to FIGS. 53-56, the carrier 5520 includes a distal end portion 5522 and a proximal end portion 5526. The carrier 5520 can be used in any of the medicament delivery devices, auto-injectors or drug products described herein, include the drug product 4400. The proximal end portion 5526 of the carrier 5520 includes a gas valve actuator 5527. As described above with reference to the actuator 4527, the gas valve actuator 5527 is configured to engage a gas relief valve of a movable member (e.g., the movable member 4530) to allow the pressurized gas contained within the gas chamber to escape when the injection event is complete. As described above, the length of the carrier 5520 and/or the gas valve actuator 5527 can determine the point along the travel of the movable member at which the gas relief valve is actuated. In this manner, the length of the carrier 5520 and/or the gas valve actuator 5527 can determine the "stroke" of the movable member, and therefore, the volume of epinephrine delivered.

The distal end portion 5522 of the carrier 5520 includes a side wall 5521 that defines a coupling volume 5523. As shown in FIGS. 57-60, the distal end portion of the medicament container 4400 (or any other medicament container described herein) is coupled to the carrier 5520 within the coupling volume 5523. As described above, the medicament container 4400 can move relative to the carrier 5520 between a first configuration (FIGS. 57-58) and a second configuration (FIGS. 59-60) during an injection event. When in the first configuration, the proximal end portion 5456 of the needle 5452 is spaced apart from the septum 4407 of the medicament container 4400. This allows the needle insertion operation to be completed while the needle 5452 is fluidically isolated from the medicament container 4400. As shown, the side wall 5521 includes a first annular protrusion 5524 and a second annular protrusion 5525 (or retention portion). When the medicament container 4400 is in the first configuration (FIGS. 57-58), the first annular protrusion 5524 and the crimp seal 4406 produce a sterile seal that limits the passage of microbial particles therethrough. In this manner, the coupling volume 5523 (which contains the proximal end tip 5456 of the needle 5452) is maintained in a sterile environment. The second annular protrusion 5525 (or retention portion) includes a series of protrusions that retain the distal end of the medicament container 4400 in the first configuration. Specifically, the retention portion 5525 is sized to resist distal movement of the medicament container against the preload of the retraction spring (e.g., spring 4590), which exerts an upward force on the carrier 4520. As shown, the retention portion 5525 defines a series of passageways 5515.

In use, after the needle insertion operation, the continued distal force applied to the elastomeric member (not shown) exceeds a threshold amount such the carrier 5520 and the medicament container 4400 are moved to the second configuration. Said another way, the force releases the medicament container 4400 releases from the "snap-fit" produced by the retention portion 5525, causing the medicament container 5400 to move distally within the coupling volume 5523. As a result, the proximal end portion 5456 of the needle 5452 pierces the septum 4407. In this manner, the needle 5452 can be selectively placed in fluid communication with the medicament container 4400 to define a medicament delivery path (not shown).

When the medicament container 4400 is moved downward within the coupling volume 5523, the passageways 5515 defined by the retention portion 5525 allow air within the coupling volume 5523 to escape. This has been shown to improve the accuracy of the delivered dose by reducing air pressure within the coupling volume 5523. Specifically, allowing any trapped air pressure within the coupling volume 5523 to escape limits the likelihood that the pressure/trapped air will flow into the medicament container via the septum 4407, thereby disrupting the accuracy of the dosage. Although the retention portion 5525 is shown as defining a series of passageways 5515, in other embodiments, the retention portion 5525 can provide any suitable passageway or "bleed" mechanism.

Although the medical injector 4000 and the carrier 5520 are shown and described above as including a cartridge-type medicament container, in other embodiments, an infant-dose medical injector can include any suitable medicament container. For example, in some embodiments, the medical injector (or any of the medical injectors described herein) can include a prefilled syringe assembly. By including the dose of epinephrine within a prefilled syringe assembly, the medical injector can employ the cost-effective fill-finish solution provided by prefilled syringes. Such medical injectors can include any of the prefilled syringe injectors shown and described in U.S. Pat. No. 9,084,849 entitled "Medicament Delivery Devices for Administration of a Medicament within a Prefilled Syringe," or in International Patent Publication No. WO2017/004345, entitled "Auto-Injectors for Administration of a Medicament within a Prefilled Syringe," each of which is incorporated herein by reference in its entirety.

Figure 61:
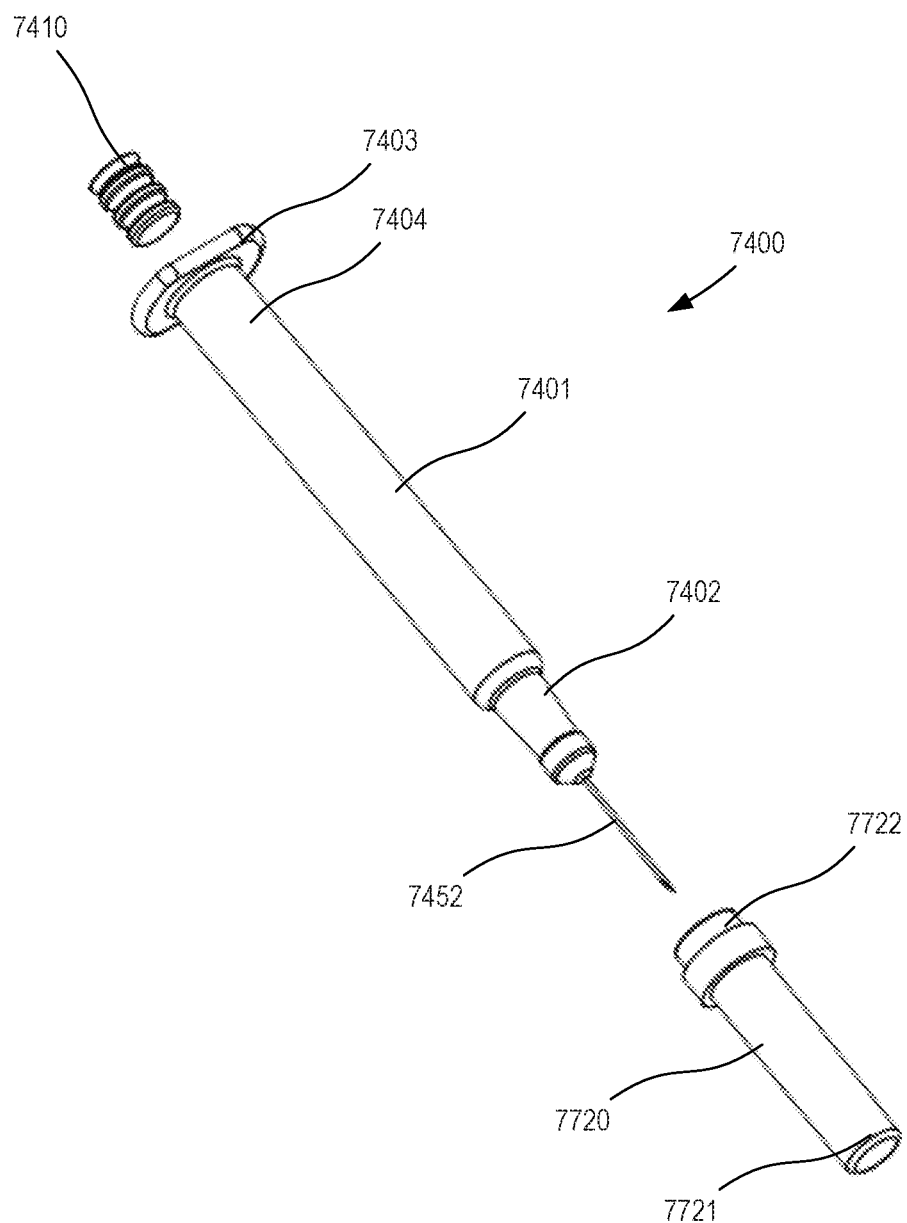
FIG. 61 is an exploded view of a prefilled syringe assembly that can be used within a medical injector according to an embodiment.
Figure 62:
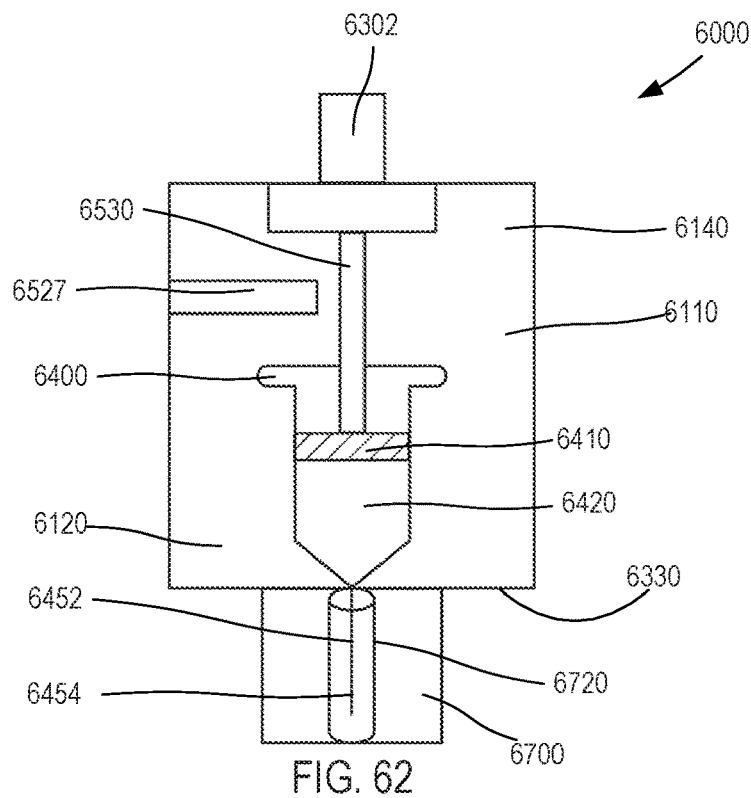
FIGS. 62-65 are schematic illustrations of a medicament delivery device according to an embodiment, in a first configuration, second configuration, third configuration, and fourth configuration, respectively.

For example, any of the medical injectors, including the medical injectors 4000, 4000', and 6000, can include a prefilled syringe 7400 as shown in FIG. 61. The prefilled syringe 7400 (also referred to as a medicament container assembly) includes a container body 7401, an elastomeric member 7410, a needle 7452 and a needle sheath 7720. The container body 7401 has a distal end portion 7402 and a proximal end portion 7404. The container body 7401 defines a volume that contains (i.e., is filled with or partially filled with) a medicament (e.g., a dose of epinephrine, of the composition and the amounts described herein). The distal end portion 7402 of the medicament container assembly 4200 includes a neck that is coupled to the needle 7452. More particularly, the needle 7452 is staked to the distal end portion 7402 (i.e., the needle 7452 is fixedly coupled to the container body 7401 during manufacturing, and is not coupled to the container body 7401 by fitting or removable connector). In this manner, the needle 7452 is in fluid communication with the container body 7401. The proximal end portion 7404 of the container body 7401 includes a flange 7403, which can be supported (or disposed within) a carrier (e.g., similar to the carrier 4520 shown above), a holder or a container interface. The flange 7403 can be of any suitable size and/or shape. Although shown as substantially circumscribing the container body 7401, in other embodiments, the flange 7403 can only partially circumscribe the container body 7401.

The elastomeric member 7410 is disposed within and seals the medicament within the container body 7401. The elastomeric member 7410 is configured to move within the container body 7401 to inject the medicament from the medicament container assembly 7400. For example, in some embodiments, the elastomeric member 7410 can be moved within the container body 7401 by a movable member or plunger, similar to the movable member 4530 described herein. The movable member can, in turn, be moved by any suitable means. For example, in some embodiments, a medical injector can include an energy storage member, such a spring or a compressed gas container (e.g., compressed gas container 4570) that produces a force to move the movable member. In other embodiments, the medical injector can include an actuator that transfers a manual force produced by a user's hand to move the movable member, and thus the elastomeric member 7410.

The elastomeric member 7410 can be of any design or formulation suitable for contact with the medicament. For example, the elastomeric member 7410 can be formulated to minimize any reduction in the efficacy of the medicament (e.g., the epinephrine formulation) that may result from contact (either direct or indirect) between the elastomeric member 7410 and the medicament. For example, in some embodiments, the elastomeric member 7410 can be formulated to minimize any leaching or out-gassing of compositions that may have an undesired effect on the medicament. In other embodiments, the elastomeric member 7410 can be formulated to maintain its chemical stability, flexibility and/or sealing properties when in contact (either direct or indirect) with the medicament over a long period of time (e.g., for up to six months, one year, two years, five years or longer).

The prefilled syringe 7400 can have any suitable size (e.g., length and/or diameter) and can contain any suitable volume of the medicament (e.g., the epinephrine formulation), as described herein. In some embodiments, the prefilled syringe 7400 can be a prefilled (or prefillable) syringe of the types manufactured by Becton Dickinson, Gerresheimer, Ompi Pharma or others. For example, in some embodiments, the prefilled syringe 7400 (and any of the medicament container assemblies described herein) can be a Becton Dickinson "BD Hypak Physiolis" prefillable syringe containing the epinephrine formulation described herein.

The needle sheath 7720 includes a distal end portion 7721 and a proximal end portion 7722. The sheath defines a bore that receives the needle 7452 and/or the distal end portion of the 7402 of the container body 7401. The inner portion of the needle sheath 7720 defines a friction fit with the distal end portion 7402 of the medicament container body 7401. In this manner, the needle sheath 7720 can protect the user from the needle 7452 and/or can keep the needle 7452 sterile before the user actuates the medical injector.

Although the methods and the medical injector 4000 described above include an energy storage member that produces a force to insert the needle and deliver the dose, in other embodiments, an infant-dose medical injector need not include an energy storage member contained therein that produces a force to either insert the needle, deliver the medicament through the needle, or both. For example, in some embodiments, a device can be configured for manual insertion (i.e., insertion of the needle caused by an insertion force directly produced by the user) and automatic injection (i.e., injection caused by a force produced by an energy storage member). In other embodiments, a device can be configured for automatic insertion (i.e., insertion of the needle caused by an insertion force produced by an energy storage member) and manual injection (i.e., injection caused by a force directly produced by the user). In yet other embodiments, an infant-dose medical injector can be devoid of an energy storage member that produces either a needle insertion force or an injection force. In such embodiments, the medical injector can include a housing that advantageously blocks light from the medicament, thereby limiting the degradation of the medicament and improving the long-term stability. Moreover, the medical injector can include mechanisms (e.g., end stop surfaces, release mechanisms, or the like) that produce a delivered dose tolerance of ±15 percent of a nominal dose volume. Such tolerance can be of heightened importance for low dose and/or low volume therapeutic regimens, such as for example, for an infant-dose of epinephrine. By maintaining the tolerance, even at dosage volumes of as low as 0.1 mL, the medical injectors and devices described herein can provide an emergency treatment solution that is appropriate for a patient population weighing less than 15 kg (e.g., between 7.5 kg and 15 kg), that can be stored for long periods of time, and that can be administered via an untrained user without the need to measure, monitor, or otherwise limit the dose volume.

For example, FIGS. 62-65 show schematic illustrations of a medical injector (or drug product) 6000 according to an embodiment in various operating configurations (or stages of use). The medicament delivery device 6000 includes a housing 6110, a medicament container 6400, a safety member 6700, an actuator 6302, and a dose limiter 6527. The housing 6100 has a proximal end portion 6140 and a distal end portion 6120. The distal end portion 6120 includes a contact surface 6330, which can be a portion of the housing 6110 (i.e., monolithically constructed with the housing) or a structure separately coupled to the housing 6110. The contact surface 6330 is a surface that contacts a target location T of a patient during the delivery of any of the epinephrine compositions (or other drugs) disclosed herein. In some embodiments, the contact surface 6330 can have any suitable size and/or shape to maintain contact with the target location T during a delivery event. Specifically, the contact surface 6330 can have any shape as described herein, including a circular shape, a substantially rectangular shape, an oval shape, or the like. In some embodiments, the contact surface 6330 can be movably coupled to the housing 6110 (e.g., the contact surface 6330 can be spring-loaded to move when a threshold force has been applied the target location T). In other embodiments, the contact surface 6330 can be fixedly coupled to the housing 6110.

The medicament container 6400 is at least partially disposed within the housing 6110, and contains (i.e., is filled or partially filled with) an epinephrine composition 6420. The medicament container 6400 can be any container suitable for storing the epinephrine composition 6420. In some embodiments, the medicament container 6400 can be, for example, a prefilled syringe, a prefilled cartridge, a vial, an ampule or the like. For example, in some embodiments, the medicament container 6400 can be a prefilled syringe similar to the of the prefilled syringes shown and described in U.S. Pat. No. 9,084,849 entitled "Medicament Delivery Devices for Administration of a Medicament within a Prefilled Syringe," or in International Patent Publication No. WO2017/004345, entitled "Auto-Injectors for Administration of a Medicament within a Prefilled Syringe," each of which is incorporated herein by reference in its entirety. In other embodiments, the medicament container 6400 can be a prefilled syringe similar to the prefilled syringe 7400 described herein. In yet other embodiments, the medicament container 6400 can be a container having a flexible wall, such as, for example, a bladder. As shown, the proximal end portion of the medicament container 6400 contains an elastomeric member 6410 to seal the proximal end portion of the medicament container 6400. The elastomeric member 6410 can be disposed within the medicament container 6400 during the fill process, and can form a substantially fluid-tight seal to prevent leakage of the epinephrine composition 6420 from the medicament container 6400. As shown, the elastomeric member 6410 includes a proximal surface against which a plunger 6530 (or movable member) can exert a force to move the elastomeric member 6410 within the medicament container 6400. The plunger 6530 can be any suitable movable member, such as the movable member 4530 described above, or any other rigid rod.

The elastomeric member 6410 is formulated to be compatible with the epinephrine composition 6420. Similarly stated, the elastomeric member 6410 is formulated to minimize any reduction in the efficacy of the epinephrine composition 6420 that may result from contact (either direct or indirect) between the elastomeric member 6410 and the epinephrine composition 6420. For example, in some embodiments, the elastomeric member 6410 can be formulated to minimize any leaching or out-gassing of compositions that may have an undesired effect on the epinephrine composition 6420. In other embodiments, the elastomeric member 6410 can be formulated to maintain its chemical stability, flexibility and/or sealing properties when in contact (either direct or indirect) with epinephrine over a long period of time (e.g., for up to six months, one year, two years, five years or longer). In some embodiments, the elastomeric member 6410 can include or be composed of bromo-butyl rubber.

The epinephrine composition 6420 can be any of the epinephrine compositions described herein. In particular, the medicament container 6400 can contain a dose of epinephrine 6420 effective for administration to a patient experiencing anaphylaxis and having a weight of less than about 65 kg (33 pounds), i.e., an infant-dose auto-injector. Such an infant-dose drug product is configured to deliver 0.1 mL of solution that contains 0.1 mg of epinephrine, 0.78 mg of sodium chloride, 0.15 mg of sodium bisulfite, and hydrochloric acid to adjust the pH. In other embodiments, however, medicament container 6400 can contain a dose of epinephrine 6420 effective for administration to a patient experiencing anaphylaxis and having any weight (i.e., an adult-dose device or a pediatric-dose device, as described herein). In yet other embodiments, the medicament container 6400 can include any suitable drug of the types described herein.

Figure 63:
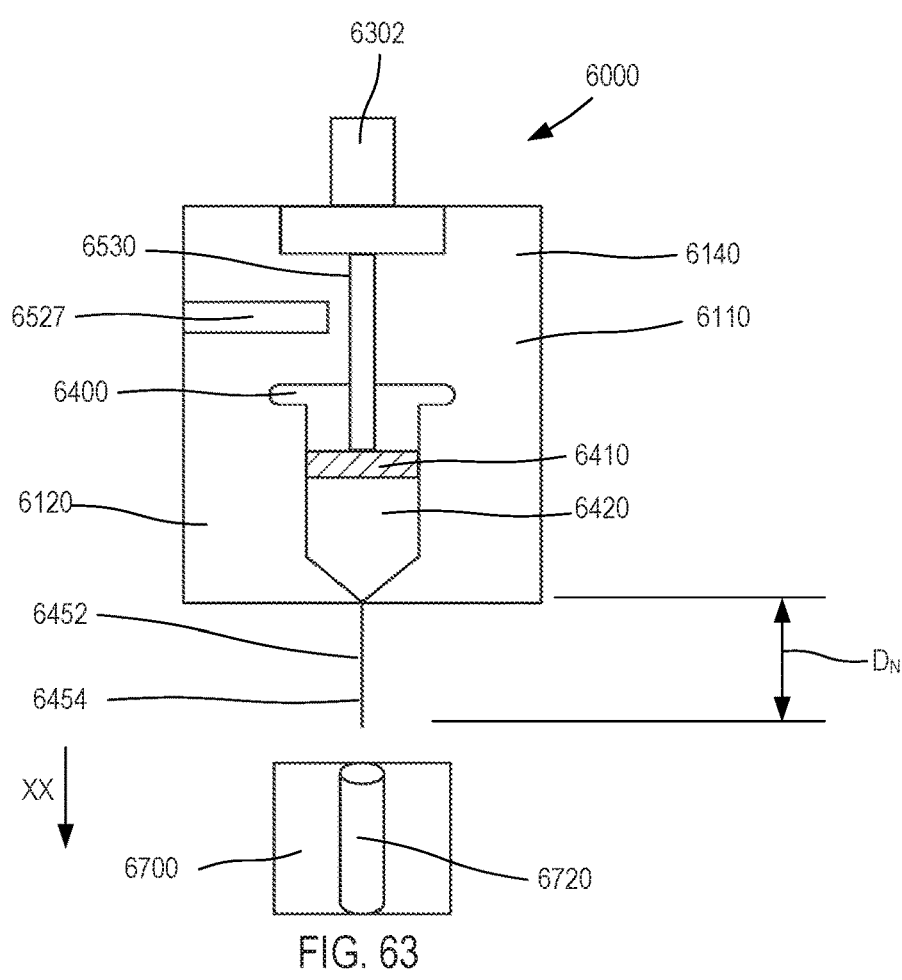
Figure 64:
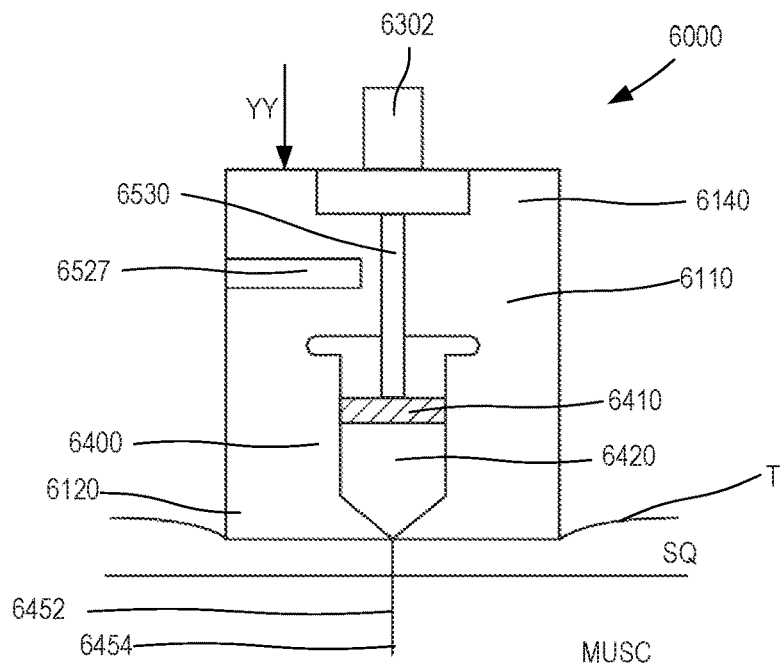
Figure 65:
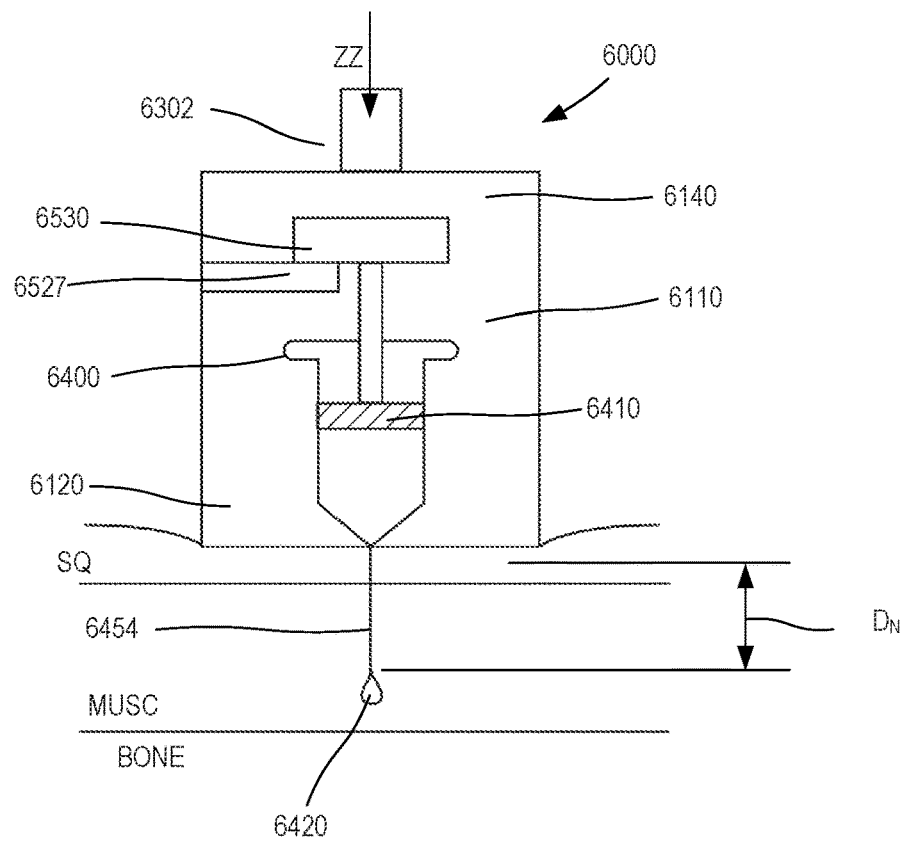

As shown, the distal end portion of the medicament container 6400 is coupled to a needle 6452. The needle 6452 includes a distal tip 6454 from which the epinephrine (or any suitable drug contained within the medicament container 6400) flows. Referring to FIGS. 63 and 65, the needle 6452 is configured such that the distal tip 6454 extends from the contact surface 6330 by distance $D_N$ sufficient such that when the needle is inserted and the contact surface 6330 is in contact with a target location, the distal tip 6454 is in the muscle layer (identified as MUSC) of the target location. Specifically, in some embodiments, the distance $D_N$ (or effective needle length) is such that the distal tip 6454 will be inserted within the thigh muscle for a patient weighing less than 15 kg (e.g., between 7.5 kg and 15 kg), and will have a low likelihood of striking the thigh bone (identified as BONE in FIGS. 64 and 65). In this manner, the distance $D_N$ is sufficient to produce an intramuscular delivery of the epinephrine 6420 while also limiting the likelihood of either an intraosseous delivery or a subcutaneous delivery. For example, in some embodiments, the distance $D_N$ is between about 6.35 mm and about 9 mm. In other embodiments, the distance $D_N$ is between about 7 mm and about 8 mm. In yet other embodiments, the distance $D_N$ is about 7.5 mm.

The needle 6452 defines a lumen that is in fluid communication with the medicament container 6400 to define a medicament delivery path through which the epinephrine composition 6420 can flow. The needle 6452 can be any gauge (e.g., 18 gauge, 23 gauge, 24 gauge, 25 gauge, 27 gauge, 32 gauge, etc.) to deliver the epinephrine composition 6420 through the lumen and into the target location T of body. The distal end tip 6454 can have any suitable bevel or shape.

The safety member 6700 is removably coupled to a distal end portion of the housing 6110 and when coupled to the housing 6100, surrounds a portion of the needle 6452. When the safety member 6700 is removed, a needle sheath 6720 is also removed from about the distal tip 6454 of the needle 6452. In this manner, prior to use the distal tip 6454 is covered by the safety member 6700 to prevent the user (or the patient) from seeing the needle 6452 to reduce the sharps hazard associated with the needle 6452, or the like. Removal of the safety member 6700 then exposes the distal tip 6454 in one motion (i.e., by pulling distally as shown by the arrow XX in FIG. 63). In some embodiments, the safety member 6700 can be similar to the safety lock 4700 or 4700' shown and described in herein. The safety member 6700 can include numerals, arrows, or other instructions to guide the user in the operation of the device 6000. In some embodiments, the safety member 6700 can include a lock surface that limits movement of a component within the medical injector 6000 (e.g., the actuator 6302) to prevent the medical injector from being actuated. In other embodiments, however, the safety member 6700 covers the needle 6452 to prevent the medical injector from delivering the dose of epinephrine therein.

The actuator 6302 is any suitable device or mechanism that actuates the medical injector 6000. In particular, as shown in FIGS. 64 and 65, the actuator 6302 can be moved relative to the housing 6110 (as shown by the arrow ZZ) from a first actuator position to a second actuator position to move the plunger 6530 within the medicament container 6400 to deliver the dose of epinephrine 6420. In some embodiments, the actuator 6302 is coupled to the plunger 6530 and transfers a force exerted by the user to the plunger 6530 to cause movement of the plunger 6530. In some embodiments, the actuator 6302 can include a detent that matingly engages a detent of the housing to maintain the actuator 6302 in its first position. Such mating detents can be similar to the recesses 4125A and the connection protrusions 4358 described above. Such an arrangement maintains the actuator 6302 in its first position until a threshold force (i.e., an actuator release force) is exceeded by the user. In this manner, the likelihood of inadvertent actuation of medical injector 6000 (e.g., by the application of a nominal force against the actuator during needle insertion, removal of the safety member 6700, or the like) is limited. This arrangement therefore improves the accuracy of the delivered dose by limiting any "pre-injection" dribble that could be caused by inadvertent forces applied to the actuator 6302.

Moreover, by limiting the distal movement of the actuator until an actuation force above the threshold force is applied, the likelihood that the full dose will be delivered is increased. Specifically, by including a detent arrangement, the user will necessarily apply a force of significant magnitude to release the "snap fit" of the detents. Upon release, the force applied by the user will naturally be maintained, and will be of sufficient magnitude to move the plunger 6530 (and therefore the elastomeric member 6410) to overcome the force of friction, viscosity losses (through the needle 6452) and the like, thereby ensuring delivery of the entire dose of epinephrine within a desired time limit (e.g., within 2 seconds).

In addition to including one or more detents to limit distal movement of the actuator 6302, in some embodiments, the actuator 6302 can include a detent that matingly engages a detent of the housing to maintain the actuator 6302 in its second position. Such mating detents can be similar to the recesses 4125B and the connection protrusions 4358 described above. Such detents can act as a dose limiter, or in conjunction with the dose limiter 6527 described below. By limiting proximal movement of the actuator 6302 after the plunger 6530 has moved through its full stroke, detents can cooperatively prevent "kickback" of the actuator 6302 (and the plunger 6530) after the medical injector 6000 has been actuated. This arrangement can also improve the accuracy of the delivered dose by limiting any post-injection retrograde movement of the medicament caused by tissue back pressure, friction within the needle 6452, or the like.

Although the actuator 6302 is shown as being disposed at the proximal end portion of the housing 6110, in other embodiments, the actuator 6302 can be located at the distal end portion of the housing 6110. In some embodiments, for example, the contact surface 6330 and the actuator 6302 can be monolithically constructed. Said another way, in some embodiments, the actuator 6302 can be a distal-end actuator and can include the contact surface 6330.

The dose limiter 6527 can be any suitable mechanism that limits further distal movement of the plunger 6530 and/or the elastomeric member 6410 after a desired dose volume has been delivered. In this manner, when the actuator 6302 is manually depressed, the user need not monitor the movement of the plunger 6530 or the elastomeric member 6410 to ensure that the proper dose is delivered. Rather, the user can simply maintain the actuation force and the dose limiter 6527 stops distal movement of the plunger 6530 and/or the elastomeric member 6410 to maintain the volume of the delivered dose to within ±15 percent of a nominal dose volume. In some embodiments, the dose limiter 6527 can be an end stop surface of the housing 6110 that is keyed or otherwise indexed to a portion of the medicament container 6400 (e.g., a flange) to ensure that the plunger 6530 moves an accurate distance within the medicament container 6400. In other embodiments, the dose limiter 6527 can be a release actuator that actuates a gas release valve (similar to the gas valve actuator 4527 described above) or otherwise decouples the actuation force from the plunger 6530 to stop distal movement of the plunger 6530.

The use of the medical injector 6000 is shown in FIGS. 62-65, which show the medical injector 6000 in various configurations. To deliver the dose of epinephrine 6420, the medicament delivery device 6000 is first enabled by removing the safety member 6700, as shown by the arrow XX in FIG. 63. As described above, the removal of the safety member 6700 exposes the needle 6452 having a desired length. The housing 6110 of the medical injector 6000 is then moved until the contact surface 6330 is in contact with the target location T, as shown by the arrow YY in FIG. 64. The target location T can be any suitable location of the patient to which the epinephrine 6420 will be delivered. For example, the target location can be the thigh of the patient. As shown, the target location can include a subcutaneous layer SQ, a layer of muscle MUSC, and a bone (identified as BONE) beneath the muscle MUSC. Although not shown, the target location T is covered by a layer of skin.

By moving the housing 6110 distally, the needle tip 6454 is inserted into the target location T to a needle depth of $D_N$ (or effective needle length). This distance is selected such that the distal tip 6454 will be inserted within the thigh muscle for a patient weighing less than 15 kg (e.g., between 7.5 kg and 15 kg), and will have a low likelihood of striking the thigh bone (identified as BONE). In this manner, the distance $D_N$ is sufficient to produce an intramuscular delivery of the epinephrine 6420 while also limiting the likelihood of either an intraosseous delivery or a subcutaneous delivery. For example, in some embodiments, the distance $D_N$ is between about 6.35 mm and about 9 mm. In other embodiments, the distance $D_N$ is between about 7 mm and about 8 mm. In yet other embodiments, the distance $D_N$ is about 7.5 mm. In some embodiments, the needle-based delivery of the medicament delivery device 6000 can accommodate delivery through a layer of clothing between the contact surface 6330 and the skin. Specifically, the medicament delivery device 6000 can be configured to insert the needle 6452 with sufficient force, and the needle 6452 can extend a sufficient distance $D_N$ such that the epinephrine 6420 can be delivered through one or more layers of clothing. Such layers can include typical infant clothing, such as pajamas with leggings, denim material, or the like.

To actuate the device, the housing 6110 and the contact surface 6330 are maintained firmly against the target location T by applying a distal force on the housing 6110. The actuator 6302 is manipulated to cause delivery of the medicament. In particular, the actuator 6302 is moved in the distal direction (as shown by the arrow ZZ in FIG. 65) and at least a portion of the force is applied to the plunger 6530, causing the plunger 6530 to move within the medicament container 6400. Movement of the plunger 6530 causes the dose of the epinephrine 6420 to be delivered intramuscularly to the patient, as shown in FIG. 65. In particular, in some embodiments, the medicament delivery device 6000 can deliver a dose of epinephrine 6420 effective for administration to a patient experiencing anaphylaxis and having a weight of less than about 15 kg (33 pounds), i.e., an infant-dose autoinjector. Such an infant-dose drug product is configured to deliver 0.1 mL of solution that contains 0.1 mg of epinephrine, 0.78 mg of sodium chloride, 0.15 mg of sodium bisulfite, and hydrochloric acid to adjust the pH. In other embodiments, the medicament delivery device 6000 can deliver a dose of epinephrine 6420 effective for administration to a patient experiencing anaphylaxis and having a weight of between about 7.5 kg and about 15 kg (33 pounds). In such embodiments, the drug product is configured to a solution that contains between about 0.06 mg and about 0.15 mg of epinephrine. In yet other embodiments, the medicament container 6400 can include any suitable drug of the types described herein.

As described above, the plunger 6530 is moved distally until its movement is limited by the dose limiter 6527. In this manner, the dose limiter 6527 can maintain the volume of the delivered dose to within ±15 percent of a nominal dose volume.

Figure 66:
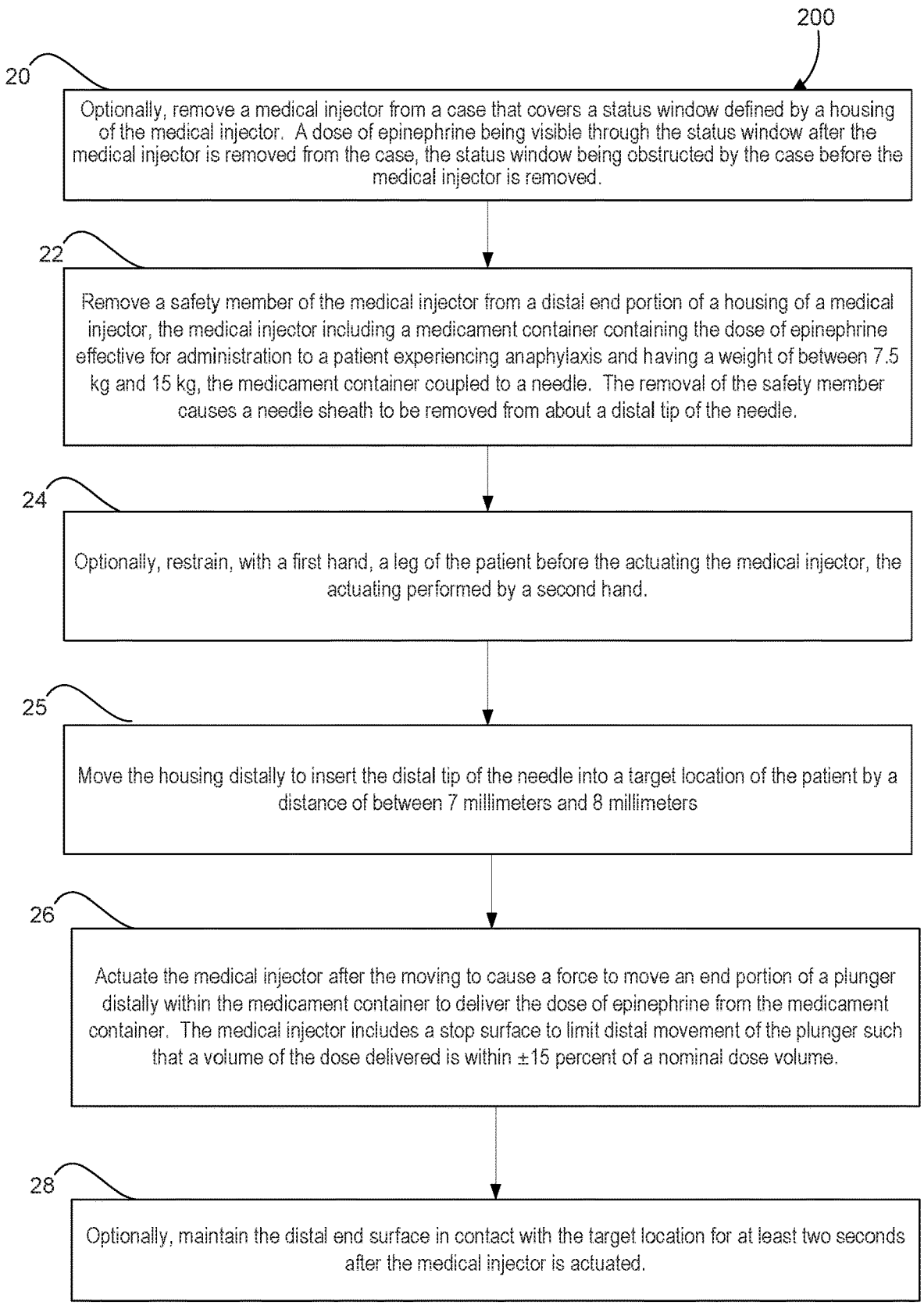
FIG. 66 is a flow chart of a method of delivering drugs, according to an embodiment.

FIG. 66 is a flow chart is showing a method 200 of using a delivery device to deliver a dose of epinephrine to a patient weighing less than 15 kg (and more specifically, between 7.5 kg and 15 kg) according to an embodiment. The method 200 can be performed with any of the medicament delivery devices (or drug products) described herein, including the delivery device 4000 or 6000. For purposes of explanation, the method 200 is described with reference to FIGS. 62-65, which show the device 6000. In some embodiments, the method 200 optionally includes removing a medical injector from a case that covers a status window defined by a housing of the medical injector, at 20. The case can be similar to the case 4200 and the status window can be similar to the status window 4150 described above with connection to the medical injector 4000. Accordingly, a dose of epinephrine is visible through the status window after the medical injector is removed from the case, and the status window is obstructed by the case before the medical injector is removed from the case. In this manner, the case prevents the epinephrine from being exposed to ultraviolet radiation via the status window.

The method includes removing a safety member (e.g., the safety member 6700) from a distal end portion of the housing of the medical injector, at 22. The medical injector includes a medicament container containing a dose of epinephrine effective for administration to a patient experiencing anaphylaxis and having a weight of between 7.5 kg and 15 kg. The medicament container, which can be a prefilled syringe (e.g., the prefilled syringe 7400), is coupled to a needle, and removal of the safety member causes a needle sheath to be removed from about a distal tip of the needle. In this manner, moving (or removing) the safety member exposes the needle places the medical injector in a "ready" state.

In some embodiments, the target location for injection is the thigh, and more specifically, the anterolateral aspect of the thigh, as indicated by the reference character T and the shaded region shown in FIG. 11B. In some embodiments, the method 200 optionally includes pinching a thigh muscle of the patient before actuating the medical injector. In other embodiments, the method optionally includes holding and/or limiting movement of the target location before and after the medical injector is actuated, at 24. Specifically, in some embodiments, the method 100 optionally includes restraining a leg of the patient with a first hand, and actuating the device with a second hand. In this manner, the likelihood that the patient will move suddenly to disrupt the delivery process is minimized. Although the method 200 includes restraining the leg of the patient with the user's hand (H1), in other embodiments, a method can include restraining the leg of the patient by any suitable method. For example, in some embodiments, the user can support the patient on the user's lap and restrain the patient's leg between the user's legs. This can allow one hand of the user to restrain the patient's arms or torso, while using the other hand to manipulate the medical injector.

The housing of the medical injector is then moved distally to insert the distal tip of the needle into a target location of the patient by a distance of between 7 millimeters and 8 millimeters, at 25. In some embodiments, the housing is moved until a distal end surface of the medical injector is placed into contact with a target location of a patient.

The medical injector is then actuated to cause a force to move an end portion of a plunger distally within the medicament container to deliver the dose of epinephrine from the medicament container, at 26. The medical injector includes a stop surface to limit distal movement of the plunger such that a volume of the dose delivered is within ±15 percent of a nominal dose volume. The stop surface can be a dose limiter of the types shown and described herein. In some embodiments, the dose of epinephrine contains between about 0.06 mg epinephrine and about 0.150 mg epinephrine. In some embodiments, the dose of epinephrine contains about 0.1 mg epinephrine. In some embodiments, the dose of epinephrine includes about 0.1 mL of a solution containing about 0.1 mg epinephrine, about 0.78 mg sodium chloride, and about 0.15 mg sodium bisulfite hydrochloric acid.

In some embodiments, the method 200 optionally includes maintaining the distal end surface in contact with the target location for at least two seconds after the medical injector is actuated, at 28.

Compositions

In some embodiments, any of the medicament delivery devices described herein can include a composition including epinephrine to form a drug product suitable for performing the methods described herein. The present epinephrine compositions may be adapted for various administration routes, depending on the apparatus in which such epinephrine composition) are to be employed. For example, in some embodiments, the present compositions may be adapted for parenteral administration as, for example, an injectable solution.

In some embodiments, a drug product includes an effective amount of epinephrine, i.e., (−)-3,4-Dihydroxy-α-[(methylamino)methyl]benzyl alcohol. As used herein, an "effective amount" is an amount sufficient to provide a desired therapeutic effect. For example, as described herein, the present epinephrine compositions may be useful in treating allergic reactions. Such allergic reactions include anaphylaxis to stinging insects (e.g., order Hymenoptera, which include bees, wasps, hornets, yellow jackets and fire ants) and biting insects (e.g., triatoma, mosquitoes), allergen immunotherapy, foods, drugs, diagnostic testing substances (e.g., radiocontrast media) and other allergens, as well as idiopathic anaphylaxis or exercise-induced anaphylaxis. Accordingly, an effective amount of epinephrine in the present compositions, delivery devices and/or drug products may be an amount sufficient to treat such anaphylaxis and/or other indications associated with allergic reactions. In particular, in some embodiments, a drug product containing a dose of epinephrine effective for administration to a patient experiencing anaphylaxis and having a weight of greater than about 30 kg (66 pounds), i.e., an adult-dose auto-injector, contains 0.3 mg of epinephrine. A drug product containing a dose of epinephrine effective for administration to a patient experiencing anaphylaxis and having a weight of between about 15 kg (33 pounds) and about 30 kg (66 pounds), i.e., a pediatric-dose auto-injector, contains 0.15 mg of epinephrine. A drug product containing a dose of epinephrine effective for administration to a patient experiencing anaphylaxis and having a weight of less than about 15 kg (33 pounds), and more specifically between 7.5 kg and 15 kg, i.e., an infant-dose auto-injector, contains 0.10 mg of epinephrine. Although the phrases "adult-dose," "pediatric-dose," and "infant-dose" are used herein, it is understood that such devices and methods are applicable to any patient within the prescribed weight ranges, even if the patient may not be considered an "adult," a "pediatric patient," or an "infant" by some definitions. For example, the "infant-dose" methods, drug products, and devices described herein are applicable to a child weighing 14 kg, even if that child is considered a toddler or pediatric patient (i.e., is not considered an "infant").

The present epinephrine compositions typically have a concentration of about 1 mg/mL. Specifically, each 0.3 mL of solution contains 0.3 mg of epinephrine, each 0.15 mL of solution contains 0.15 mg of epinephrine, and each 0.1 mL of solution contains 0.1 mg of epinephrine. In other embodiments, however, a drug product can include an epinephrine solution having any suitable concentration. For example, in some embodiments, a drug product and/or method can employ an epinephrine solution having an epinephrine concentration of between about 0.01 mg/mL and about 10 mg/mL (e.g., between about 0.05 mg/mL and about 2 mg/mL, or any other value or range of values therein, including between about 0.1 mg/mL and about 1.9 mg/mL, between about 0.2 mg/mL and about 1.8 mg/mL, between about 0.3 mg/mL and about 1.7 mg/mL, between about 0.4 mg/mL and about 1.6 mg/mL, between about 0.5 mg/mL and about 1.5 mg/mL, between about 0.6 mg/mL and about 1.4 mg/mL, between about 0.7 mg/mL and about 1.3 mg/mL, between about 0.8 mg/mL and about 1.2 mg/mL, between about 0.9 mg/mL and about 1.1 mg/mL).

In some embodiments, the present epinephrine compositions comprise a pH adjusting agent. In some embodiments, the pH adjusting agent includes at least one of hydrochloric acid, citric acid, acetic acid, phosphoric acid, or combinations thereof. In certain embodiments, the pH adjusting agent is added in an amount sufficient to provide a pH of the present epinephrine compositions of from about 2.2 to about 5 (for example a pH of about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, or about 5.0).

In some embodiments, the present epinephrine compositions may also comprise one or more tonicity-adjusting agents. For example, the tonicity-adjusting agent may include at least one of dextrose, glycerin, mannitol, potassium chloride, sodium chloride, or combinations thereof.

In some embodiments, a drug product containing a dose of epinephrine effective for to a patient experiencing anaphylaxis and having a weight of greater than about 30 kg (66 pounds), i.e., an adult-dose auto-injector, is configured to deliver 0.3 mL of solution. Each 0.3 mL contains 0.3 mg of epinephrine, 2.3 mg of sodium chloride, 0.5 mg of sodium bisulfite, and hydrochloric acid to adjust the pH. In some embodiments, a drug product containing a dose of epinephrine effective for to a patient experiencing anaphylaxis and having a weight between about 15 kg (33 pounds) and about 30 kg (66 pounds), i.e., a pediatric-dose auto-injector, is configured to deliver 0.15 mL of solution. Each 0.15 mL contains 0.15 mg of epinephrine, 1.2 mg of sodium chloride, 0.2 mg of sodium bisulfite, and hydrochloric acid to adjust the pH. In some embodiments, a drug product containing a dose of epinephrine effective for to a patient experiencing anaphylaxis and having a weight of less than about 15 kg (33 pounds), i.e., an infant-dose auto-injector, is configured to deliver 0.1 mL of solution. Each 0.1 mL contains 0.1 mg of epinephrine, 0.78 mg of sodium chloride, 0.15 mg of sodium bisulfite, and hydrochloric acid to adjust the pH.

In some embodiments, the electronic circuit system 4900 can be used in either an actual medicament delivery device or a simulated medicament delivery device. A simulated medicament delivery device can, for example, correspond to an actual medicament delivery device and can be used, for example, to train a user in the operation of the corresponding actual medicament delivery device.

The simulated medicament delivery device can simulate the actual medicament delivery device in any number of ways. For example, in some embodiments, the simulated medicament delivery device can have a shape corresponding to a shape of the actual medicament delivery device, a size corresponding to a size of the actual medicament delivery device and/or a weight corresponding to a weight of the actual medicament delivery device. Moreover, in some embodiments, the simulated medicament delivery device can include components that correspond to the components of the actual medicament delivery device. In this manner, the simulated medicament delivery device can simulate the look, feel and sounds of the actual medicament delivery device. For example, in some embodiments, the simulated medicament delivery device can include external components (e.g., a housing, a needle guard, a sterile cover, a safety lock or the like) that correspond to external components of the actual medicament delivery device. In some embodiments, the simulated medicament delivery device can include internal components (e.g., an actuation mechanism, a compressed gas source, a medicament container or the like) that correspond to internal components of the actual medicament delivery device.

In some embodiments, however, the simulated medicament delivery device can be devoid of a medicament and/or those components that cause the medicament to be delivered (e.g., a needle, a nozzle or the like). In this manner, the simulated medicament delivery device can be used to train a user in the use of the actual medicament delivery device without exposing the user to a needle and/or a medicament. Moreover, the simulated medicament delivery device can have features to identify it as a training device to prevent a user from mistakenly believing that the simulated medicament delivery device can be used to deliver a medicament. For example, in some embodiments, the simulated medicament delivery device can be of a different color than a corresponding actual medicament delivery device. Similarly, in some embodiments, the simulated medicament delivery device can include a label clearly identifying it as a training device.

In some embodiments, a kit includes a simulated auto-injector (or "trainer") and one or more actual auto-injectors. The actual auto-injector can be any of the medicament delivery devices described herein, such as the auto-injector 4000, or the auto-injector 4000 including the carrier 5520 and the needle 5452. The simulated auto-injector can be any of the simulated devices and/or trainers shown and described in U.S. Patent Publication No. 2008/0059133, entitled "Medical Injector Simulation Device," which is incorporated herein by reference in its entirety.

Figure 67:
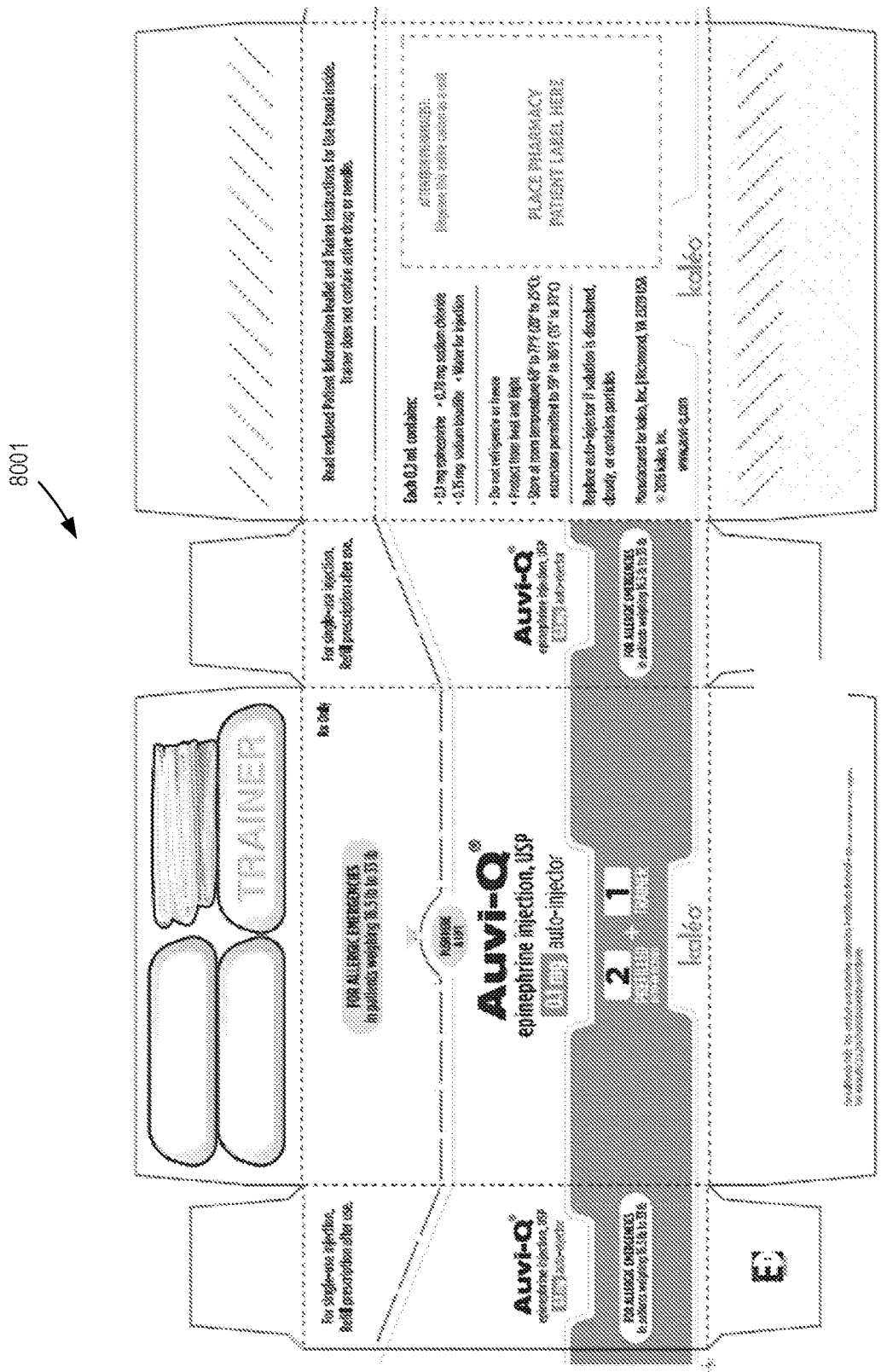
FIG. 67 is a top view of a container of a kit according to an embodiment.

FIG. 67 is a top view of a container 8001 of a kit according to an embodiment. The container is in a flat (or unfolded) configuration. As shown, the kit includes two auto-injectors configured to deliver a dose of epinephrine effective for administration to the patient experiencing anaphylaxis and having a weight of between 7.5 kg and 15 kg. The kit can also optionally include one "trainer" or simulated medical injector. In some embodiments, the container 8001 can be color-coded to provide an additional indication that the medical injectors therein are suited for patients having a weight of between 7.5 kg and 15 kg. For example, in some embodiments, portions of the container 8001 and/or the devices therein can be orange to indicate an adult dosage (greater than 30 kg), blue to indicate a pediatric dosage (between 15 kg and 30 kg) and lavender to indicate an infant dosage (between 7.5 kg and 15 kg).

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Although the medical injector 4000 includes the electronic circuit system cavity 4153, the gas cavity 4154 and/or the medicament cavity 4157 that are shown and described as being fluidically and/or physically isolated from each other, in other embodiments, any of the electronic circuit system cavity 4153, the gas cavity 4154 and/or the medicament cavity 4157 can be fluidically coupled to and/or share a common boundary with each other. In some embodiments, for example, a housing can define a single cavity within which a medicament container, an energy storage member and an electronic circuit system are disposed.

Although the medical injector 4000 discloses a gas-powered delivery device, in other embodiments, any of the medicament delivery devices disclosed herein can include any suitable energy storage member. Such energy storage members can be, for example, a mechanical energy storage member, such as a spring, a device containing compressed gas, a device containing a vapor pressure-based propellant or the like. In other embodiments, the energy storage member can be an electrical energy storage member, such as a battery, a capacitor, a magnetic energy storage member or the like. In yet other embodiments, the energy storage member can be a chemical energy storage member, such as a container containing two substances that, when mixed, react to produce energy.

The medicament containers and/or medicament delivery devices disclosed herein can contain any suitable amount of any of the epinephrine compositions disclosed herein. Moreover, although the medicament delivery devices, auto-injectors and/or drug products are described herein as including a dose of epinephrine, in other embodiments, any of the medicament delivery devices, auto-injectors and/or drug products can include any suitable dose of any suitable drug. For example, in some embodiments, the medicament contained within any of the medicament containers and/or drug products shown herein can be an opioid receptor antagonist, such as naloxone, including any of the naloxone formulations described in U.S. Pat. No. 8,627,816, entitled "Medicament Delivery Device for Administration of Opioid Antagonists Including Formulation for Naloxone," filed on Feb. 28, 2011, which is incorporated herein by reference in its entirety. In other embodiments, the medicament contained within any of the medicament containers shown herein can include peptide hormones such as insulin and glucagon; human growth hormone (HGH); sumatriptan; a corticosteroid such as dexamethasone; ondansetron; an opioid agonist receptor modulators such as fentanyl; a partial agonist opioid receptor modulators such as buprenorphine; a mixed agonist/antagonist opioid receptor modulator such as nalbuphine; a benzodiazepine such as diazepam, midazolam or lorazepam; erythropoiesis-stimulating agents (ESA) such as darbepoetin alfa; immunoglobulins including dual-variable domain immunoglobulins; interferons; anti-tumor; recombinant human granulocyte colony-stimulating factor (GCSF) such as pegfilgrastim; and other therapies suitable for injection in mammals. In yet other embodiments, the medicament contained within any of the medicament containers shown herein can be a placebo substance (i.e., a substance with no active ingredients), such as water.

In yet other embodiments, any of the devices and/or medicament containers shown and described herein can include any suitable medicament or therapeutic agent. In some embodiments, the medicament contained within any of the medicament containers shown herein can be a vaccine, such as, for example, an influenza vaccine, a hepatitis vaccine, a haemophilus influenza Type B (HiB) vaccine, a measles vaccine, a mumps vaccine, a rubella vaccine, or combination vaccine (e.g. measles, mumps and rubella, quadrivalent, or hexavalent vaccines), a polio vaccine, a human papilloma virus (HPV) vaccine, a tetanus vaccine, a diphtheria vaccine, a pertussis vaccine, a bubonic plague vaccine, a yellow fever vaccine, a cholera vaccine, a malaria vaccine, a smallpox vaccine, a pneumococcal vaccine, a rotavirus vaccine, a varicella vaccine, a dengue fever vaccine, a rabies vaccine and/or a meningococcus vaccine.

Any of the devices and/or medicament containers shown and described herein can contain and/or deliver a wide array of large or macromolecular injectables that include carbohydrate-derived formulations, lipids, nucleic acids, proteins/peptides (e.g. monoclonal antibodies) and other biotechnologically-derived medicaments. For example, anti-tumor necrosis factor agents such as infliximab, etanercept, adalimumab, golimumab, natalizumab, vedolizumab, and certolizumab can be administered using the described auto-injector heroin, Other macromolecular injectable medications that can be administered using the device and/or medicament containers shown and described herein include viscous medicaments that target pro-inflammatory cytokines (e.g. IL-1, IL-2, IL-4, IL-5, IL-6, IL-12, IL-13, IL-23, IL-17, IL-21 and associated receptors) including dupilumab, sarilumab, mepolizumab, benralizumab, reslizumab, lebrikizumab, ustekinumab, anrunkinzumab, bertilimumab, and tralokinumab. Large anti-adhesion molecules to treat a variety of diseases may be administered using the device and/or medicament containers shown and described herein including etrolizumab and vatelizumab. Still other large and viscous monoclonal antibodies that may be administered using the device and/or medicament containers shown and described herein include tezepelumab, anifrolumab, omalizumab, and proprotein convertase subtilisin kexin type 9 (PCSK9) inhibitors including alirocumab and evolocumab.

Although the medical injector 4000 is shown and described herein as including mechanisms for needle retraction, in other embodiments any of the injectors shown and described herein can include a needle shield that extends distally after the injection to cover the exposed needle. For example, in some embodiments, a base of a medical injector (e.g. the base 4302) can be (or include) an extending portion that, upon completion of the injection, extends distally to cover the needle. In some such embodiments, the gas vent assembly can divert all or a portion of the pressurized gas to a volume within the housing such that the diverted gas exerts a force on the base (or a portion of the base) to cause the base (or portion of the base) to extend distally to cover the needle.

In other such embodiments, a spring, biasing member, or retraction member can propel the base (or portion of the base) distally. In yet other embodiments, a medical injector can include a cap or cover that can be placed over the exposed needle when the injection is completed.

Although the medical injector 4000 and the medical injector 6000 are each shown and described as including a needle, in other embodiments, a medical injector need not include a needle to inject the dose of epinephrine intramuscularly in a patient weighing between about 7.5 kg and about 15 kg. For example, in some embodiments, a device (similar to the device 4000) can include a nozzle through which the dose is delivered at a pressure sufficient to penetrate the user's skin and tissue to deliver the dose intramuscularly to the patient. Such needleless embodiments can include a pressurized gas container of the types shown and described herein, and can include a dose limiter, similar to the dose limiter 6527 described above. In this manner, a needleless medical injector can deliver a dose of epinephrine such that the volume of the dose delivered is within ±15 percent of a nominal dose volume (e.g., a nominal dose volume of 0.1 mL).

Although various embodiments have been described as having particular features and/or combinations of components, other embodiments are possible having a combination of any features and/or components from any of embodiments where appropriate. For example, any of the devices shown and described herein can include an electronic circuit system as described herein. For example, although the medicament delivery device 1000 shown in FIGS. 1-4 is not shown as including an electronic circuit system, in other embodiments, a medicament delivery device similar to the device 1000 can include an electronic circuit system similar to the electronic circuit system 4900 shown and described above.

Any of the medicament containers described herein can contain any of the epinephrine compositions and/or other drug formulations described herein.

What is claimed is:

1. A method, comprising:
   placing a distal end surface of a medical injector into contact with a target location of a patient, the medical injector including a housing, an energy storage member and a medicament container containing a dose of epinephrine effective for administration to the patient experiencing anaphylaxis, the medicament container coupled to a needle via a carrier, the carrier including a retention portion and defining a coupling volume, the retention portion of the carrier configured to retain a distal end portion of the medicament container in a first container position within the coupling volume, the distal end portion of the medicament container fluidically isolated from a proximal tip of the needle when the medicament container is in the first container position, the distal end portion of the medicament container configured to move to a second container position within the coupling volume in response to an actuation force, the distal end portion of the medicament container fluidically coupled to the proximal tip of the needle when the medicament container is in the second container position, the retention portion including an annular protrusion defining a bleed passageway from the coupling volume towards a proximal end portion of the carrier; and
   actuating the medical injector after the placing such that the energy storage member produces the actuation force to move the needle from a first needle position to a second needle position, a distal tip of the needle extending from the distal end surface by a distance of at least 6.35 millimeters when the needle is in the second needle position, the actuation force further moving the medicament container from the first container position to the second container position, a portion of the actuation force exerted to expel the dose of epinephrine from the medicament container when the needle is in the second position.

2. The method of claim 1, wherein the patient has a weight range of between 7.5 kg and 15 kg.

3. The method of claim 1, wherein the placing includes placing the distal end surface into direct contact with a clothing article covering the target location.

4. The method of claim 1, wherein:
   the distal end surface is a distal end surface of an actuator; and
   the actuating includes pressing the actuator against the target location such that the actuator moves relative to the housing to release an energy from the energy storage member.

5. The method of claim 1, wherein the distal tip of the needle extends from the distal end surface by a distance of between at least 6.35 millimeters and 8 millimeters when the needle is in the second needle position.

6. The method of claim 1, wherein the patient experiencing anaphylaxis has a weight of less than 15 kg.

7. The method of claim 1, wherein the dose of epinephrine includes about 0.1 ml of a solution containing about 0.1 mg epinephrine, about 0.78 mg sodium chloride, and about 0.15 mg sodium bisulfite hydrochloric acid.

8. The method of claim 4, wherein the actuating includes pressing the actuator against the target location with an actuator release force between about 8.9 N (2 lbf) and about 44.5 N (10 lbf).

9. The method of claim 8, wherein the force is about 26.7 N (6 lbf).

10. The method of claim 8, wherein:
    the target location is a thigh; and
    the actuation force is such that the distal tip of the needle is within a thigh muscle when the needle is in the second needle position to expel the dose of epinephrine intramuscularly into the thigh muscle.

11. The method of claim 10, further comprising:
    before the actuating, pinching the thigh muscle.

12. The method of claim 10, further comprising:
    restraining, with a first hand, a leg of the patient before the actuating, the actuating including pressing the actuator against the target location with a second hand such that the actuator moves relative to the housing to release an energy from the energy storage member.

13. An apparatus, comprising:
    a housing;
    a contact surface coupled to the housing, the contact surface configured to contact a target location of a patient;
    a medicament container at least partially disposed within the housing, the medicament container containing a dose of epinephrine effective for administration to the patient experiencing anaphylaxis, the medicament container coupled to a needle;
    a carrier including a retention portion and defining a coupling volume, the medicament container coupled to the needle via the carrier, the retention portion of the carrier configured to retain a distal end portion of the medicament container in a first container position within the coupling volume, the distal end portion of the medicament container fluidically isolated from a proximal tip of the needle when the medicament container is in the first container position, the distal end portion of the medicament container configured to move to a second container position within the coupling volume in response to an actuation force, the distal end portion of the medicament container fluidically coupled to the proximal tip of the needle when the medicament container is in the second container position, the retention portion including an annular protrusion defining a bleed passageway from the coupling volume towards a proximal end portion of the carrier;

an energy storage member within the housing, the energy storage member configured to produce the actuation force to move the needle from a first needle position to a second needle position and to move the medicament container from the first container position to the second container position, a distal tip of the needle extending from the contact surface by a distance of at least 6.35 millimeters when the needle is in the second needle position; and an actuator configured to actuate the energy storage member to release the actuation force.

14. The apparatus of claim 13, wherein the dose of epinephrine contains between about 0.06 mg epinephrine and about 0.150 mg epinephrine.

15. The apparatus of claim 13, wherein the patient has a weight range of between 7.5 kg and 15 kg.

16. The apparatus of claim 13, wherein a distal tip of the needle extending from the contact surface by a distance of between about at least 6.35 millimeters and about 9 millimeters when the needle is in the second needle position.

17. The apparatus of claim 13, wherein the dose of epinephrine includes about 0.1 ml of a solution containing about 0.1 mg epinephrine, about 0.78 mg sodium chloride, and about 0.15 mg sodium bisulfite hydrochloric acid.

18. The apparatus of claim 13, wherein:
the contact surface and the actuator are monolithically constructed; and
the actuator is coupled to a distal end portion of the housing, the actuator configured to move relative to the housing to actuate the energy storage member.

19. The apparatus of claim 18, wherein the contact surface is planar.

20. The apparatus of claim 18, wherein the actuator includes a detent protrusion configured to matingly engage a detent recess of the distal end portion of the housing, the detent protrusion of the actuator and the detent recess of the housing configured such that the actuator moves relative to the housing when an actuator release force is applied to the contact surface.

21. The apparatus of claim 20, wherein the actuator release force is between about 8.9 N (2 lbf) and about 44.5 N (10 lbf).

22. An apparatus, comprising:
a housing;
a contact surface coupled to the housing, the contact surface configured to contact a target location of a patient;
a medicament container at least partially disposed within the housing, the medicament container containing a dose of epinephrine effective for administration to the patient experiencing anaphylaxis, the medicament container coupled to a needle;
an energy storage member within the housing, the energy storage member configured to produce an actuation force to move the needle from a first needle position to a second needle position, a distal tip of the needle extending from the contact surface by a distance of at least 6.35 millimeters when the needle is in the second needle position; and
an actuator configured to actuate the energy storage member to release the actuation force;
wherein:
the medicament container includes at least 0.3 ml of a solution containing about 0.3 mg epinephrine;
a portion of the actuation force is exerted to move a plunger within the medicament container by a plunger distance to expel the dose of epinephrine when the needle is in the second needle position; and
the medicament container is coupled to the needle via a carrier, a release member of the carrier configured to release the portion of the actuation force after the plunger has moved the plunger distance,
the carrier configured to retain a distal end portion of the medicament container within a coupling volume, a retention portion of the carrier configured to retain the distal end portion of the medicament container in a first container position within the coupling volume, the distal end portion of the medicament container fluidically isolated from a proximal tip of the needle when the medicament container is in the first container position, the distal end portion of the medicament container configured to move to a second container position within the coupling volume in response to the actuation force, the distal end portion of the medicament container fluidically coupled to the proximal tip of the needle when the medicament container is in the second container position, the retention portion including an annular protrusion defining a bleed passageway from the coupling volume towards a proximal end portion of the carrier.

23. The apparatus of claim 22, wherein:
the dose of epinephrine has a nominal value of 0.10 ml of the solution; and
the release member of the carrier is configured such that a delivered dose of epinephrine is between 0.085 ml and 0.115 ml.

* * * * *